United States Patent
Hogan et al.

(10) Patent No.: US 9,416,419 B2
(45) Date of Patent: *Aug. 16, 2016

(54) METHODS FOR PCR AND HLA TYPING USING UNPURIFIED SAMPLES

(76) Inventors: Michael E. Hogan, Tuscan, AZ (US); Georgina Lopez Padilla, Tucson, AZ (US); Melissa R. May, Tucson, AZ (US); Andrew T. Abalos, Tucson, AZ (US); Frederick H. Eggars, Sahuarita, AZ (US); Kevin M. O'Brien, Sahuarita, AZ (US)

( * ) Notice: Subject to any disclaimer, the term of this patent is extended or adjusted under 35 U.S.C. 154(b) by 300 days.

This patent is subject to a terminal disclaimer.

(21) Appl. No.: 13/317,212

(22) Filed: Oct. 12, 2011

(65) Prior Publication Data

US 2012/0122719 A1    May 17, 2012

Related U.S. Application Data

(63) Continuation-in-part of application No. 12/924,301, filed on Sep. 24, 2010.

(60) Provisional application No. 61/281,404, filed on Nov. 16, 2009.

(51) Int. Cl.
*C12Q 1/68* (2006.01)

(52) U.S. Cl.
CPC ............ *C12Q 1/6881* (2013.01); *C12Q 1/6804* (2013.01); *C12Q 1/686* (2013.01); *C12Q 1/689* (2013.01); *C12Q 2600/156* (2013.01)

(58) Field of Classification Search
None
See application file for complete search history.

(56) References Cited

FOREIGN PATENT DOCUMENTS

EP         2186911     *  5/2010   ............... C12Q 1/68

OTHER PUBLICATIONS

Stanley et al. (Nucleic Acids Research, 2005, 33(20):e180).*
Biggar et al. (AIDS 1997, vol. 11, 1375-1382).*
Zhang et al. (Anal Chem, 1999, 71, p. 1138-1145).*
Sullivan et al. (Int J Leg Med, 1992, 105:83-86).*
Dunbar et al. (Appl Environ Microbiol., 2000, 66(7):2943-2950).*
Haddock et al. (Methods in Molecular Biology, 2001, vol. 170, p. 201-210).*
Xu et al. (Clin Chem, 2002, 48(9):1605-1608).*

* cited by examiner

*Primary Examiner* — Stephanie K Mummert
(74) *Attorney, Agent, or Firm* — Benjamin Aaron Adler

(57) ABSTRACT

Provided are methods for amplifying a gene or RNA or sets thereof of interest using a tandem PCR process. The primers in the first PCR or set of PCR reactions are locus-specific. The primers in the second PCR or set of PCR reactions are specific for a sub-sequence of the locus-specific primers and completely consumed during the second PCR amplification. For RNA amplification, the first PCR is reverse transcription and the resulting cDNA(s) provide a template for cRNA synthesis, endpoint PCR or real time PCR. Also provided is a tandem PCR method which accepts raw, completely unpurified mouthwash, cheek swabs and ORAGENE™-stabilized saliva as the sample input, the resulting amplicons serving as the substrate for complex, microarray-based genetic testing. Also provided is a method of allelotyping a gene or set thereof by amplifying the gene(s) using tandem PCR on DNA or RNA comprising the sample.

19 Claims, 33 Drawing Sheets

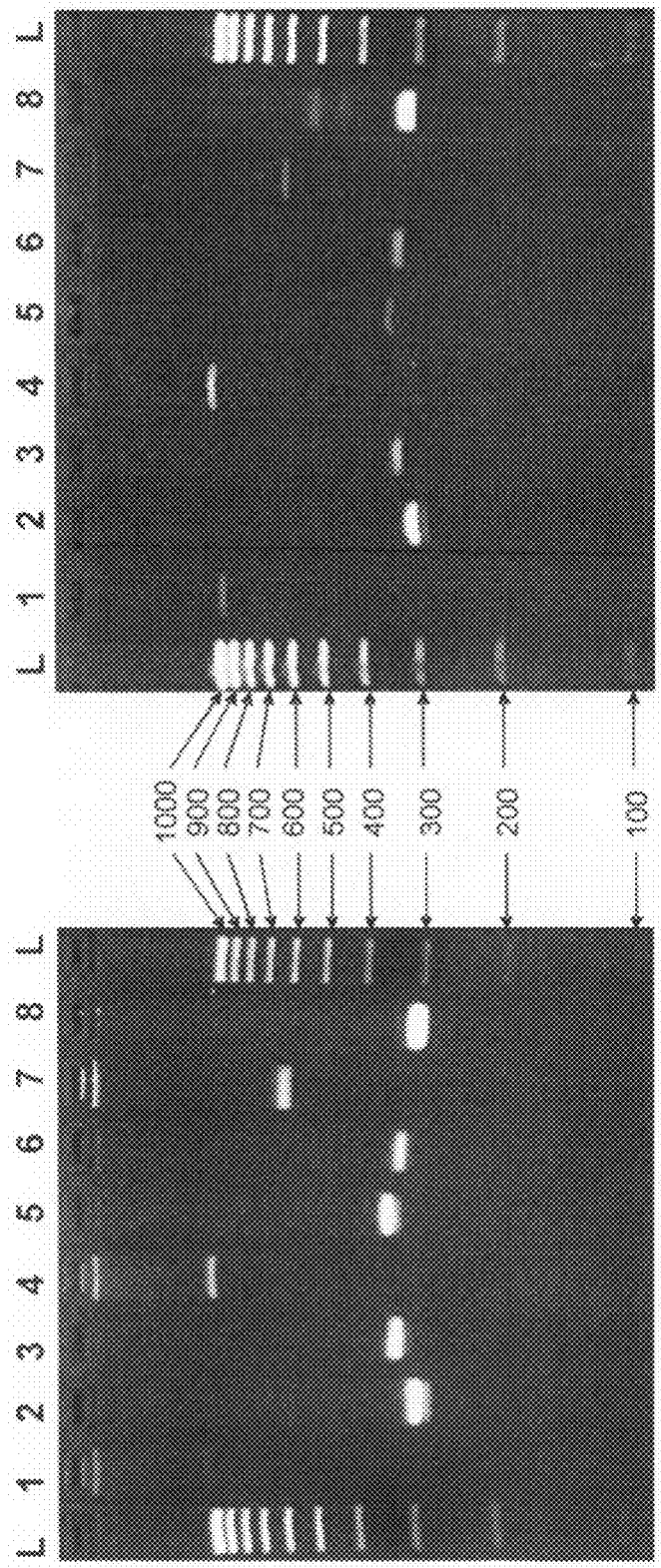

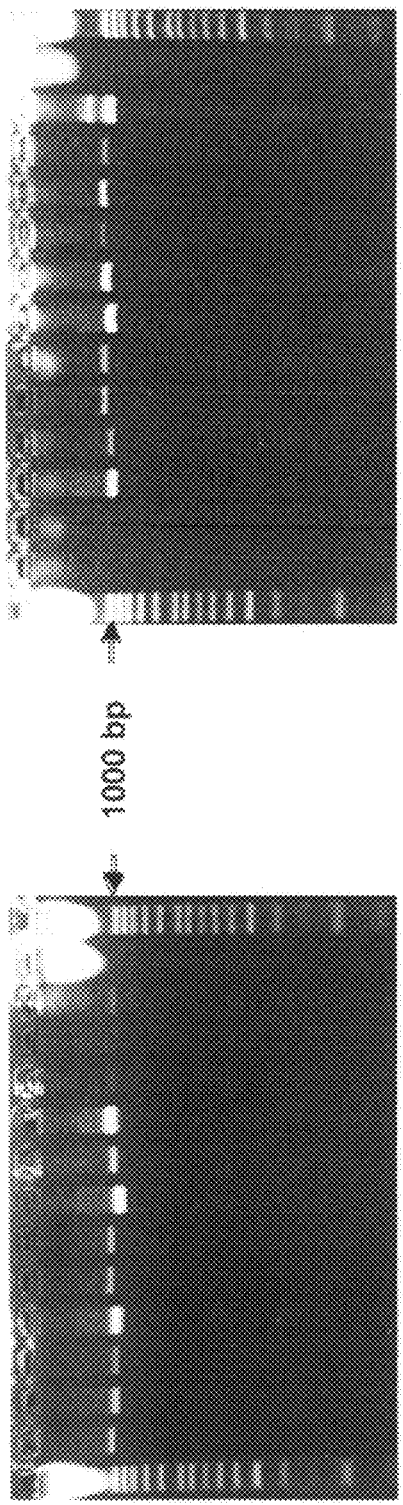
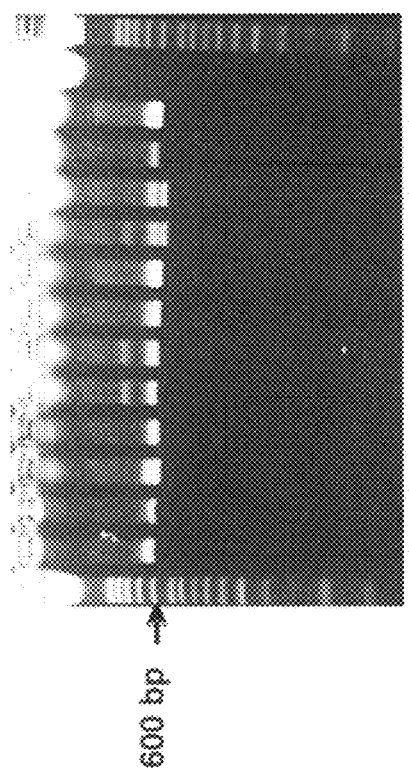
Fig. 3A
Fig. 3B
Fig. 3C 300 bp

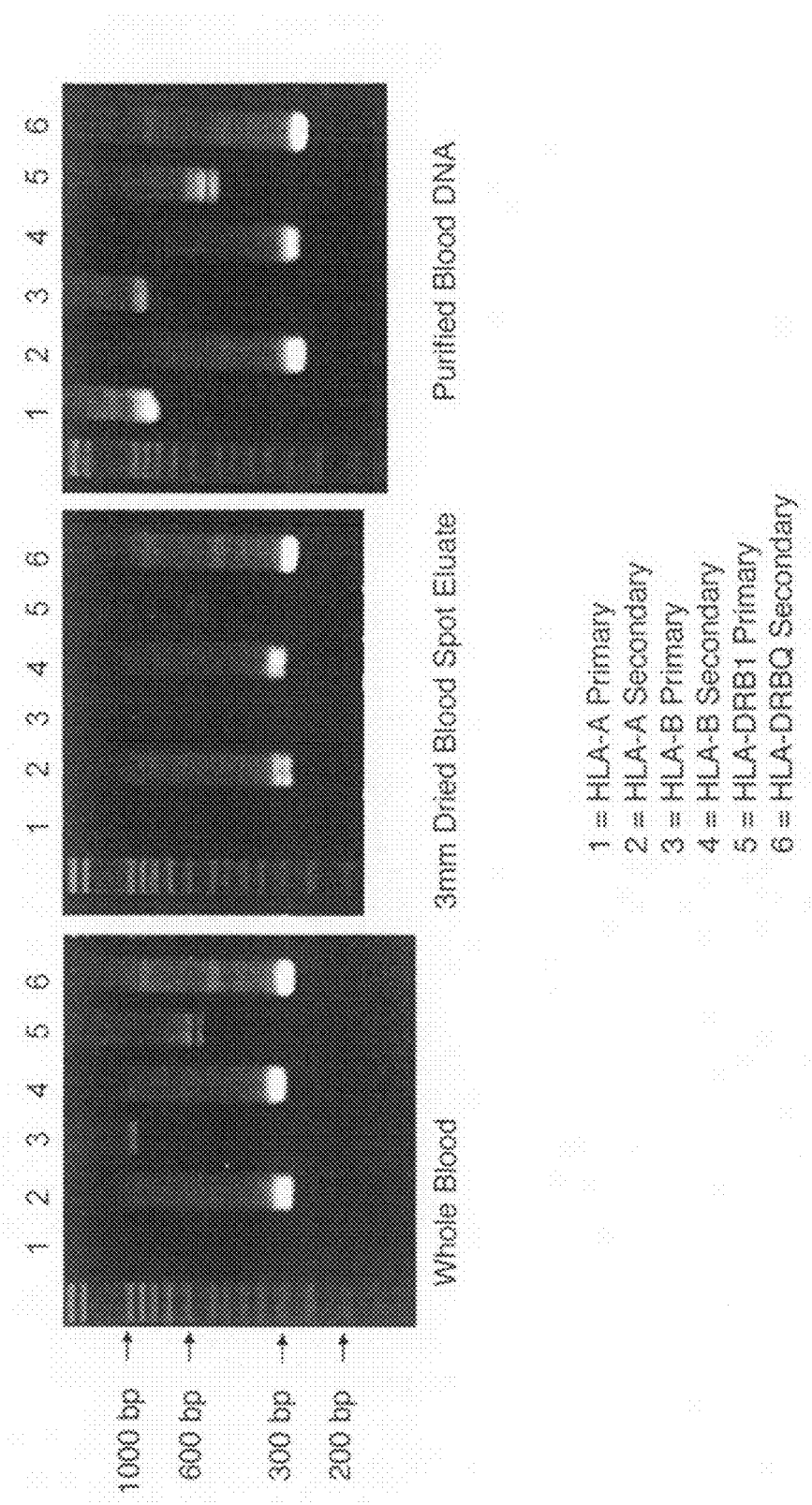

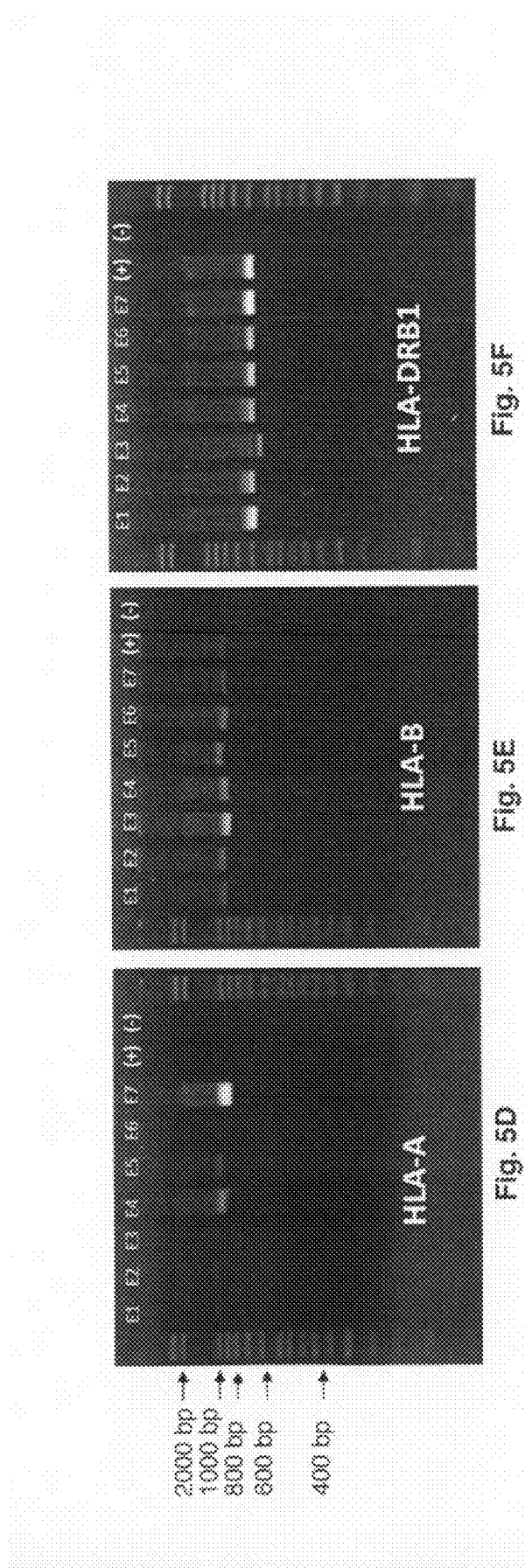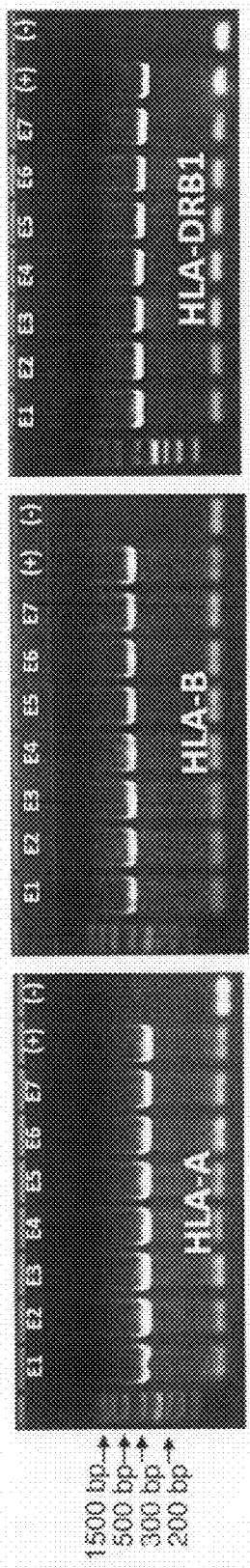

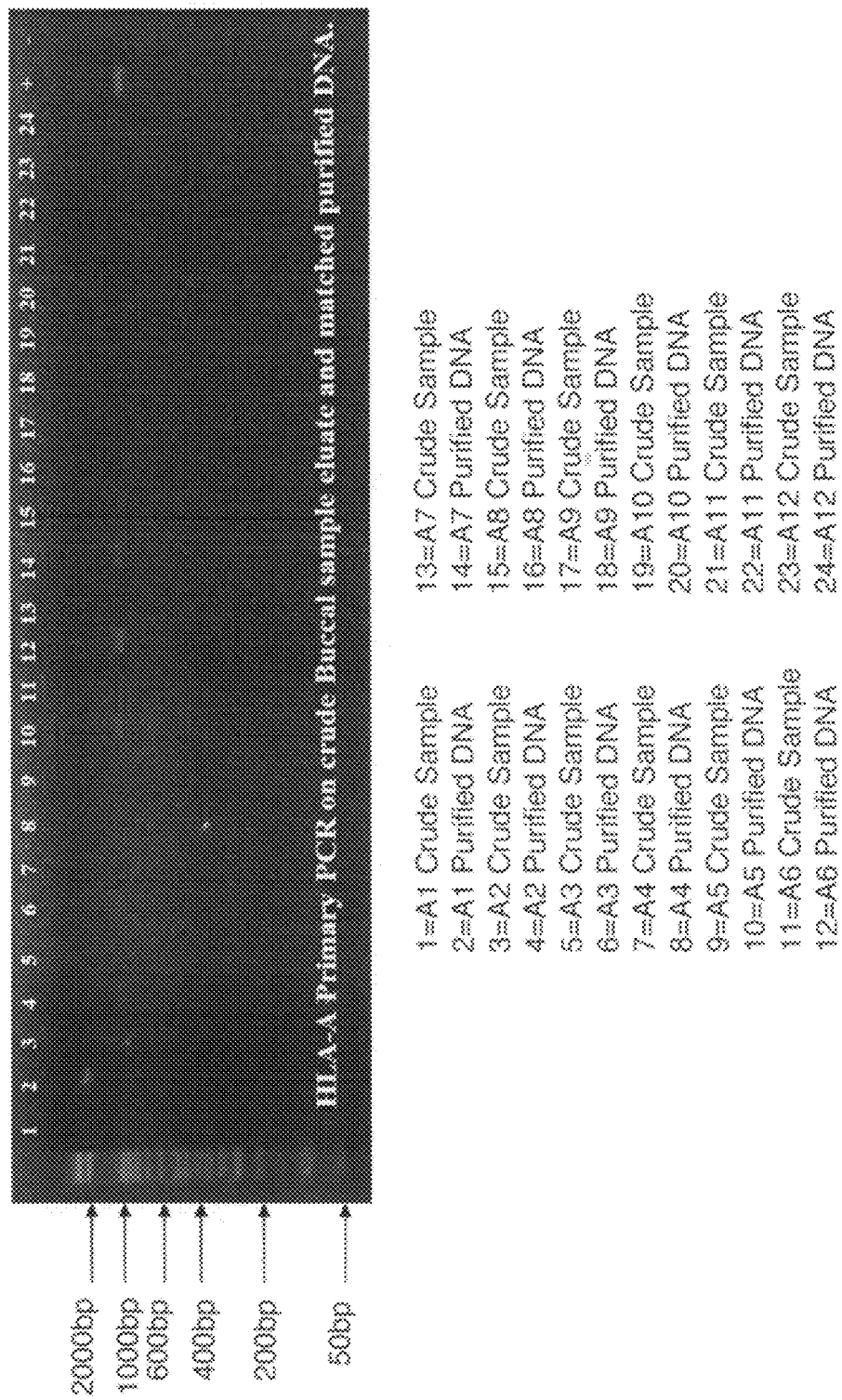

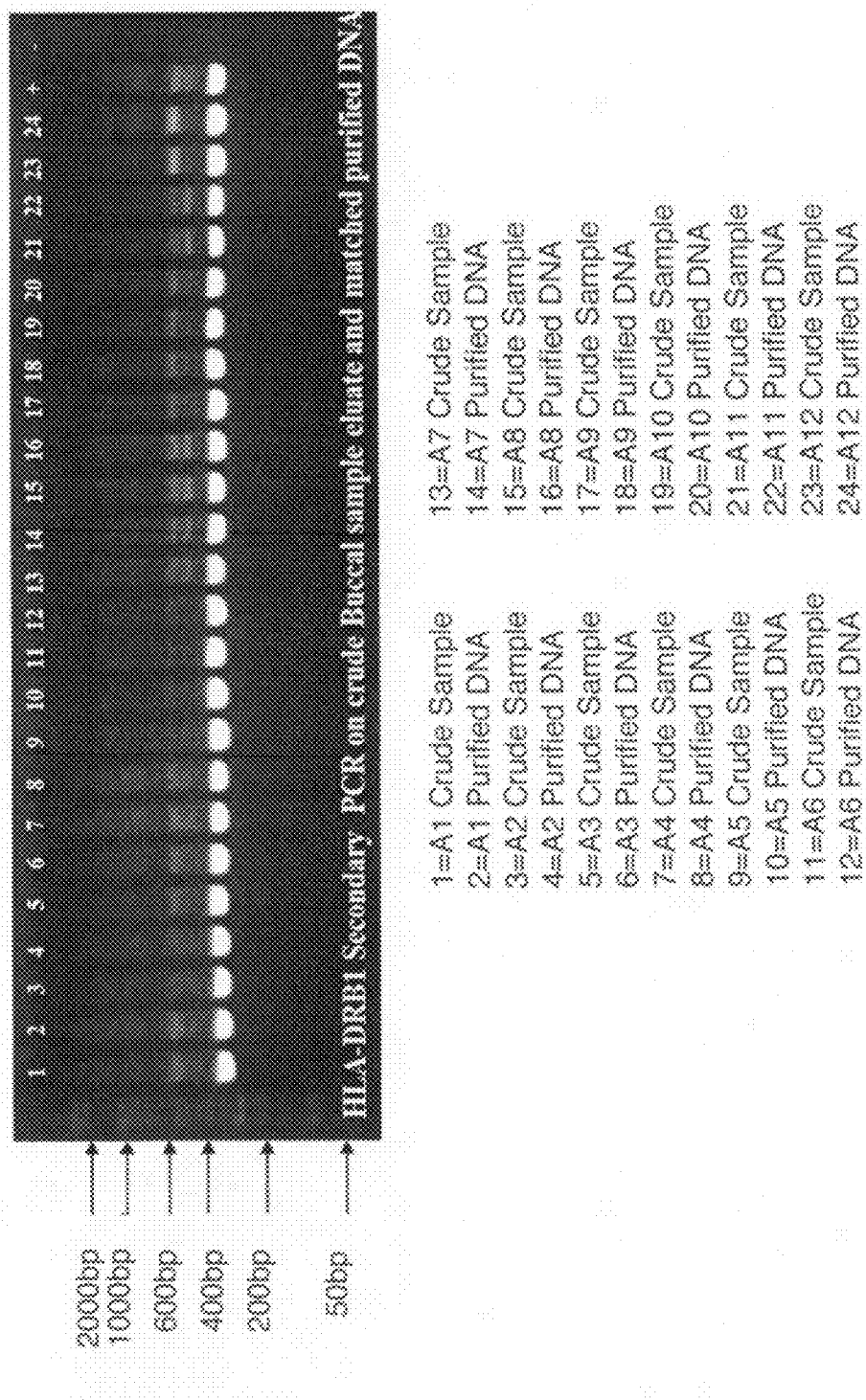

METHODS FOR PCR AND HLA TYPING USING UNPURIFIED SAMPLES

CROSS-REFERENCE TO RELATED APPLICATIONS

This is a continuation-in-part of pending application U.S. Ser. No. 12/924,301 filed Sep. 24, 2010, which claims benefit of priority under 35 U.S.C. §119(e) of provisional application U.S. Ser. No. 61/281,404, filed Nov. 16, 2009, the entirety of which is hereby incorporated by reference.

BACKGROUND OF THE INVENTION

1. Field of the Invention

The present invention relates to the fields of PCR and HLA-typing. More specifically, the present invention discloses methods and systems for a tandem PCR process to amplify DNA or RNA within a raw biological specimen and subsequent HLA-typing thereof on an individual or population scale in a field or medical office environment.

2. Description of the Related Art

There is a new and rapidly growing understanding of the medical significance of HLA typing in current medicine. Indeed, there is a very large range of diagnostic and public health applications for HLA-typing. Analysis of the HLA-Locus can be viewed as the historical prototype for the field of genetically personalized therapy (1). DNA-based HLA-Typing has been refined over the past decade into a very accurate companion genetic test for solid organ (2) and bone marrow transplantation therapy (3) and more recently as a companion genetic test for small molecule therapeutics, abacavir (4), lumiracoxib (5) and as genetic screening tests for auto-immune diseases: arthritis (6), celiac disease (7), T1D (8) and a possible screening test for vaccination responsiveness (9). For solid organ or marrow transplantation, high resolution HLA-Typing can be performed via multiple technologies: allele specific PCR (10), Luminex beads (11), Sanger sequencing (12), next generation sequencing (13).

Each of these technologies is accurate and specific enough to support the full range of follow-on HLA-Typing applications. However, the newer HLA-based applications each involve a patient base that is at least 100-times greater than defined by organ transplantation and entail medical treatments which are approximately 100-times less expensive than transplantation. Thus, in order to support the follow-on HLA-based application areas in a resource-limited medical screening environment, the current panel of HLA-Typing technologies must be reduced to tests which can be delivered in the clinic at a test cost in the $5-10 per gene range. Since DNA purification, DNA concentration determination and concentration adjustment comprise a major fraction of the labor and consumable cost associated with HLA-Typing, it would be desirable to develop methods to employ the least expensive of all DNA sources (mouthwash, cheek swabs or saliva) as the sample substrate in a way that bypasses DNA purification, DNA quantitation and DNA concentration adjustment prior to complex genetic testing.

At present, HLA typing requires the effort of an entire molecular genetics laboratory. Incoming blood specimens must first be purified by methods such as spin columns or magnetic beads, followed by quantitation of the purified DNA by methods such as PicoGreen fluorimetry or UV absorbance. The quantified DNA is then subjected to PCR amplification and, following PCR, is then analyzed by high throughput re-sequencing or, more recently, by multiplex hybridization analysis by beads or by microarrays. Thus, the resulting workflow requires the effort of a full molecular genetics laboratory, and at least one full day to compile the final HLA-typing data. The complexity of such a standard workflow also introduces major concerns related to chain-of-custody and the requirement for complex and costly LIMS systems and workflow standard operating procedures, to keep track of sample flow through the several processing and analysis workstations.

Efforts to streamline the process have included obviating DNA purification. Previous attempts to perform PCR amplification from unpurified blood have been problematic even with the availability of variants of the Taq polymerase used for standard PCR. The use of raw blood as a PCR substrate has not yielded consistent results due to the extreme sample-to-sample variation in the white cell complement of blood and possible sample-to-sample variation in the very large excess of blood solutes which can interfere with the underlying PCR reaction.

Mouthwash, cheek swabs and saliva constitute a robust and inexpensive way to collect human DNA for clinical genetics, personalized therapy, and for genetic epidemiology. However, the value of those inexpensive DNA sources is compromised, in part, by the cost and labor required to purify DNA from them, prior to genetic testing.

Thus, there is a recognized need in the art for low equipment and consumable cost, high-throughput methods of gene amplification and HLA typing. There is also a recognized need in the art for developing methods to employ inexpensive DNA sources as the sample substrate in a way that bypasses DNA purification, DNA quantitation and DNA concentration adjustment prior to complex genetic testing. Specifically, the related art is deficient in a hands-free or automated, real-time high-resolution method of HLA typing without a need for first externally purifying the DNA from a sample. The present invention fulfills this long-standing need and desire in the art.

SUMMARY OF THE INVENTION

The present invention is directed to a method for amplifying a DNA of interest. The method comprises obtaining a raw sample comprising DNA, performing a first PCR on the raw sample to produce a first amplicon and diluting the first amplicon. The method further comprises obtaining a raw umbilical cord blood, mouthwash, cheek swabs or saliva sample comprising DNA, performing a first PCR on said sample to produce a first amplicon and diluting the first amplicon. The method may further comprise obtaining a sample comprising DNA from a bacterium or a virus. A second PCR is performed thereon until all primers used in the second PCR reaction are consumed to produce a second amplicon, thereby amplifying the input sample DNA to a final amplified DNA product concentration that is limited by the primer concentration in the second PCR reaction, said second PCR reaction independent of the amount or purity of the DNA comprising the original sample.

The present invention is directed to a related invention where the first PCR is performed on a set of gene targets in parallel on the raw sample to produce the first set of amplicons and diluting the first set of amplicons. The present invention is further directed to a related invention where the first PCR is performed on a set of gene targets in parallel on the raw umbilical cord blood, mouthwash, cheek swabs or saliva sample to produce the first set of amplicons and diluting the first set of amplicons. The first PCR may also be performed on a set of gene targets in parallel on the sample from a bacterium or a virus. A second PCR is performed on the first set using the entire set of primary amplicon products as a set of templates for the second PCR reaction until all secondary PCR primers are consumed to produce a second amplicon set, thereby amplifying the DNA.

The present invention is directed to yet another related method where the DNA comprises one or more genes of interest and the method further comprises hybridizing the second amplicon to probes having sequences of allele variations associated with the gene of interest, detecting a fluorescence pattern from the hybridized amplicon and assigning an allelotype based on the fluorescence pattern. Hybridizing is performed on microarrays designed to analyze HLA genes or other gene sets of similar complexity and said microarrays are fluidically isolated by removable gaskets or by other types of hydrophobic barriers.

The present invention also is directed to a method for amplifying one or more RNAs of interest. The method comprises obtaining a raw biological sample from an individual, performing a first reverse transcription PCR on the raw biological sample to produce a first cDNA amplicon(s) and diluting the first amplicon(s) and performing a second PCR thereon until all primers are consumed to produce a second amplicon(s), thereby amplifying the RNA(s) of interest. The method further comprises obtaining a raw umbilical cord blood, mouthwash, cheek swabs or saliva sample, or cell culture media or a bacterial or viral sample comprising RNA, performing a first reverse transcription step on said RNA and then diluting said reverse-transcribed DNA sample as template into a first PCR reaction to produce a first amplicon.

Other and further objects, features, and advantages will be apparent from the following description of the presently preferred embodiments of the invention, which are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 2A-2B are gels showing Primary and Secondary HLA-A, HLA-B, and DRB1 PCR Amplicons generated from 2 μl of whole fluid blood (FIG. 2A) or 10 ng of purified human genomic DNA (FIG. 2B). Resolved on 2% Agarose SFR gel electrophoresis (Amresco 1×TBE gel). #1: HLA-A locus specific Primary PCR product (approx. 1,000 bp); #2: HLA-A exon 2 Secondary PCR Product (approx. 300 bp); #3: HLA-A exon 3 Secondary PCR Product (approx. 320 bp); #4: HLA-B locus specific Primary PCR product (approx. 1,000 bp); #5: HLA-B exon 2 Secondary PCR Product (approx. 320 bp); #6: HLA-B exon 3 Primary PCR product (approx. 310 bp); #7: DRB1 locus specific Primary PCR product (approx. 650 bp); #8: DRB1 exon 2 Secondary PCR Product (approx. 310 bp); L: Bio-Rad EZ Load ladder.

FIGS. 3A-3C are gels showing locus specific Primary PCR products generated from 12 un-purified whole blood templates for HLA-A (FIG. 3A), HLA-B (FIG. 3B), and HLA-DRB1 (FIG. 3C).

FIG. 5A-5C are gels showing HLA-A, HLA-B, and DRB1 PCR Primary PCR products then Secondary PCR Amplicon sets generated from 1 μl whole fluid blood (left) compared to the same reactions performed fluid derived by re-hydration of a 3 mm dried blood spot (middle) that had been re-hydrated as described in the protocol of Example 5, and the same reaction performed on 10 ng of purified DNA from the same blood specimen (right). FIGS. 5D-5F display the primary PCR reactions specific for HLA-A, HLA-B & HLA-DRB1 for these 8 unique raw blood samples obtained from anonymized volunteers, while FIGS. 5G-5I display the secondary PCR reactions specific for HLA-A, HLA-B & HLA-DRB1 for the same 8 raw blood samples. As can be seen, although the yield of primary PCR product is highly variable among the set of 8 raw blood samples (FIGS. 5D-5F) the subsequent secondary PCR reaction has generated a series of amplified exons which are nearly identical in yield and specificity, among the set of 8 raw blood specimens (FIGS. 5G-5I). Gels were resolved on 2% Agarose SFR (Amresco), 1×TBE gel. L: Bio-Rad EZ Load ladder. For both HLA-A and HLA-B, the secondary PCR product observed on the gel is an unresolved pair of bands, derived from multiplex (n=2) amplification of exon2 & exon3 in the same PCR reaction.

FIGS. 6A-6G show PCR reactions for HLA-typing from rehydrated buccal swabs. De-identified buccal swabs were procured from local donors. Four swabs were collected from each participant by vigorously swabbing up and down twenty times per each quadrant of the mouth and placed into 15 mL conical tubes. Whole mouth swabs were taken from 12 individuals: A1-A12. Samples were dried for 72 hours under laminar flow hood. Dried swabs were then rehydrated in 150 μl of rehydration buffer (100 mM Borate+1 mM EDTA) and solubilized at 70° C. for 2× hours. The resulting fluid phase was then mixed by pipetting. The rehydrated swabs were then stored at −20° C. until analysis. A nested (tandem) PCR reaction was then performed for each of the HLA loci of interest. 1 μl of raw swab eluate was used for a primary 25 μL PCR reaction employing Roche Taq polymerase'. The subsequent (secondary) PCR was then performed upon 2.5 μL of the primary amplicon product in a total PCR reaction volume of 50 μL, also employing Roche Taq polymerase. Upon completion, the residual sample (up to half the recovered volume) was extracted via QIAamp DNA Blood Mini Kit (Qiagen catalog #51104). The resulting purified DNA was run on the same microarray HLA-typing platform. Unpurified and purified buccal DNA were analyzed via microarray technology for HLA typing. The matched, de-identified DNA from buccal swabs was compared to HLA types obtained on the raw, unpurified samples via gel electrophoresis. 2.5 microliters of each of the resulting 2° PCR reaction product was then loaded onto a standard agarose gel. Primary locus specific PCR products as well as the products of the secondary exon specific reaction set (performed as a single multiplex reaction) were displayed in FIG. 6A (left) along with identical reaction products obtained from 10 ng of purified DNA obtained from the sample (right). Bands were visualized by Amresco EZ-Vision DNA Dye. As seen, the amount of final 2° amplicon obtained from 1 μL of raw swab eluate, is similar in specificity & mass yield, to the amplified HLA product obtained from 10 ng of purified DNA from the same sample. FIGS. 6B-6G display the product of the tandem PCR reactions performed on raw cheek swabs from a total of 12 donors. FIGS. 6B-6D display the primary PCR reactions specific for HLA-A, HLA-B & HLA-DRB1 for these 12 raw buccal swab samples, while FIGS. 6E-6G display the secondary PCR reactions specific for HLA-A, HLA-B & HLA-DRB1 for the sample 12 raw buccal swab samples. As can be seen, although the yield of primary PCR product is highly variable among the set of 12 raw, re-hydrated buccal swabs samples (FIGS. 6B-6D) the subsequent secondary PCR reaction has generated a series of amplified exons which are nearly identical in yield and specificity, among the set of 12 raw buccal swab specimens (FIGS. 6E-6G).

FIG. 7A diagrams the primary HLA-PCR where the locus-specific primers for the genes HLA-A and HLA-DRB1 were used to multiplex the primary PCR. A 1:100 dilution was performed on the product of the locus-specific PCR and 2 μl of the dilution were used in a set of secondary nested PCR that targets HLA-A exons 2 and 3 and for HLA-DRB1 exon 2. The first nested secondary PCR reaction amplified only HLA-A exons 2 and 3. A second PCR reaction was performed independently on the product of the primary multiplex PCR where only HLA-DRB1 exon 2 was amplified. The third independent secondary PCR reaction used the mentioned template from the primary multiplex reaction and amplified in multiplex format the exons 2 and 3 for HLA-A and exon 2 for HLA-DRB1. FIG. 7B displays the primary PCR reactions specific for HLA-A and HLA-DRB1 where the two genes were amplified simultaneously for 5 samples of 10 ng of human genomic purified DNA. Two different size bands are resolved in the gel corresponding to HLA-A at 1000 bp and HLA-DRB1 at approximately 650 bp. FIGS. 7C-7E display the secondary multiplex reactions performed after the first multiplex PCR of HLA-A plus HLA-DRB1 took place. FIG. 7C shows the exon-specific HLA-PCR for HLA-A exons 2 and 3. FIG. 7D displays the exon-specific HLA-PCR for HLA-DRB1 exons 2. Finally, FIG. 7E displays the amplification in parallel of HLA-A exons 2 and 3, and HLA-DRB1 exon 2 in the same exon specific HLA-PCR. The bands cannot be differentiated in the gel due to the similarity of amplicon size. The fragment size for HLA-A exons 2 and 3 is approximately 320 bp while HLA-DRB1 exon 2 is 310 bp long. Gels were resolved using 2% agarose gels, and visualized using Amresco EZ-Vision DNA Dye FIG. 7F displays genotyping data of 2 samples chosen from the UCLA Immunogenetics reference panel with known genotypes as disclosed on column labeled as UCLA. The green color on the tables corresponds to 100% match genotypes. The blue color represents genotyping data from GUSA matching at the serological level. White cells represents mismatched genotypes or false positive hybridization subjected to adjustment of thresholds in analysis software.

FIGS. 7G-7L show tandem PCR amplification of multiple HLA genes in parallel: HLA-A & HLA-DRB1. Locus-specific multiplex and exon specific multiplex HLA-PCR reactions were performed on a set of 5 samples retrieved from the UCLA Immunogenetics reference panel for HLA Class I. FIG. 7G diagrams the primary HLA-PCR where the locus-specific primers for the genes HLA-B and HLA-DRB1 were used to multiplex the primary PCR. A 1:100 dilution was performed on the product of the locus-specific PCR and 2 μl of the dilution were used in a set of secondary nested PCR that targets HLA-B exons 2 and 3 and for HLA-DRB1 exon 2. The first nested secondary PCR reaction amplified only HLA-B exons 2 and 3. A second PCR reaction was performed independently on the product of the primary multiplex PCR where only HLA-DRB1 exon 2 was amplified. The third independent secondary PCR reaction used the mentioned template from the primary multiplex reaction and amplified in multiplex format the exons 2 and 3 for HLA-B and exon 2 for HLA-DRB1. FIG. 7H displays the primary PCR reactions specific for HLA-B and HLA-DRB1 where the two genes were amplified simultaneously for 5 samples of 10 ng of human genomic purified DNA. Two different size bands are resolved in the gel corresponding to HLA-B at 1000 bp and HLA-DRB1 at approximately 650 bp. FIGS. 7I-7K display the secondary multiplex reactions performed after the first multiplex PCR of HLA-B plus HLA-DRB1 took place. FIG. 7I shows the exon-specific HLA-PCR for HLA-B exons 2 and 3. FIG. 7J displays the exon-specific HLA-PCR for HLA-DRB1 exons 2. Finally, FIG. 7K displays the amplification in parallel of HLA-B exons 2 and 3, and HLA-DRB1 exon 2 in the same exon specific HLA-PCR. The bands cannot be differentiated in the gel due to the similarity of amplicon size. The fragment size for HLA-B exons 2 and 3 is approximately 320 bp while HLA-DRB1 exon 2 is 310 bp long. Gels were resolved using 2% agarose gels, and visualized using Amresco EZ-Vision DNA Dye FIG. 7L displays genotyping data of 2 samples chosen from the UCLA Immunogenetics reference panel with known genotypes as disclosed on column labeled as UCLA. The green color on the tables corresponds to 100% match genotypes. The blue color represents genotyping data from Genomics USA matching at the serological level. White cells in the table represent mismatched genotypes or false positive hybridization subjected to adjustment of thresholds in analysis software.

Figure 8A:
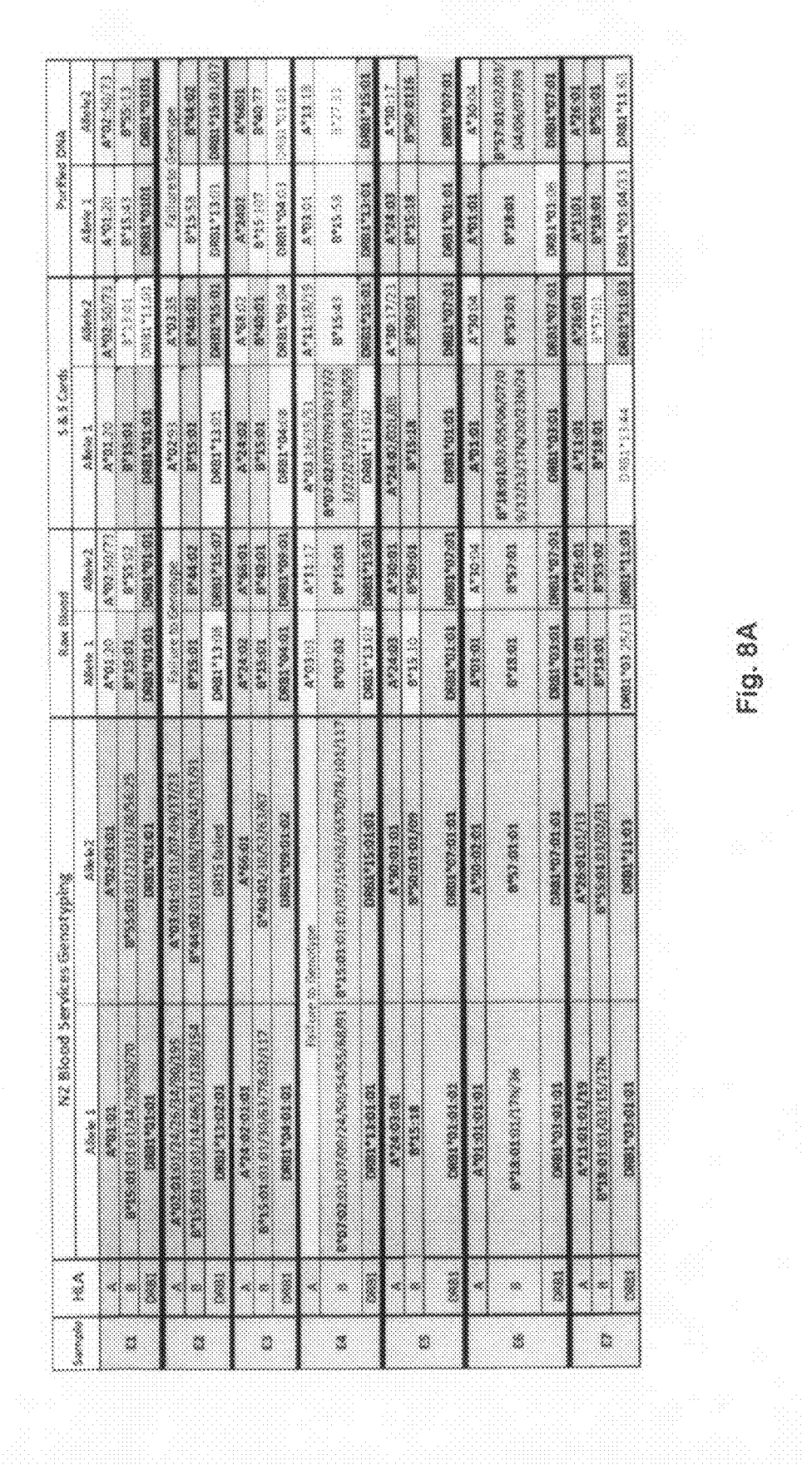
Figure 8B:
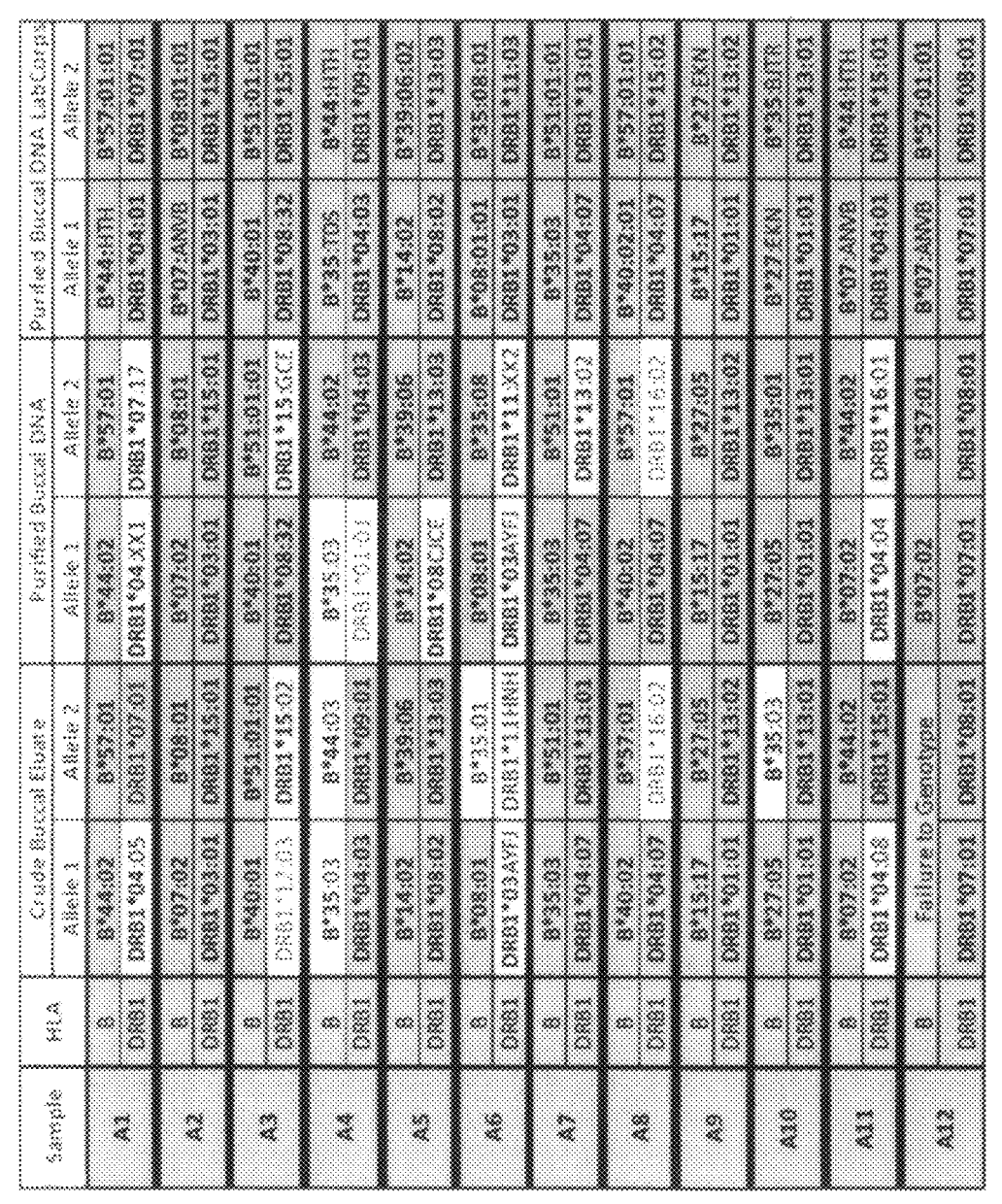

FIGS. 8A-8B are Tables showing HLA-typing obtained via microarray analysis for raw blood, dried blood spots (7A) and for raw buccal swabs and the corresponding DNA purified from those swabs (7B) obtained via the methods of Examples 5 & 6. Genotyping data obtained by analysis of raw blood, re-hydrated blood spots, and purified DNA of seven different blood samples collected in EDTA as the anticoagulant of choice was compared to genotyping data provided by New Zealand Blood Services for validation. The data shows overall agreement between results at serological level in most instances and high resolution in the remaining samples (FIG. 8A). FIG. 8B displays genotyping data of crude buccal sample eluate compared to the matching purified DNA and independent genotyping provided by Lab Corps. The data demonstrate a high level of agreement of the 11 samples collected locally. Green color demonstrate 100% agreement between Genomics USA genotyping and Lab Corps. The blue shaded data points represent agreement at the serological level, while white data points refer to failure to match the genotypes provided by the third party.

FIGS. 13A-13F correspond to HLA-A microarray data from A6.

FIGS. 14A-14F correspond to HLA-B microarray data from A6.

FIGS. 15A-15F correspond to HLA-$DRB_1$ microarray data from A6.

DETAILED DESCRIPTION OF THE INVENTION

Figure 1A:
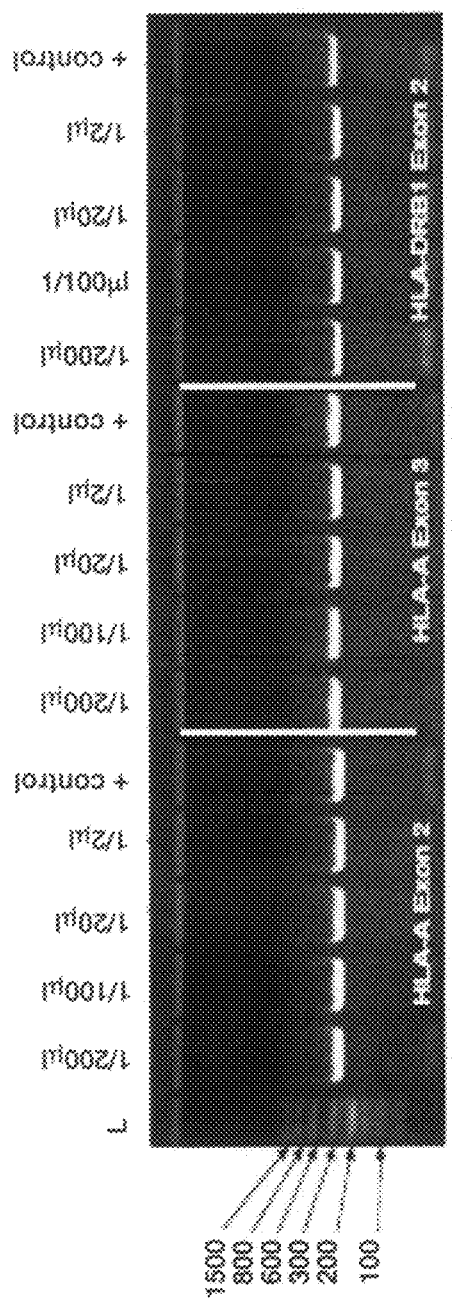
FIGS. 1A-1B are gels showing that, beginning with 10 ng of purified DNA, the amount of final Secondary PCR amplicon product is constant over a range of Primary PCR amplicon concentrations used as template for the Secondary PCR amplification: for the HLA-A exon set 2 or 3 and HLA-DRB1 exon 2 (FIG. 1A) and the HLA-B exon set 2 or 3 (FIG. 1B).

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the terms "individual" or "population" refers to donors or potential donors of the biological specimen, for example, raw blood, used in the amplification and HLA-typing methods described herein.

As used herein, the terms "raw sample" or "raw biological sample" refer to an unprocessed or unpurified sample, with the exception of those steps required to rehydrate the raw sample if it is or has been dried, that is used for a first amplification as described herein.

In one embodiment of the present invention there is provided a method for amplifying a DNA of interest, comprising obtaining a raw sample comprising DNA; performing a first PCR on the raw sample to produce a first amplicon; diluting the first amplicon; and performing a second PCR thereon until all primers used in the second PCR reaction are consumed to produce a second amplicon, thereby amplifying the input sample DNA to a final amplified DNA product concentration that is limited by the primer concentration in the second PCR reaction, said second PCR reaction independent of the amount or purity of the DNA comprising the original sample.

Further to this embodiment the method may comprise labeling the second PCR primer with one or more fluorophores. An example of a fluorophore is a cyanine dye. In another further embodiment the method may comprise sequencing the second amplicon for an analysis thereof. In this further embodiment analysis may determine one or more of identity, paternity of an individual, forensic information, tissue matching, risk factors for the development of disease, or response to medication.

In another embodiment of the present invention there is provided a method for amplifying a DNA of interest, comprising obtaining a sample of interest such as including but not limited to a raw umbilical cord blood sample, a sample mouthwash obtained from the individual's mouth, a cheek swab sample or a saliva sample, viral or bacterial sample comprising DNA; performing a first PCR on said sample to produce a first amplicon; diluting the first amplicon; and performing a second PCR thereon until all primers used in the second PCR reaction are consumed to produce a second amplicon, thereby amplifying the input sample DNA to a final amplified DNA product concentration that is limited by the primer concentration in the second PCR reaction, said second PCR reaction independent of the amount or purity of the DNA comprising the original sample.

In one aspect of all embodiments the method may comprise performing the first PCR on a set of gene targets in parallel on the raw sample to produce a first set of amplicons; diluting the first set of amplicons; and performing a second PCR thereon, using the entire set of primary amplicon products as a set of templates for the second PCR reaction until all secondary PCR primers are consumed to produce a second amplicon set, thereby amplifying the DNA. In this aspect less than 5 gene targets, less than 10 gene targets or less than 20 gene targets may be amplified in parallel. Also, the gene targets may be HLA-DRB1, DQ-A1 and DQB1. may be DQ-A1 and DQ-B1 or may be HLA-B and KIR. Also, the gene targets are two hypervariable regions near the mitochondrial origin of replication and one or more additional mitochondrial genes. In addition the gene targets may be segments of microbe-specific microbial 16S DNA genes such that the method detects microbes in the raw samples.

In another aspect of all embodiments the method may comprise performing the first PCR on a set of gene targets in parallel on the raw umbilical cord blood sample, mouthwash sample, cheek swab sample, saliva sample, viral or bacterial sample to produce a first set of amplicons with subsequent dilution and performing the second PCR thereon, as described supra.

In another aspect of all embodiments the DNA comprises one or more genes of interest and the method may further comprise hybridizing the second amplicon to probes having sequences of allele variations associated with the gene of interest; detecting a fluorescence pattern from the hybridized amplicon; and assigning an allelotype based on the fluorescence pattern. The gene(s) of interest may be an HLA-A gene, an HLA-B gene, an HLA-DRB1 gene, an HLA-DQA1 gene, or an HLA-DQB1 gene. In the case of the HLA genes, hybridizing may be performed on HLA-Chips containing microarrays, and said microarrays are fluidically isolated by removable gaskets or functionally-similar hydrophobic barriers. In another aspect of these embodiments the method may further comprise sequencing the second amplicon(s) for an analysis thereof, and analyzing the sequencing data using the Ricimer allele calling algorithm. In this aspect analysis may determine the type of viral or bacterial contamination. In this aspect analysis may also determine one or more of identity, paternity of an individual, forensic information, tissue matching, risk factors for the development of disease, or response to medication.

In all embodiments the primers for the first PCR may be locus-specific primers. Examples of locus-specific primers may have sequences shown in SEQ ID NOS: 1-14. Also, in all embodiments the primers for the second PCR reaction target DNA sequences may be contained within the amplified product of the first PCR reaction. In one aspect, the primers for the second PCR reaction may be a set of multiple exon-specific primers. Particularly, exon-specific primers may have sequences shown in SEQ ID NOS: 15-27. Furthermore, the raw sample may be fresh or rehydrated and comprises unprocessed fluid blood, dried unprocessed blood, a fresh buccal swab sample, a dried buccal swab sample, fecal material sample, a vaginal sample or a sample obtained by swabbing an animate or inanimate surface or object. Further still in all embodiments the DNA may be mitochondrial DNA.

In all embodiments the method for amplifying a DNA of interest may comprise obtaining said sample, which comprises the step of contacting said sample on Guthrie card and rehydrating said sample. The Guthrie card may contain fluidically isolated rings, wherein the rings are outlined with hydrophobic paint. A representative example of a saliva sample is an ORAGENE™-stabilized sample.

In another embodiment of the present invention there is provided a method for amplifying one or more RNAs of interest, comprising obtaining a raw biological sample from an individual; performing a first reverse transcription reaction on the raw biological sample to produce a first cDNA product; diluting the first cDNA product(s) to form the template in a first PCR reaction and performing a PCR reaction thereon until all primers are consumed to produce PCR amplicon(s), thereby amplifying the RNA(s) of interest.

Further to this embodiment the method comprises labeling the second PCR primers with one or more fluorophores. An example of a fluorophore is a cyanine dye. In both embodiments the raw biological sample may be fresh or rehydrated and comprises blood, a buccal sample, or a vaginal sample or other sample obtained by swabbing an animate surface or object.

In yet another embodiment of the present invention there is provided a method for amplifying one or more RNAs of interest, comprising obtaining a raw umbilical cord blood sample from an individual, a sample of mouthwash expelled from said individual, cheek swabs from said individual, a saliva sample from said individual, a sample from a bacterium or a virus; performing a first reverse transcription reaction on the raw biological sample to produce a first cDNA product; diluting the first cDNA product(s) to form the template in a first PCR reaction and performing a PCR reaction thereon until all primers are consumed to produce PCR amplicon(s), thereby amplifying the RNA(s) of interest.

In one aspect of these embodiments the method may comprise hybridizing the second amplicon or set of amplicons to probes having sequences complementary to an area of interest in a gene sequence; detecting a fluorescence pattern from the hybridized amplicon; and identifying one or more genes or allelotypes thereof based on the fluorescence pattern. Examples of a gene are one or more of an HLA-A gene, an HLA-B gene, an HLA-DRB1 gene, an HLA DQA1 gene, an HLA DQB1 gene or a KIR gene. In the case of HLA genes, hybridizing may be performed on HLA-Chips containing microarrays, and said microarrays may be fluidically isolated by removable gaskets. In another aspect of these embodiments the method may further comprise sequencing the second amplicon(s) for an analysis thereof, and analyzing the sequencing data using the Ricimer allele calling algorithm. In this aspect analysis may determine the type of viral or bacterial contamination. In this aspect analysis may also determine one or more of identity, paternity of an individual, forensic information, tissue matching, risk factors for the development of disease, or response to medication.

In all embodiments the second PCR may be linear PCR and the second amplicon(s) are cRNA(s). Alternatively, the second PCR may be real time PCR and the primers are exon specific to the first cDNA amplicon(s). In addition, the first amplicon(s) are one or more of an HLA-A, an HLA-B or an HLA-DBR1, an HLA-DQA1, or an HLA-DQ-B1 cDNA(s) and the exon-specific primers have a sequence shown in SEQ ID NOS: 15-27. Furthermore the raw sample may be as described supra.

In yet another embodiment of the present invention there is provided a method for allelotyping a gene of interest, comprising obtaining a raw biological sample from one or more individuals; performing a first PCR on the raw biological sample using primers specific to the gene locus or a defined set of gene loci to produce a first amplicon or first set of amplicons; diluting the first amplicon or first set of amplicons and performing a second PCR with the amplicon(s) serving as the template for the second PCR reaction using primers specific to an exon or a set of exons within the gene locus until all primers are consumed to produce an amplicon set from the second PCR reaction; hybridizing the second amplicon or amplicon set to probes having sequences of allele variations associated with the gene or gene set of interest; detecting a signal from the hybridized amplicon or amplicon set; and assigning an allelotype based on the detected hybridization signal. In an aspect of this embodiment the first amplicon or amplicon set may be cDNA amplified from RNA comprising the sample and the second PCR is linear PCR or real time PCR performed thereon.

In yet another embodiment of the present invention there is provided a method for allelotyping a gene of interest, comprising obtaining a raw umbilical cord blood sample, mouthwash sample, cheek swab sample or saliva sample from one or more individuals, viral or bacterial sample; performing a first PCR on said sample using primers specific to the gene locus or a defined set of gene loci to produce a first amplicon or first set of amplicons; diluting the first amplicon or first set of amplicons and performing a second PCR as described supra.

In all these embodiments the detectable signal may be fluorescence where the second PCR primer pairs are labeled with one or more fluorophores. An example of a fluorophore is a cyanine dye. Also, the first and second PCR primer sequences, the gene of interest, the raw biological sample and the raw umbilical cord blood sample, mouthwash sample, cheek swab sample or saliva sample, viral or bacterial sample may be as described supra. In addition the individuals may comprise a population in a field environment.

Provided herein are methods and systems for individual or population-scale amplification and HLA-typing of DNA or RNA using a raw specimen. For example, although not limited to, microfabricated devices or "Lab-on-a-Chip" (LoC) devices provide high value, clinically relevant applications in diagnostics or public health. Implementing the instant methods and systems enables a rapid, miniaturized point-of-collection analysis of DNA or RNA that significantly lowers costs in equipment and consumables. Particularly, the methods and systems provided herein allow the user to completely bypass DNA purification and subsequent DNA quantitation prior to HLA-typing.

HLA-Chip layout is presented in a 16 array/slide format. Sixteen identical microarrays are separated, fluidically, by a removable gasket or by a functionally equivalent hydrophobic barrier.

Thus, the present invention provides a method of DNA or RNA amplification from a raw biological specimen. The specimen may be, but not limited to, blood, such as is obtained from a finger prick on one or more individuals or heel prick on neonates and older infants. The specimen may be used immediately in droplet form for amplification or dried onto a card, e.g., a Guthrie card, for subsequent re-hydration, followed by amplification or other processing. The methods for obtaining a blood sample or drop, as well as drying, storing and rehydrating a blood drop, are well-known and standard in the art. The quantity of raw blood or rehydrated dried blood useful for amplification is about 1-2 microliters. The raw blood samples may be collected from a single individual or from a population. Collection of samples may be performed in the field, at a diagnostic laboratory or in a clinic or doctor's office. Amplification of DNA and subsequent HLA-typing using the amplicon may be performed in real-time at the point of collection.

The specimen may also be, but not limited to, epithelial cells, such as is obtained from a cheek swab with a Q-tip on one or more adults or neonates or older infants. The specimen may be used immediately as a wet swab for amplification or air-dried for subsequent re-hydration, followed by amplification or other processing. The methods for obtaining a swab sample, as well as drying, storing and rehydrating a swab sample are well-known and standard in the art. The quantity of raw moist swab material or rehydrated dried swab material useful for amplification is about 1-2 microliters. The raw swab samples may be collected from a single individual or from a population. Collection of samples may be performed in the field, at a diagnostic laboratory or in a clinic or doctor's office. Amplification of DNA and subsequent HLA-typing using the amplicon may be performed in real-time at the point of collection or upon shipping to a regional laboratory.

The enriched umbilical cord blood specimens may be collected, stabilized and recovered by transfer to Guthrie card, air drying, then recovered by rehydration. Up to 16 umbilical cord blood specimens may be collected per 1"×3" paper Guthrie card. In some instances, 2 mm cylindrical sample elements are fluidically isolated in the Guthrie card by embossing 4 mm rings into the paper with a hydrophobic paint, and backing the card with plastic.

PCR amplification of DNA on such fluidically-isolated specimens on Guthrie Cards is performed on the collected raw specimen without having to first purify the DNA: using highly gene- or locus-specific primers, as is currently done via well-known and standard methods. Examples of locus specific primers have the sequences shown in SEQ ID NOS: 1-14. Tandem PCRs (PCR #1, the PCR #2) are run such that the first PCR reaction occurs on the raw specimen, such as blood, or rehydrated dried blood spots, rehydrated raw swab eluate or a fecal sample. It is known that because of uncontrolled contamination of the specimen with PCR inhibitors in the blood or swab material, the yield of the primary PCR reaction can vary significantly. This has been responsible for the general failure of such raw blood or raw swab PCR in a commercial setting.

However, in the present invention, the second PCR reaction occurs using the product of the first PCR reaction with a subset or sub-sequence of locus-specific primers, such as, but not limited to, exon-specific primers. Examples of exon specific primers have the sequences shown in SEQ ID NOS: 15-27. Because the second PCR reaction is set up to be primer-limited, that is, the second PCR reaction intentionally proceeds until all added PCR primer oligonucleotides are consumed, the amount of PCR product derived from the second PCR reaction becomes independent of the variable amount of product obtained in the first PCR reaction. Consequently, the significant variation in the yield of the first PCR reaction due to uncontrolled contamination from within the raw blood specimen, is corrected by the self-limiting nature of the second reaction. Moreover, the product of the first PCR reaction is significantly diluted into the second PCR reaction, thus minimizing the effect of PCR inhibitors that had contaminated the raw specimen at the outset. The net result is a predetermined amount of final PCR product always being obtained via the use of this series of two PCR reactions, i.e., the amount of final product always will be determined by the amount of PCR primer used in the second of the two PCR reactions. Moreover, via significant dilution of the primary PCR reaction into the second PCR reaction, the overall tandem PCR reaction is thus substantially independent of uncontrolled variations in PCR inhibitor contamination within the original raw sample.

RNA amplification may be accomplished using the tandem PCR methods described herein. As with DNA amplification, a raw blood sample, either fresh or a rehydrated dry sample is obtained and a reverse transcription (RT) reaction is performed followed by PCR, e.g., real time PCR, endpoint PCR or linear cRNA amplification or synthesis.

The amplicon, which may be, but not limited to, an amplified human leukocyte antigen gene HLA-A, HLA-B or HLA-DRB1 or DQA1 or DQB1 gene or the HLA receptor KIR, is hybridized to a microarray or chip comprising panels of overlapping probes spanning a region of interest within one or more exons in the gene, such as an allele variation as in a single nucleotide polymorphism. The exon-specific primers may be labeled with a moiety or dye that produce a detectable signal. For example, with fluorophore-labeled primers, e.g., with a cyanine dye such as Cy3 or Cy5, which are exon specific. Hybridized amplicon-probe pairs can therefore be detected and hybridization patterns associated with an allelotype. A representative microarray design is disclosed in U.S. Pat. No. 7,354,710 and U.S. Publication Nos. 20070298425 and 20090011949, hereby incorporated by reference. Also, for example, U.S. Publication No. 20070298425 discloses HLA primers to amplify HLA-A, HLA-B and HLA-DRB1 genes and HLA probe sequences accounting for allele variations in the HLA-A, HLA-B and HLA-DRB1 genes suitable for site-specific hybridization.

Alternatively, a nucleic acid sequence or length analysis may be performed on the second DNA or RNA amplicon using standard and known procedures, such as, but not limited to pyrosequencing. Such analysis is useful to obtain HLA types, or to obtain the identity and/or paternity of an individual. For example, length dependent analysis of nucleic acids is the basis for most current human identification via the short terminal repeat (STR)-based identifier reaction. Also, sequence or length analysis may provide useful forensic information from samples obtained at, for example, a crime scene. Furthermore, the tandem PCR reactions described herein may be performed on mitochondrial DNA for the purposes of human identification. Using mitochondrial DNA may be particularly useful when the sample is compromised, such as very small or degraded, because of its increased copy number. The tandem PCR methods provided herein are useful when the sample mitochondrial DNA comprises two hypervariable regions near the mitochondrial origin of replication and one or more additional mitochondrial genes. In addition, the tandem PCR reactions described herein may be performed on genes or gene sets other than HLA or KIR or mitochondrial DNA, particularly gene set analysis for the purposes of assessing disease risk or response to medication. Furthermore, the tandem PCR reactions may be performed on segments of microbe-specific microbial 16S DNA genes. Because microbial 16S DNA genes differ among microbes, the methods described herein are useful for detecting microbes present in the raw samples, for example, fecal matter.

Additionally, the instant methods are not limited to raw blood as the sample source. Most particularly, the methods can be used to process DNA- or RNA-containing specimens obtained by swabbing the inside of the mouth or the vaginal area, or a skin surface or other surfaces or objects. Furthermore, the swabbed surfaces or objects may be inanimate and the obtained sample may be processed via the instant methods to obtain evidence at a crime scene.

If the sample is fluid, as from a mouth or buccal swab, the resulting sample can be used directly, by squeezing the fluid from the swab, without DNA purification, to support tandem PCR or tandem RT-then-PCR as described herein. As with dried blood on paper cards, if the swab-containing sample is dry, or became dry after air-drying, it may be rehydrated and then, the resulting re-hydrated swab sample may be used, also without nucleic acid purification, to support the instant methods described herein.

The PCR amplification methods provided herein may be designed for performance on a system comprising a Laboratory on a Chip (LoC), for example, but not limited to, an HLA. The HLA-LoC replaces the entire workflow required for current, standard and well-known HLA-typing protocols with a single integrated workstation that requires only one technician for operation. A single technician needs only to load pre-fabricated chips and reagents into the workstation and to pipette the input blood specimens into the chip. Also, if necessary, one technician can tend to several stations in parallel. A hands-off duty cycle from sample loading to final HLA-type is less than 1 hour per specimen. The HLA-LoC is suitable for use in a doctor's office on an individual basis or field clinic among a population. In addition it is contemplated that with automation the HLA-Loc could become the standard for all HLA-typing labs.

A tandem PCR method provided herein accepts raw, completely unpurified mouthwash, cheek swabs and ORAGENE™-stabilized saliva or other DNA containing samples as the sample input, the resulting amplicons serving as the substrate for complex, microarray-based genetic testing. As a model for such "raw sample genotyping", microarray-based analysis of 3 genes within the HLA locus [HLA-A, HLA-B, HLA-DRB1] was used due to their well-known genetic complexity and because analysis of this 3-gene triplet comprises the core genetic test for solid organ, marrow and other types of stem cell transplantation: applications which might benefit from this sort of simplified approach to sample collection and processing.

A new way to use microarrays for HLA-typing based on purified DNA and also the corresponding raw sample as the analyte is demonstrated herein. This new approach to raw sample genotyping relies on tandem PCR amplification of the DNA-containing sample: that is, a primary (1°) PCR reaction is performed on a raw sample, even if the yield of the primary PCR amplicon were to vary wildly as a function of endogenous PCR inhibitors or its DNA content, if a small fraction of the amplicon product is diluted 10-100-fold into a secondary PCR reaction, then the offending inhibitors would be diluted-out and the secondary reaction would proceed as if the sample had been purified. The subsequent secondary PCR reaction is then performed under conditions that are primer limiting: that is, where the reaction proceeds until all secondary PCR primers are consumed.

By combining those two attributes [the use of raw sample in the 1° PCR+a primer-limited 2° PCR reaction] one can determine if raw orally-derived samples can be used directly for A, B & DRB1 allelotyping, in a way that produces a predetermined final 2° amplicon concentration, thereby obviating both DNA purification & DNA quantitation in the sample preparation workflow.

Thus, an HLA-typing system comprises means for running tandem PCR, such as a PCR module, an HLA-LoC chip, a microarray platform for hybridization which includes a microarray reader and software for digitizing and analyzing hybridization data. The system also comprises the necessary processors and memory and storage components as required to operate the system and as are known and standard in the art. It is contemplated that all of the sample processing steps are automated in a simple cartridge format. Particularly, and without being limiting, the two analytical instruments comprising the system, i.e., the PCR module and microarray reader are integrated into one inexpensive device, using a modular architecture approach. With the modular approach this system can be optimized to meet various throughput requirements from those occurring at point-of-collection in a doctor's office or field clinic or, at the other extreme, those occurring in a centralized laboratory, such as in an ASHI-certified tissue typing laboratory.

The instant methods of HLA typing or analysis of other genes is not limited to Lab on a Chip applications. Via similar application of the instant tandem PCR methods, or the related application of tandem RT-then-PCR methods, the instant methods may also be used to enable HLA-typing without nucleic acid purification for batchwise processing (in a non Lab on a Chip format) as would be performed if the tandem reactions were performed in lots of 96 reactions in parallel, to be followed by analysis of the resulting secondary PCR amplicon by microarrays, or other methods of genetic analysis that could be performed in parallel.

It is contemplated that PCR #1+PCR #2 methods and systems may be used for other PCR-based genetic tests to replace the standard DNA purification+DNA quantitation+PCR steps. Also, it is contemplated that the method of HLA-typing provided herein is useful for other medical or health applications. For example, HLA-typing is required for solid organ transplantation and bone marrow and stem cell transplantation. In addition, the instant methods of HLA-typing may be useful for public health applications, such as, but not limited to, personalized vaccination responsiveness, HLA-based variation in infectious disease risk and HLA-based sensitivity to autoimmune diseases. Furthermore, it is contemplated that a purification free RNA analysis is useful as a diagnostic tool for early stage sepsis, or adverse drug reaction (ADR) using raw blood lymphocyte RNA expression as the analyte set of interest.

It is demonstrated in the study of twelve volunteers, referred to as A1-A12, that this tandem PCR method amplifies A, B and DRB1 from raw mouthwash, raw cheek swab fluid and from raw ORAGENE™-stabilized saliva in a way that standardizes the amount of the resulting PCR product: generating a fixed DNA yield that is determined by the PCR reaction conditions themselves, rather than by the amount of DNA in the sample, or its purity. It is demonstrated that for A, B & DRB1, those self-limiting PCR reactions produce a PCR product that can be used, as-is, for HLA-Typing via microarray technology. It is shown for all twelve volunteers, that the resulting microarray data obtained from the three classes of raw sample are very similar, in a statistical sense, to that obtained from the corresponding matched purified DNA and that, upon subsequent analysis to yield HLA-Types from the microarray data, high resolution HLA allelotype calls are obtained for all twelve volunteers and were found to be similar for all sample type variants to the corresponding HLA-Type obtained on purified DNA, with standardized HLA-Typing methods, performed in an ASHI-certified national tissue-typing laboratory.

It is contemplated that a more extensive, multiple laboratory validation of "raw sample HLA-Typing" may be warranted, as a low-cost way to obtain HLA-Typing data to support large-scale applications such as bone marrow and stem cell banking or public health screening applications, also based on HLA-Typing, that are now widely discussed: including the heritable component of infection responsiveness, personalized vaccine responsiveness, the heritable risk of autoimmunity and companion testing for adverse drug reaction.

Generally, HLA-typing may be viewed as the prototype for the broader field of complex, regulated genotyping. Based on the preliminary agreement seen here between HLA-types obtained from raw vs. purified DNA samples, it is useful to consider the possibility that such raw sample genotyping might be applied to other complex genetic test panels, and technologies other than microarrays: thus bypassing DNA purification in support of a broader range of simplified genetic screening.

The following examples are given for the purpose of illustrating various embodiments of the invention and are not meant to limit the present invention. One skilled in the art will appreciate that the present invention is well adapted to carry out the objects and obtain the ends and advantages mentioned, as well as those ends and advantages inherent herein. Changes therein and other uses which are encompassed within the spirit of the invention as defined by the scope of the claims will occur to those skilled in the art.

EXAMPLE 1

Tandem PCR Yields Constant 2° Product Over Wide 1° Input Amounts

Figure 1B:
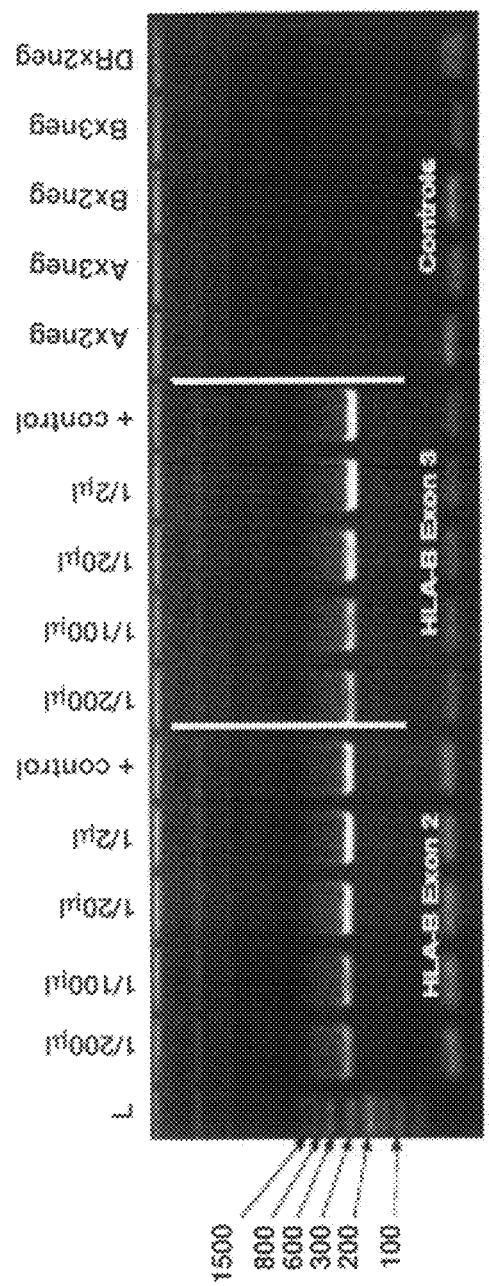

2 µl of raw blood was used as the template for the primary, locus-specific HLA PCR reactions required for HLA-Chip analysis. Amplification was performed via the Finnzymes PHUSION® Blood Direct kit. Different amounts of that primary, locus specific PCR product were then diluted in H2O and used as template for the secondary, self limiting, exon-specific PCR reactions. One microliter of each of the resulting 2° PCR reaction product was then loaded onto a standard acrylamide gel. HLA-A exons 2 and 3 and HLA-DRB1 exon 2 (FIG. 1A) and HLA-B exons 2 and 3 (FIG. 1B) were visualized by Amresco EZ-Vision DNA Dye. Positive controls on the gel refer to the product of the same tandem HLA PCR reactions, but instead using 10 ng of highly-purified Roche DNA as the original sample input. As seen, the amount of final 2° amplicon obtained from 2 µl of raw blood, is nearly independent of the amount of 1° amplicon used in the reaction, and similar in specificity & mass yield, to the amplified HLA product obtained from 10 ng of purified Roche DNA.

EXAMPLE 2

Generation of HLA Locus-specific Amplicons

HLA locus-specific amplicons are generated from 2 µl whole fluid blood (FIG. 2A) via the PCR reaction using the PHUSION BLOOD DIRECT® kit commercially available from Finnzymes (Woburn, Mass.). Reaction conditions are as follows: 1× PHUSION® Blood PCR Buffer, 0.8 µl PHUSION® Blood DNA Polymerase, 1.75 mM EDTA, 400 nM each primer in a 20 µl reaction volume. Reactions are cycled using the following protocol: initial denaturing at 98° C. for 5 minutes followed by 35 cycles of i) denature at 98° C. for 5 seconds, ii) anneal at 70° C. for 5 seconds, and iii) extend at 72° C. for 30 seconds, and one final extension at 72° C. for 1 minute.

When amplifying HLA loci from purified DNA (FIG. 2B), 10 ng of genomic DNA is used as template for PCR using Roche (Basel, Switzerland) FastStart Taq DNA Polymerase under the following conditions: 1×PCR Buffer (without $Mg^{++}$), 1.5 mM $MgCl_2$, 0.16 mg/ml BSA (fraction V), 0.05 µM each dNTP, 400 nM each primer, and 1 unit of Taq in a total reaction volume of 25 µl. These reactions are cycled using the following protocol: initial denaturing at 98° C. for 5 minutes followed by 35 cycles of i) denature at 98° C. for 5 sec, ii) anneal at 70° C. for 1 minute, and iii) extend at 72° C. for 30 sec, then a final 72° C. extension for 7 minutes.

HLA Locus Specific Primary PCR Primer Sequences
HLA-A locus primary primer pair:

```
Forward primer 1:
                                        (SEQ ID NO: 1)
5'- GCC TCT GYG GGG AGA AGC AA -3'

Reverse primer 1:
                                        (SEQ ID NO: 2)
5'- GTC CCA ATT GTC TCC CCT CCT T -3'
```

HLA-B locus primary primer pair set:

```
Forward primer 2a:
                                        (SEQ ID NO: 3)
5'- GGG AGG AGC GAG GGG ACC GCA G -3'

Forward primer 2b:
                                        (SEQ ID NO: 4)
5'- GGG AGG AGA GAG GGG ACC GCA G -3'

Forward primer 2c:
                                        (SEQ ID NO: 5)
5'- GGG AGG AGC AAG GGG ACC GCA G -3'

Reverse primer 1:
                                        (SEQ ID NO: 6)
5'- GGA GGC CAT CCC GGG CGA TCT AT -3'

Reverse primer 3:
                                        (SEQ ID NO: 7)
5'- GGA GGC CAT CCC CGG CGA CCT AT -3'

Reverse primer 3a:
                                        (SEQ ID NO: 8)
5'- TTC TCC ATT CAA CGG AGG GCG ACA -3'

Reverse primer 3b:
                                        (SEQ ID NO: 9)
5'- TTC TCC ATT CAA GGG AGG GCG ACA -3'
```

HLA-DRB1 locus primary primer pair set:

```
Forward primer 1a:
                                        (SEQ ID NO: 10)
5'- CTT GGA GGT CTC CAG AAC AGG -3'

Forward primer 1b:
                                        (SEQ ID NO: 11)
5'- CTT AGA GGT CTC CAG AAC CGG -3'

Reverse primer 4-xx:
                                        (SEQ ID NO: 12)
5'- CACACACACACACACACTCAGATTC -3'

Reverse primer 4-07:
                                        (SEQ ID NO: 13)
5'- CACACACACAACCACACTCAGATTC -3'

Reverse primer 4-10:
                                        (SEQ ID NO: 14)
5'- CACACACACACACAGAGTCAGATTC -3'
```

Figure 4A:
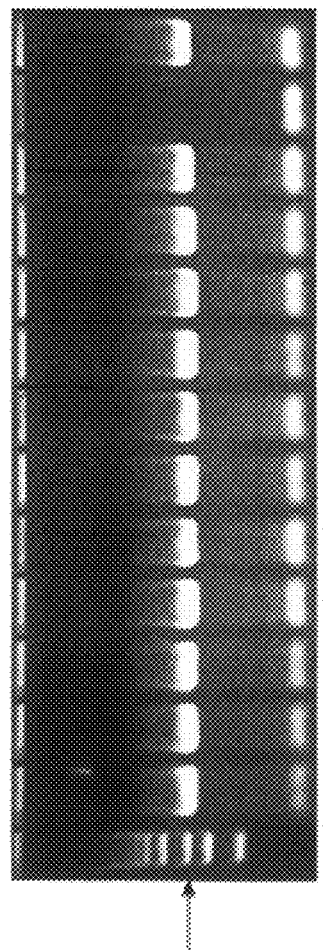
FIGS. 4A-4C are gels showing exon specific Secondary PCR reactions performed upon the Primary PCR reaction products displayed in FIG. 3: using a set of PCR primers specific for HLA-A exon set 2 and 3, performed simultaneously as a multiplex PCR reaction (FIG. 4A), using a set of PCR primers specific for HLA-B exons 2 and 3, performed simultaneously as a multiplex PCR reaction (FIG. 4B), and using a set of PCR primers specific for all related variants of HLA-DRB1 exon 2, performed simultaneously as a multiplex PCR reaction (FIG. 4C). Template for these Secondary PCR reactions was the locus specific Primary PCR product, amplified directly from 12 whole blood samples shown in FIGS. 3A-3C, diluted 1:100 in molecular biology grade water then applied as 2 μL each into the 50 μL Secondary PCR reactions listed above. Negative control is also shown.
Figure 4B:
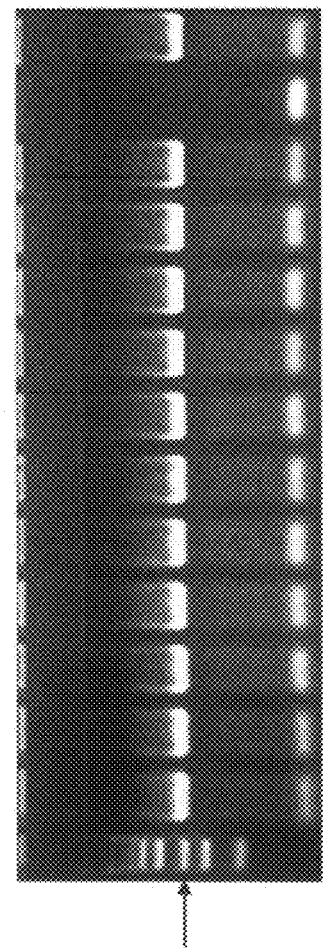
Figure 4C:
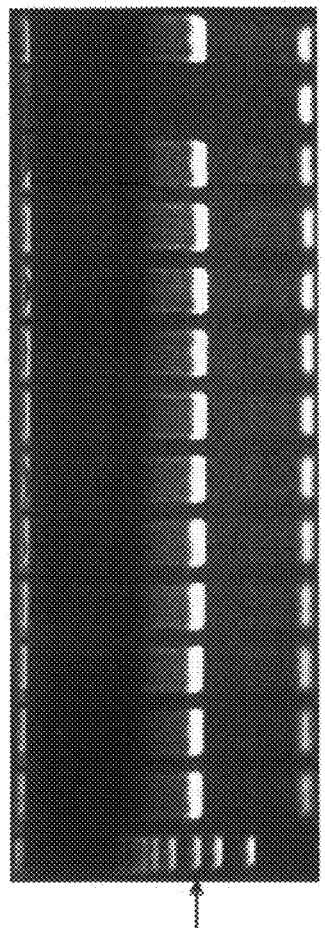

The product from the locus-specific reactions (FIGS. 3A-3C), diluted 1:100 in molecular biology grade water, are used as a template for subsequent exon-specific "nested" PCR reactions (FIGS. 4A-4C). PCR reactions are performed using Applied Biosystems' (Foster City, Calif.) AMPLITAQ GOLD® DNA Polymerase in a 100 µl reaction volume with the following components: 5 µl of 1:100 diluted locus specific PCR product, 1×PCR Buffer II, 1.5 mM $MgCL_2$, 0.16 mg/ml BSA (fraction V), 0.2 mM each dNTP, 400 nM each primer, and 4 units of AMPLITAQ GOLD® DNA Polymerase. Cycling conditions are: initial denaturation at 94° C. for 2 minutes followed by 40 cycles of (i) denaturing at 98° C. for 30 seconds, (ii) annealing at 68° C. for 30 seconds, and (iii) extension at 72° C. for 30 seconds, then a final extension step of 72° C. for 7 minutes. Exon-specific PCR primers are labeled with Cyannine 3 dye to facilitate detection of positive hybridization events by laser excitation/emission in a microarray scanner such as a ProScan Array HT (Perkin-Elmer, Waltham, Mass.).

Exon Specific Secondary PCR Primer Sequences
HLA-A exon 2 secondary primer pair:

```
Forward primer 2b-24:
                                        (SEQ ID NO: 15)
5'-(cy3) AGCCTGGTTCACTSCTCGYCCCCAGGCTC -3'
```

-continued

```
Reverse primer 2a-28:
                                                (SEQ ID NO: 16)
5'-(cy3) TAC TAC AAC CTT GCC TCG CTC TGG TTG TAG
TAG C -3'
```

HLA-A exon 3 secondary primer pair:

```
Forward primer 2b-24:
                                                (SEQ ID NO: 17)
5'-(cy3) GTGAGAACTAGTCSGGGCCAGGTTCTCACA -3'

Reverse primer 2b-26:
                                                (SEQ ID NO: 18)
5'-(cy3) GTACCAGGTTCCCGTGGCCCCYGGTACC -3'
```

HLA-B exon 2 secondary primer pair:

```
Forward primer 2c-20:
                                                (SEQ ID NO: 19)
5'-(cy3) ACCCTCTTGAGCCGCGCCGGKAGGAGGGTC-3'

Reverse primer 2a-28:
                                                (SEQ ID NO: 20)
5'-(cy3) TAC TAC AAC CTT GCC TCG CTC TGG TTG TAG
TAG C -3'
```

HLA-B exon 3 secondary primer pair:

```
Forward primer 2a-22:
                                                (SEQ ID NO: 21)
5'-(cy3) GTGAGACTTACCGGGGCCAGGGTCTCACA -3'

Reverse primer 2a-26:
                                                (SEQ ID NO: 22)
5'-(cy3) GTA CCA GGT TCC CAC TGC CCC TGG TAC C -3'
```

DRB1 exon 2 secondary primer pair set:

```
Forward primer 3-xx-24:
                                                (SEQ ID NO: 23)
5'-(cy3) AAC GTG CTT TTT CGT GTC CCC ACA GCA CGT
TTC -3'

Forward primer 3-04-24:
                                                (SEQ ID NO: 24)
5'-(cy3) AAC GTG CTT TTT CTT GTC CCC CCA GCA CGT
TTC -3'

Forward primer 3-07-24:
                                                (SEQ ID NO: 25)
5'-(cy3) AAC GTG CTT TTT TGT GCC CCC ACA GCA CGT
TTC -3

Reverse primer 3-xx-20:
                                                (SEQ ID NO: 26)
5'-(cy3) TGCAGCTTTGCTCACCTCGCCGCTGCAC -3'

Reverse primer 3-09-22:
                                                (SEQ ID NO: 27)
5'-(cy3) TGCAGAGTTGCTTACCTCGCCTCTGCAC -3'
```

Exon-specific PCR's, amplified in a single PCR reaction as a set, are used as target in self assembling single base discriminatory microarray hybridizations using the following procedure: Microarray slides are pre-rinsed with ddiH2O at 40° C. for 15 minutes before assembling into Grace Bio-Labs (Bend, Oreg.) ProPlate Multi-Array Slide System. Each of the 16 wells on a microarray slide/Poroplate superstructure is equilibrated with 75 µl pre-hybridization buffer consisting of 3×SSC (Sigma-Aldrich, St. Louis, Mo.) and 5×Denhardt's Solution (Amresco, Inc. Solon, Ohio). Target PCR product is combined with other reagents to make a hybridization cocktail consisting of 3×SSC, 5×Denhardt's Solution, and 50% exon-specific PCR product. This cocktail is then denatured for 5 minutes at 99° C. followed by snap-cooling to −20° C. for 3 minutes immediately prior to hybridization to a genotyping microarray. Denatured PCR product is applied to previously equilibrated microarrays and are allowed to hybridize at 25° C. for 16 hours. After hybridization arrays are washed twice with 100 µl per well of 0.2×SSC for 15 minutes each wash. Array cassettes are disassembled and slides are washed in bulk format briefly with 0.2×SSC then dried by centrifugation at 60×g in an Eppendorf 5810 centrifuge. Fluorescence data is acquired by scanning slides in a Perkin-Elmer ScanArray Lite laser scanner using Cyannine-3 and Cyannine-5 channels set for 60% and 40% PMT gain, respectively. Resulting data files, consisting of a quantitative fluorescence measurement for each probe feature on a microarray slide, are analyzed by software developed by Genomics USA in order to generate HLA genotype calls.

EXAMPLE 3

Lab-on-a-Chip Microarray Platform

The LoC microarray platform (In-Check™) system integrates PCR amplification and microarray detection processes for genetic testing in a single lab-on-a-chip. The system is designed for identification of complex nucleic-acid analytes, such as in HLA-typing, by integrating PCR amplification and hybridization on a single low-density microarray. The system is based on a technology that monolithically integrates a PCR micro-reactor fluidically connected with a hybridization reactor composed of a low-density microarray on a miniaturized silicon lab-on-chip (LoC).

PCR Module

The PCR module (In-Check™) has integrated silicon heaters, temperature sensor and miniaturized 25 µl volume which allow the PCR module to perform the rapid heating and cooling cycles required for highly reliable, end-point PCR. The PCR module is thermally driven by the temperature control system (TCS; In-Check™). The TCS allows fast and programmable temperature cycling in a way that allows 5 different LoC tests to be performed in parallel.

Lab-on-Chip

The LoC is a disposable device that is manufactured using silicon-semiconductor MEMS technology and is mounted on a 1"×3" plastic slide that provides the necessary mechanical, thermal & electric connections. The silicon chip is an electrically active system that monolithically integrates a 25 µl PCR reactor with a hybridization area of 30 µl that hosts a low density microarray of up to 500 spots in 1 cm2. Accurate temp control is maintained through 3 resistive heaters and temp sensors located above the PCR reactor.

Microarray Hybridization and Detection

Up to 500 probe spots can be positioned within the 1 cm×1 cm microarray module of the LoC chip. The microarray module is fluidically connected to the PCR chambers on the LOC (In-Check™) and is coupled to an on-chip temperature control system, thus allowing full temperature control during hybridization and washing. After hybridization, the microarray module is read by inserting the entire 1"×3" LoC into the microarray optical reader (OR; In-Check™). Depending on the resolution required, scanning by the OR typically takes less than 60 seconds, followed by direct data transfer to additional software, such as Ricimer (GenUSA, www.GenomicsUSA.com), for genotyping. Samples are applied directly to the LoC with ordinary lab tools via the loading station. All processing can be performed by staff with only routine biochemical training. It is expected with raw blood as the sample input, as many as 50 HLA-Loc tests could be done per day, per workstation (5 at a time on the PCR module) with essentially only a manual pipetting as the requisite lab equipment.

Microarray Processing

Figure 10:
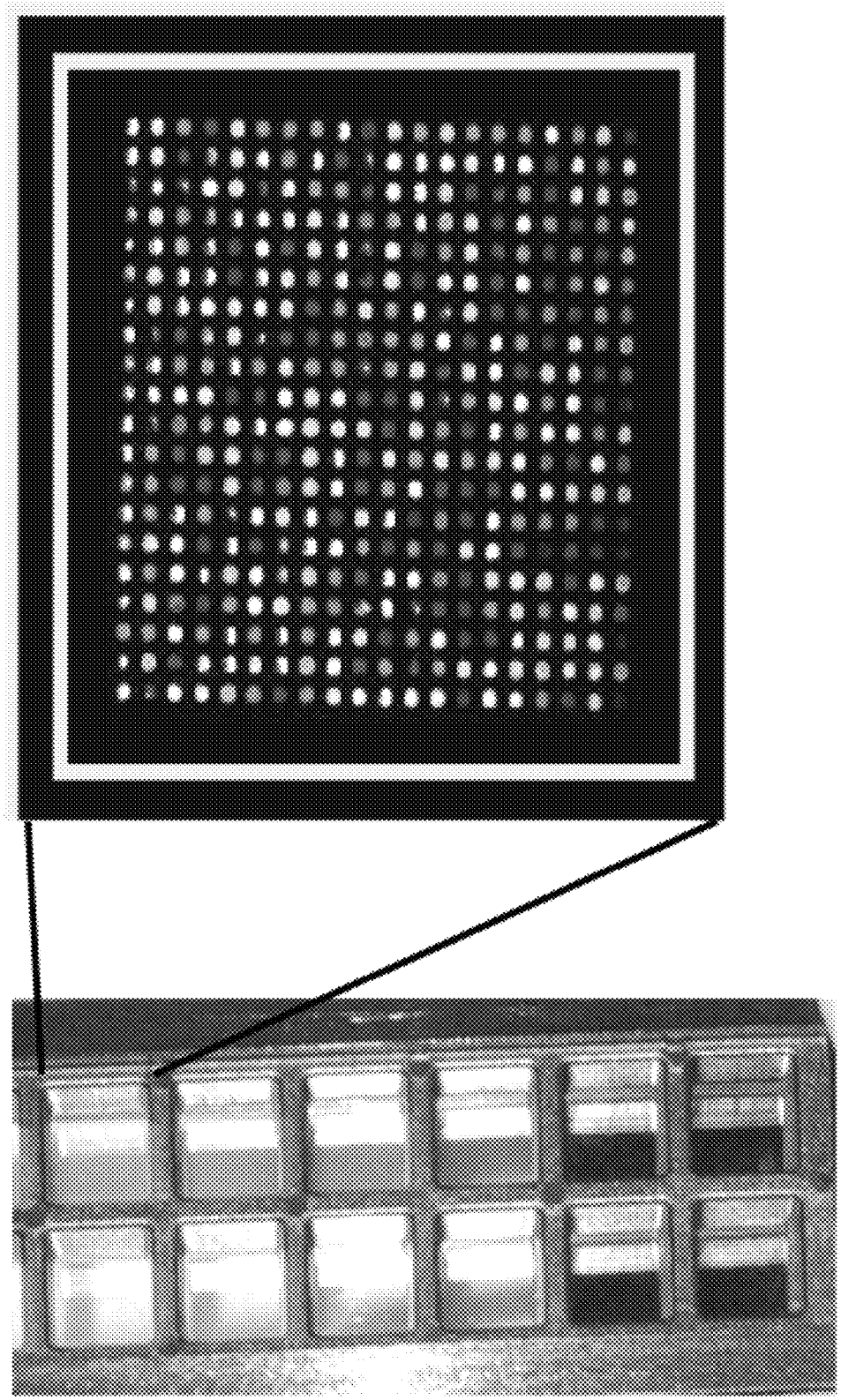
FIG. 10 shows HLA-Chip Design. HLA-Chip layout is presented in a 16 array/slide format. Sixteen identical microarrays are separated, fluidically, by a removable gasket. Subsequent to room temperature hybridization and washing, the resulting microarray data are obtained as a two-color image (right) where hybridization probe position is identified in red (Cy-5) and experimental hybridization signals are quantified in green (Cy-3). These image data are quantified and used for first-level microarray analysis and then compiled to generate an HLA-Type.

Microarray-based hybridization technology was used for HLA-typing of A, B, and DRB1. HLA-Chips were washed with diH$_2$O followed by gasketing to isolate each array in the 16 well format (FIG. 10) as one example of a method of sample containment. A 15 minute equilibration was performed with 75 µl of pre-hybridization cocktail: 3×GMS Buffer 1 and 5×GMS Buffer 2. The 2° PCR product (37.5 µL of a 50 µL reaction) was mixed in a 1:1 ratio with hybridization master mix with a final concentration of: GMS Buffer 1, 5×GMS Buffer 2. The PCR product-hybridization mixture was denatured at 99° C. for 5 minutes and immediately placed in a cool block at −20° C. for 4 minutes. The hybridization cocktail was applied to HLA-Chips and allowed to hybridize overnight at room temperature in a humidity chamber. Post-hybridization washes were performed with 0.2× Buffer 1 for a total of nine buffer exchanges and two 15 minute washes. Following gasket disassembly, the HLA-Chips were dipped ten times in a 0.2× Buffer 1 bath. A 2 minute centrifugation was performed to remove remaining buffer. Arrays were scanned at 635 nm to detect the Cy-5 labelled oligo-T marker and at 532 nm to detect the Cy-3 amplicon. The Cy-5 labelled marker signals were used to assist automated spot finding by imager software. All reagents are available from the GMS Biotech.

lying microarray surface, which are optimized to perform hybridization analysis at ambient temperature, thereby allowing hybridization on a bench-top or an open robotic stage. Finally, each microarray has been designed so as to analyze SNP variation, in phase, over domains as large as 50 bases, thus providing for experimentally-determined allelotyping over those extended domains. Table I shows generalized design principles of the HLA-Chip Microarray probes.

TABLE 1

HLA-Chip Microarray Probes: Generalized Design Principles

| Probe Structure | $T_m$ | Probe Assembly Mechanism | Hybridization Conditions | Wash Conditions |
|---|---|---|---|---|
| $T_n - N_m - T_n$ Length = 30 bases = [m + 2n] m = 10-16 bases n = [30 − m]/2 No chemical modifications | 40° C. | Physical adsorption to an amino-silane surface: Thus bypassing chemical modification of the probes 2 × 8 well glass slides Microscope grade | Room Temperature Humidity Chamber Use raw secondary amplicon derived from 1 ng of purified DNA | Room Temperature Open to Air 2 × 8 well glass slides Microscope grade |

Microarrays of this type have been manufactured by standard piezoelectric printing at AMI Inc (Chandler Ariz.) on a standard 1"×3" glass slide format (15). They are manufactured as 16 identical arrays per slide in a 2×8 format with each array fluidically isolated, as a well, via removable gaskets. Three such array types are fabricated (one type per slide) allowing 16 A, B, or DRB1 typing reactions to be performed per slide, in parallel. Upon completion of the tandem PCR reaction set described in Table 2, each resulting PCR product is diluted 1-1 with hybridization buffer, heated briefly to 99° C. to denature the sample, then pipetted directly into a well, followed by overnight room temperature hybridization.

TABLE 2

PCR Design Principles for Raw Sample Genotyping on HLA-Chips

| Reaction | Primer | Calculated $T_m$ | Amplicon | Annealing | Extension |
|---|---|---|---|---|---|
| Primary PCR | 20-24 bases | 66° C. +/− 2° C. | Variable | Annealing HLA-A 67° C. Annealing HLA-B,-DRB1 69° C. | Extension 72° C. 35 cycles |
| Secondary PCR | 20-24 bases 5' dye label | 66° C. +/− 2° C. | 300 bp +/− 50 bp | Annealing 68° C. | Extension 72° C. 40 cycles |

Microarray Image Processing

For clinical and epidemiological applications of the HLA-Chip, it is necessary to automatically digitize raw microarray image data, and then to convert those image data into allele-specific probe calls, in accord with the relationship between probe hybridization and (local) allele structure that we have described already.

Automated Array Digitization

Numerical analysis of a microarray image is based on "spot finding" and the integration of hybridization signal intensity, within a spot, once circumscribed. Such spot finding and integration is now a routine functionality in imager software. Automated image analysis by employing the use of a Cy5 labeled 25mer Oligo-dT oligonucleotide, which has been doped at 5% density within each probe element printed onto the array. By introducing such a marker and using both standard optical channels of the imager (Cy5 for the marker and Cy3 for the hybridization signal) it is possible to localize each

EXAMPLE 4

Microarray Design

A microarray technology for high resolution allelotyping of the HLA genes A, B & DRB1 developed. HLA-Chips all share a number of common design principles. Each gene [A,B, or DRB1] is analyzed as a separate microarray, comprising a set of 150-350 distinct probes, all fabricated with oligo-T tails to facilitate adsorptive association to the under-probe spot, independently of others: in a sense, the number of fiducial markers equals that of the hybridization signals, to create redundancy.

Automated Assembly of Allele-specific Probe Hybridization Data into an HLA-allelotype A "Ricimer", a software tool to automatically read dot score data and compile it into an HLA allelotype was developed. After reading in the raw data, the probe map, and all known allele sequences for the relevant gene, the Ricimer software determines allele calls based on the presence or absence of hybridization signal from the printed probes. This is accomplished by what is in essence a two-stage process of elimination. The first stage involves examining each probe that is reported to be "off" and comparing the sequence of that probe with the known allele sequences. If an allele's sequence matches the sequence of one or more of the "off" probes then that allele is eliminated as a candidate, as it cannot be one of the pair of alleles present in the sample.

Once this first stage is complete, the set of candidate alleles has been dramatically reduced. At this point every possible pairing of the remaining alleles is evaluated separately. Each allele pair is compared to the entire set of "on" probes as reported by the array. If there is any discrepancy between the experimentally measured "on" probe set and the expected "on" probe set predicted by the allele sequences, that allele pair is no longer considered a candidate for the solution set. After these two culling steps have been performed, all possible pairings of alleles that can account for the data have been determined and are reported to the user. Typically a calculated probability value based on the worldwide population frequency of the alleles present in the pairings is also reported to assist the user in making a decision. This very powerful allele calling statistical functionality became the basis for the graphical interphase that presents to the user, the certainty of the experimental HLA-type and all possible alternative allele calls.

Figure 11:
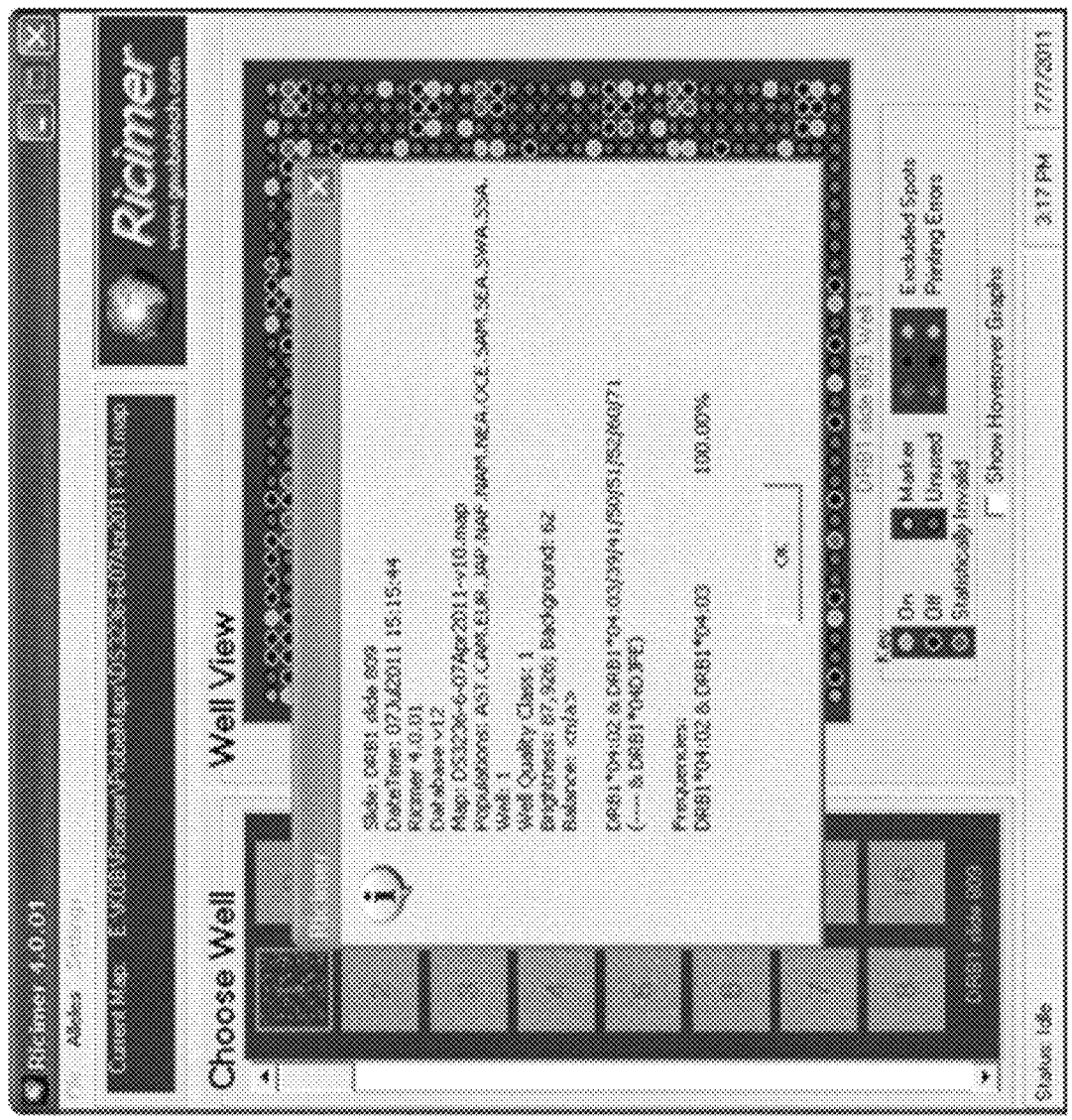
FIG. 11 shows Ricimer Software for Automated HLA-Typing. A screen shot is presented for Ricimer software, a copy of which may be obtained from the GMS Biotech. An image of an entire 16-sample set of hybridization data is presented (Left, beneath) and a two-color rendering of quantified microarray hybridization signals for a single array (Right, beneath). In the foreground is a representative HLA-Typing report for one sample, obtained from one of 16 microarrays in a slide. This report includes QC data related to the quality of the microarray data, as well as the HLA-Type obtained (DRB1 in this case) along with the certainty of the call embodied in the standardized ASHI "string" format. Uncertainty is also presented, when desired as a probability distribution profile among possible alternative allele calls that are consistent with the microarray data.

FIG. 11 reveals typical results of the Ricimer allele calling algorithm. In this case the software determined that one of the alleles was DRB1*04:02 but could not exactly determine what the other allele was so it reported all possible pairs to the user. Since DRB1*04:03 occurs much more frequently in the overall worldwide population than the other possible alleles, the software assigned it a high likelihood of being the correct allele call.

Quantitative Microarray Analysis

As a first measure of HLA-typing from such samples, 37.5 µl of the 50 µl 2o PCR reactions (as in FIG. 12) was used without any purification, diluted 1-1 with hybridization buffer, heat denatured, then subjected to overnight hybridization at room temperature on the appropriate A, B or DRB1 microarray.

The resulting microarrays were then imaged with an Axon imager (Molecular Dynamics) and the total integrated Cy-3 hybridization signal intensity for each probe spot was stored as an Excel file. FIGS. 13A-13F, 14A-14F and 15A-15F display scatter plots of representative integrated spot intensity data for raw samples vs. the corresponding data derived from matched purified DNA. These correlation diagrams were subjected to linear regression to yield a slope, intercept, and standard R2 linear correlation coefficient.

In the representative scatter plots in FIGS. 13A-13F, 14A-14F and 15A-15F, it can be seen that in the absence of sample or image data adjustment of any kind, the raw vs. purified samples display a clear linear correlation with slopes in the 0.76-1.73 range and the squared correlation coefficients $R^2 > 0.71$, thus indicating that the raw and purified DNA samples have produced microarray data of similar overall intensity (slope near 1) which are seen to be highly correlated ($R^2 > 0.7$) to the corresponding purified DNA microarray data. As seen in the Tables, the full set of 2 raw samples show, as a class, microarray correlations that are similar in a statistical sense to the corresponding purified DNA data. Greater than 87.5% of all measurements display raw/purified DNA correlations with $R^2 > 0.8$ (white blocks in Tables).

TABLE 3

PCR Protocols for HLA-Chips: Raw Sample and Purified DNA

| Sample Type | Buffer | Incubation Time | Incubation Temp. | Purification Method | Final Volume and Buffer | Dilution for Primary PCR | Primary PCR Input | Dilution for Secondary PCR | Secondary PCR Input |
|---|---|---|---|---|---|---|---|---|---|
| Raw Buccal Swab | 150 ul of 100 mM Borate + 1 mM EDTA | 2.5 hours | 70° C. | N/A | 150 ul of 100 mM Borate + 1 mM EDTA | N/A | 1 ul | 1:10 | 2.5 ul |
| Purified DNA Buccal Swab | 150 ul of 100 mM Borate + 1 mM EDTA | 2.5 hours | 70° C. | Qiagen Kit (QIAamp DNA Blood Mini Kit Catalog: 51104) | 100 ul of Distilled Water | N/A | 1 ul | 1:100 | 2.5 ul |
| Raw Mouthwash | Collected in 10 mL Scope, washed with 10 mL 20% EtOH, pellet re-suspended in 300 ul 100 mM Borate + 1 mM EDTA | 2.5 hours | 70° C. | N/A | 300 ul 100 mM Borate + 1 mM EDTA | 1:20 | 1 ul | 1:100 | 2.5 ul |
| Purified DNA Mouthwash | Collected in 10 mL Scope, washed twice with 10 mL 1xPBS, pellet re-suspended in 180 ul 1xPBS + 200 ul Qiagen Buffer AL + 20 ul Qiagen Protease | 10 minutes | 56° C. | Qiagen Kit (QIAamp DNA Blood Mini Kit Catalog: 51104) | 150 ul of Distilled Water | N/A | 1 ul | 1:100 | 2.5 ul |
| Raw Oragene (OG-510 and ON-500) | Oragene Kit OG-510/ON-500 Buffer | N/A | N/A | N/A | Oragene Kit OG-510/ON-500 Buffer | 1:50 | 1 ul | 1:100 | 2.5 ul |
| PI Raw Oragene (OG-510 and ON-500) | Oragene Kit OG-510/ON-500 Buffer | 3 hours (minimum of 2 hours) | 50° C. | N/A | Oragene Kit OG-510/ON-500 Buffer | 1:50 | 1 ul | 1:100 | 2.5 ul |

TABLE 3-continued

PCR Protocols for HLA-Chips: Raw Sample and Purified DNA

| Sample Type | Buffer | Incubation Time | Incubation Temp. | Purification Method | Final Volume and Buffer | Dilution for Primary PCR | Primary PCR Input | Dilution for Secondary PCR | Secondary PCR Input |
|---|---|---|---|---|---|---|---|---|---|
| Purified DNA Oragene (OG-510 and ON-500) | Oragene Kit OG-510/ ON-500 Buffer | 3 hours (minimum of 2 hours) | 50° C. | Oragene Kit OG-510/ON-500 | OG-510: 100 ul TE Buffer, ON-500: 50 ul TE Buffer | N/A | 1 ul | 1:100 | 2.5 ul |

TABLE 4

Raw Buccal Swabs, Scope Mouthwash vs. Matched Purified DNA Slopes, $R^2$ values, and Microarray Signal Strengths for A, B, and DRB1

| | | Raw vs. Purified DNA Buccal Swab | | | | Raw vs. Purified DNA Mouthwash | | | |
|---|---|---|---|---|---|---|---|---|---|
| | | | | Microarray Signal Strength | | | | Microarray Signal Strength | |
| ID | HLA | Slope | $R^2$ | Raw | Purified | Slope | $R^2$ | Raw | Purified |
| A1 | A | 0.86 | 0.97 | 93 | 82 | 0.65 | 0.83 | 107 | 86 |
|  | B | 0.84 | 0.87 | 68 | 66 | 0.96 | 0.95 | 53 | 70 |
|  | DRB1 | 1.00 | 0.99 | 94 | 101 | 1.04 | 0.88 | 130 | 146 |
| A2 | A | 0.97 | 0.87 | 135 | 135 | 1.17 | 0.89 | 116 | 147 |
|  | B | 0.91 | 0.85 | 83 | 89 | 0.87 | 0.97 | 70 | 86 |
|  | DRB1 | 0.89 | 0.86 | 123 | 122 | 0.91 | 0.97 | 96 | 94 |
| A3 | A | 1.15 | 0.88 | 100 | 114 | 1.13 | 0.95 | 53 | 61 |
|  | B | 1.02 | 0.83 | 131 | 144 | 1.21 | 0.90 | 66 | 129 |
|  | DRB1 | 0.90 | 0.87 | 134 | 133 | 0.79 | 0.74 | 135 | 134 |
| A4 | A | 1.64 | 0.76 | 27 | 55 | 1.25 | 0.74 | 23 | 37 |
|  | B | 0.96 | 0.84 | 85 | 81 | 1.37 | 0.75 | 43 | 78 |
|  | DRB1 | 0.78 | 0.81 | 129 | 128 | 0.90 | 0.91 | 108 | 90 |
| A5 | A | 1.12 | 0.85 | 91 | 118 | 1.06 | 0.82 | 103 | 114 |
|  | B | 1.16 | 0.91 | 78 | 107 | 1.01 | 0.92 | 97 | 107 |
|  | DRB1 | 0.95 | 0.88 | 111 | 118 | 1.08 | 0.92 | 99 | 112 |
| A6 | A | 0.97 | 0.87 | 64 | 75 | 1.05 | 0.91 | 139 | 154 |
|  | B | 1.16 | 0.88 | 90 | 118 | 1.73 | 0.94 | 56 | 83 |
|  | DRB1 | 0.98 | 0.94 | 81 | 84 | 1.01 | 0.96 | 82 | 89 |
| A7 | A | 1.47 | 0.97 | 71 | 90 | 1.64 | 0.71 | 139 | 151 |
|  | B | 1.21 | 0.86 | 120 | 134 | 0.43 | 0.78 | 136 | 140 |
|  | DRB1 | 1.00 | 0.76 | 128 | 163 | 0.66 | 0.73 | 145 | 131 |
| A8 | A | 1.51 | 0.79 | 29 | 63 | 1.15 | 0.95 | 110 | 111 |
|  | B | 1.04 | 0.91 | 64 | 66 | 1.30 | 0.96 | 63 | 74 |
| * | DRB1 | 0.94 | 0.68 | 116 | 117 | 1.15 | 0.95 | 85 | 100 |
| A9 | A | 1.06 | 0.88 | 69 | 73 | 1.02 | 0.81 | 77 | 92 |
|  | B | 0.95 | 0.83 | 82 | 79 | 1.05 | 0.88 | 78 | 88 |
|  | DRB1 | 0.87 | 0.78 | 160 | 164 | 0.77 | 0.96 | 145 | 129 |
| A10 | A | 0.91 | 0.98 | 76 | 75 | 0.82 | 0.90 | 105 | 83 |
|  | B | 1.35 | 0.81 | 58 | 89 | 0.22 | 0.87 | 237 | 70 |
|  | DRB1 | 0.82 | 0.90 | 171 | 168 | 0.93 | 0.89 | 157 | 169 |
| * A11 | A | 2.30 | 0.56 | 22 | 77 | 0.76 | 0.90 | 80 | 60 |
|  | B | 0.95 | 0.95 | 73 | 70 | 0.86 | 0.95 | 88 | 83 |
|  | DRB1 | 0.93 | 0.86 | 140 | 139 | 0.63 | 0.96 | 151 | 79 |
| A12 | A | 1.63 | 0.90 | 39 | 68 | 0.80 | 0.75 | 88 | 73 |
|  | B | 1.13 | 0.84 | 88 | 119 | 1.05 | 0.98 | 113 | 119 |
|  | DRB1 | 1.01 | 0.85 | 137 | 133 | 0.54 | 0.82 | 137 | 76 |
| Mean |  | 1.09 | 0.86 | 93 | 104 | 0.97 | 0.88 | 103 | 101 |
| STDEV |  | 0.30 | 0.08 | 37 | 32 | 0.30 | 0.08 | 41 | 31 |

$R^2$ is 0.81-0.99
$R^2$ is 0.71-0.80
* $R^2$ is 0.51-0.70

TABLE 5

Raw Oragene OG-510, ON-500 vs. Matched Purified DNA Slopes,
$R^2$ values, and Microarray Signal Strengths for A, B, and DRB1

| | | Raw vs. Purified DNA Oragene OG-510 | | | | Raw vs. Purified DNA Oragene OG-510 PI | | | | Raw vs. Purified DNA Oragene ON-500 | | | | Raw vs. Purified DNA Oragene ON-500 PI | | | |
|---|---|---|---|---|---|---|---|---|---|---|---|---|---|---|---|---|---|
| | | | | Microarray Signal Strength | | | | Microarray Signal Strength | | | | Microarray Signal Strength | | | | Microarray Signal Strength | |
| ID | HLA | Slope | $R^2$ | Raw | Purified | Slope | $R^2$ | Raw | Purified | Slope | $R^2$ | Raw | Purified | Slope | $R^2$ | Raw | Purified |
| A1 | A | 1.13 | 0.95 | 31 | 37 | 0.97 | 0.95 | 34 | 37 | 1.19 | 0.83 | 73 | 118 | 1.02 | 0.93 | 101 | 118 |
| | B | 0.98 | 0.90 | 65 | 100 | 0.88 | 0.77 | 60 | 100 | 1.25 | 0.95 | 59 | 96 | 0.76 | 0.90 | 78 | 96 |
| | DRB1 | 1.10 | 0.90 | 107 | 113 | 1.01 | 0.90 | 114 | 113 | 1.22 | 0.95 | 102 | 114 | 1.25 | 0.97 | 96 | 114 |
| A2 | A | 1.00 | 0.90 | 134 | 172 | 1.68 | 0.80 | 65 | 172 | 1.14 | 0.78 | 94 | 166 | 1.45 | 0.77 | 72 | 166 |
| | B | 1.13 | 0.97 | 91 | 103 | 1.06 | 0.98 | 98 | 103 | 1.01 | 0.92 | 66 | 112 | 0.83 | 0.95 | 81 | 112 |
| | DRB1 | 0.90 | 0.92 | 88 | 74 | 1.24 | 0.98 | 64 | 74 | 0.99 | 0.92 | 86 | 77 | 1.26 | 0.94 | 64 | 77 |
| A3 | A | 1.40 | 0.90 | 72 | 119 | 1.10 | 0.96 | 109 | 119 | 0.98 | 0.88 | 105 | 105 | 0.94 | 0.92 | 106 | 105 |
| | B | 0.98 | 0.97 | 142 | 144 | 0.91 | 0.97 | 153 | 144 | 1.16 | 0.79 | 102 | 157 | 0.98 | 0.86 | 146 | 157 |
| * DRB1 | | 0.77 | 0.70 | 146 | 138 | 1.05 | 0.91 | 139 | 138 | 0.78 | 0.93 | 96 | 68 | 1.08 | 0.93 | 70 | 68 |
| A4 | A | 0.93 | 0.81 | 87 | 95 | 1.20 | 0.87 | 77 | 95 | 0.99 | 0.90 | 75 | 76 | 1.08 | 0.86 | 66 | 76 |
| | B | 0.56 | 0.90 | 66 | 94 | 1.12 | 0.90 | 107 | 94 | 0.58 | 0.91 | 79 | 101 | 0.49 | 0.92 | 82 | 101 |
| | DRB1 | 0.57 | 0.98 | 71 | 39 | 0.84 | 0.98 | 49 | 39 | 0.61 | 0.97 | 75 | 42 | 0.85 | 0.97 | 55 | 42 |
| A5 | A | 0.75 | 0.86 | 129 | 123 | 0.98 | 0.85 | 114 | 123 | 1.03 | 0.86 | 86 | 113 | 1.03 | 0.88 | 88 | 113 |
| | B | 1.45 | 0.90 | 54 | 99 | 0.94 | 0.96 | 101 | 99 | 0.91 | 0.91 | 80 | 93 | 0.88 | 0.96 | 101 | 93 |
| | DRB1 | 1.34 | 0.96 | 90 | 138 | 1.21 | 0.93 | 83 | 138 | 1.22 | 0.94 | 93 | 135 | 1.15 | 0.90 | 84 | 135 |
| A6 | A | 0.89 | 0.95 | 141 | 136 | 1.07 | 0.96 | 123 | 136 | 0.76 | 0.73 | 134 | 125 | 0.82 | 0.71 | 121 | 125 |
| | B | 1.07 | 0.95 | 95 | 108 | 0.90 | 0.94 | 102 | 108 | 0.94 | 0.96 | 90 | 102 | 0.86 | 0.93 | 98 | 102 |
| | DRB1 | 1.41 | 0.96 | 75 | 124 | 1.41 | 0.94 | 63 | 124 | 1.48 | 0.97 | 79 | 125 | 1.42 | 0.93 | 64 | 125 |
| A7 | A | 1.02 | 0.75 | 87 | 99 | 0.92 | 0.83 | 96 | 99 | 0.89 | 0.91 | 63 | 62 | 0.92 | 0.93 | 63 | 62 |
| | B | 1.28 | 0.92 | 88 | 121 | 1.06 | 0.95 | 108 | 121 | 1.46 | 0.80 | 87 | 148 | 1.42 | 0.71 | 92 | 148 |
| | DRB1 | 1.53 | 0.94 | 87 | 155 | 1.79 | 0.93 | 63 | 155 | 1.49 | 0.93 | 90 | 163 | 1.67 | 0.89 | 65 | 163 |
| A8 | A | 0.86 | 0.90 | 69 | 71 | 1.00 | 0.91 | 70 | 71 | 0.85 | 0.95 | 75 | 61 | 0.93 | 0.89 | 72 | 61 |
| | B | 1.34 | 0.91 | 61 | 84 | 0.95 | 0.94 | 81 | 84 | 1.20 | 0.93 | 80 | 92 | 0.88 | 0.96 | 93 | 92 |
| | DRB1 | 0.97 | 0.89 | 77 | 96 | 1.47 | 0.91 | 49 | 96 | 1.22 | 0.95 | 80 | 119 | 1.69 | 0.94 | 52 | 119 |
| A9 | A | 0.88 | 0.93 | 108 | 96 | 0.90 | 0.95 | 107 | 96 | 0.84 | 0.92 | 102 | 96 | 0.95 | 0.93 | 96 | 96 |
| | B | 1.01 | 0.95 | 156 | 182 | 0.98 | 0.97 | 168 | 182 | 1.10 | 0.91 | 73 | 84 | 1.00 | 0.90 | 79 | 84 |
| | DRB1 | 1.33 | 0.96 | 132 | 194 | 1.25 | 0.81 | 111 | 194 | 0.95 | 0.92 | 132 | 132 | 0.88 | 0.93 | 141 | 132 |
| A10 | A | 1.04 | 0.88 | 84 | 92 | 1.60 | 0.84 | 51 | 92 | 0.76 | 0.73 | 93 | 94 | 0.82 | 0.71 | 82 | 94 |
| | B | 1.14 | 0.92 | 67 | 108 | 1.12 | 0.94 | 109 | 108 | 0.96 | 0.96 | 86 | 101 | 1.08 | 0.96 | 110 | 101 |
| | DRB1 | 0.76 | 0.93 | 115 | 89 | 0.82 | 0.93 | 107 | 89 | 0.90 | 0.89 | 158 | 158 | 0.93 | 0.91 | 157 | 158 |
| A11 | A | 0.54 | 0.89 | 74 | 41 | 0.49 | 0.84 | 83 | 41 | 1.19 | 0.86 | 72 | 89 | 1.30 | 0.86 | 65 | 89 |
| | B | 1.35 | 0.86 | 54 | 95 | 1.57 | 0.95 | 112 | 95 | 0.91 | 0.95 | 100 | 111 | 1.31 | 0.94 | 116 | 111 |
| | DRB1 | 1.34 | 0.94 | 84 | 138 | 1.77 | 0.92 | 62 | 138 | 0.92 | 0.90 | 139 | 138 | 0.86 | 0.87 | 141 | 138 |
| A12 | A | 2.60 | 0.76 | 48 | 145 | 1.05 | 0.91 | 127 | 145 | 0.80 | 0.84 | 124 | 117 | 0.90 | 0.84 | 113 | 117 |
| | B | 0.90 | 0.94 | 83 | 87 | 2.22 | 0.94 | 102 | 87 | 0.87 | 0.97 | 97 | 103 | 1.98 | 0.95 | 102 | 103 |
| | DRB1 | 0.88 | 0.91 | 131 | 118 | 0.84 | 0.90 | 128 | 118 | 1.20 | 0.94 | 97 | 135 | 2.20 | 0.93 | 52 | 135 |
| Mean | | 1.09 | 0.90 | 91 | 110 | 1.15 | 0.91 | 94 | 110 | 1.02 | 0.90 | 92 | 109 | 1.11 | 0.90 | 91 | 109 |
| STDEV | | 0.37 | 0.06 | 31 | 36 | 0.34 | 0.05 | 31 | 36 | 0.22 | 0.06 | 22 | 30 | 0.35 | 0.07 | 27 | 30 |

ASHI Nomenclature
ANVB 02/61
BMMP 01:01/01:01N
BJTR 01/42/57
EKN 05/13
FKZ 68:01/68:11N
HTH 44:02/44:19N
TDS 01/42
XKS 03:01/03:01N

TABLE 6

HLA-A Calls: Buccal Swabs, Scope Mouthwash vs. Matched Purified DNA

| | | Purified DNA LabCorp Buccal Swab | | Raw Buccal Swab | | Purified DNA Buccal Swab | | Raw Mouthwash | | Purified DNA Mouthwash | |
|---|---|---|---|---|---|---|---|---|---|---|---|
| ID | HLA | Allele 1 | Allele 2 | Allele 1 | Allele 2 | Allele 1 | Allele 2 | Allele 1 | Allele 2 | Allele 1 | Allele 2 |
| A1 | A* | 11:01:01 | 68:FKZ | 11:01 | 68:01 | 11:01 | 68:01 | 11:01 | 68:01 | 11:01 | 68:01 |
| A2 | A* | 01:BMMP | 24:02:01 | 01:01 | 24:02 | 01:01 | 24:02 | 01:01 | 24:02 | 01:01 | 24:02 |
| A3 | A* | 24:02:01 | 24:02:01 | 24:17 | 24:17 | 24:02 | 24:02 | 24:02 | 24:02 | 24:02 | 24:02 |
| A4 | A* | 02:01:01 | 31:01:02 | 02:03 | 31:01 | 02:01 | 31:01 | 02:01 | 31:01 | 02:01 | 31:01 |
| A5 | A* | 24:02:01 | 68:02 | 24:02 | 68:02 | 24:02 | 68:02 | 24:02 | 68:02 | 24:02 | 68:02 |

TABLE 6-continued

HLA-A Calls: Buccal Swabs, Scope Mouthwash vs. Matched Purified DNA

| | | Purified DNA LabCorp Buccal Swab | | Raw Buccal Swab | | Purified DNA Buccal Swab | | Raw Mouthwash | | Purified DNA Mouthwash | |
|---|---|---|---|---|---|---|---|---|---|---|---|
| ID | HLA | Allele 1 | Allele 2 | Allele 1 | Allele 2 | Allele 1 | Allele 2 | Allele 1 | Allele 2 | Allele 1 | Allele 2 |
| A6 | A* | 01:BMMP | 32:01 | 01:01 | 32:01 | 01:01 | 32:01 | 01:01 | 32:01 | 01:01 | 32:01 |
| A7 | A* | 24:02:01 | 31:01:02 | 24:02 | 31:01 | 24:02 | 31:06 | 24:02 | 31:01 | 24:02 | 31:01 |
| A8 | A* | 30:01:00 | 68:FKZ | 30:18 | 68:01 | 30:01 | 68:01 | 30:01 | 68:01 | 30:01 | 68:01 |
| A9 | A* | 01:BMMP | 26:01:01 | 01:01 | 26:01 | 01:01 | 26:01 | 01:01 | 26:01 | 01:01 | 26:01 |
| A10 | A* | 11:01:01 | 68:FKZ | 11:01 | 68:01 | 11:01 | 68:01 | 11:01 | 68:01 | 11:03 | 68:01 |
| A11 | A* | 03:XKS | 11:01:01 | 03:01 | 11:02 | 03:01 | 11:01 | 03:01 | 11:03 | 03:01 | 11:03 |
| A12 | A* | 01:BMMP | 24:02:01 | 01:01 | 24:03 | 01:01 | 24:03 | 01:01 | 24:03 | 01:01 | 24:03 |

TABLE 7

HLA-A Calls: Oragene OG-510, ON-500 Raw vs. Matched Purified DNA

| | | Purified DNA LabCorp Buccal Swab | | Raw Oragene OG-510 | | PI Raw Oragene OG-510 | | Purified DNA Oragene OG-510 | | Raw Oragene ON-500 | | PI Raw Oragene ON-500 | | Purified DNA Oragene ON-500 | |
|---|---|---|---|---|---|---|---|---|---|---|---|---|---|---|---|
| ID | HLA | Allele 1 | Allele 2 | Allele 1 | Allele 2 | Allele 1 | Allele 2 | Allele 1 | Allele 2 | Allele 1 | Allele 2 | Allele 1 | Allele 2 | Allele 1 | Allele 2 |
| A1 | A* | 11:01:01 | 68:FKZ | 11:01 | 68:01 | 11:01 | 68:01 | 11:01 | 68:01 | 11:01 | 68:10 | 11:17 | 68:10 | 11:01 | 68:01 |
| A2 | A* | 01:BMMP | 24:02:01 | 01:01 | 24:03 | 01:01 | 24:02 | 01:01 | 24:02 | 01:01 | 24:03 | 01:01 | 24:02 | 01:01 | 24:03 |
| A3 | A* | 24:02:01 | 24:02:01 | 24:03 | 24:04 | 24:03 | 24:04 | 24:04 | 24:04 | 24:02 | 24:02 | 24:02 | 24:02 | 24:02 | 24:02 |
| A4 | A* | 02:01:01 | 31:01:02 | 02:01 | 31:01 | 02:01 | 31:01 | 02:01 | 31:01 | 02:01 | 31:01 | 02:01 | 31:01 | 02:01 | 31:01 |
| A5 | A* | 24:02:01 | 68:02 | 24:02 | 68:02 | 24:02 | 68:02 | 24:02 | 68:02 | 24:02 | 68:02 | 24:02 | 68:02 | 24:02 | 68:02 |
| A6 | A* | 01:BMMP | 32:01 | 01:01 | 32:07 | 01:01 | 32:07 | 01:01 | 32:01 | 01:01 | 32:01 | 01:01 | 32:07 | 01:01 | 32:07 |
| A7 | A* | 24:02:01 | 31:01:02 | 24:02 | 31:03 | 24:94 | 31:24 | 24:02 | 31:19 | 24:99 | 31:01 | 24:99 | 31:01 | 24:02 | 31:19 |
| A8 | A* | 30:01:00 | 68:FKZ | 30:01 | 68:01 | 30:01 | 68:01 | 30:01 | 68:01 | 30:01 | 68:01 | 30:01 | 68:01 | 30:01 | 68:01 |
| A9 | A* | 01:BMMP | 26:01:01 | 01:01 | 26:01 | 01:01 | 26:01 | 01:01 | 26:01 | 01:01 | 26:01 | 01:01 | 26:01 | 01:01 | 26:01 |
| A10 | A* | 11:01:01 | 68:FKZ | 11:01 | 68:01 | 11:01 | 68:01 | 11:01 | 68:01 | 11:03 | 68:01 | 11:01 | 68:01 | 11:01 | 68:01 |
| A11 | A* | 03:XKS | 11:01:01 | 03:01 | 11:03 | 03:08 | 11:03 | 03:01 | 11:03 | 03:01 | 11:01 | 03:01 | 11:01 | 03:01 | 11:01 |
| A12 | A* | 01:BMMP | 24:02:01 | 01:01 | 24:02 | 01:01 | 24:20 | 01:01 | 24:02 | 01:01 | 24:20 | 01:01 | 24:20 | 01:01 | 24:20 |

TABLE 8

HLA-B Calls: Buccal Swabs, Scope Mouthwash vs. Matched Purified DNA

| | | Purified DNA LabCorp Buccal Swab | | Raw Buccal Swab | | Purified DNA Buccal Swab | | Raw Mouthwash | | Purified DNA Mouthwash | |
|---|---|---|---|---|---|---|---|---|---|---|---|
| ID | HLA | Allele 1 | Allele 2 | Allele 1 | Allele 2 | Allele 1 | Allele 2 | Allele 1 | Allele 2 | Allele 1 | Allele 2 |
| A1 | B* | 44:HTH | 57:01:01 | 44:02 | 57:01 | 44:02 | 57:01 | 44:02 | 57:01 | 44:02 | 57:01 |
| A2 | B* | 07:ANVB | 08:01:01 | 07:02 | 08:01 | 07:04 | 08:20 | 07:02 | 08:01 | 07:02 | 08:01 |
| A3 | B* | 40:01 | 51:01:01 | 40:01 | 51:01 | 40:01 | 51:01 | 40:01 | 51:01 | 40:01 | 51:01 |
| A4 | B* | 35:TDS | 44:HTH | 35:01 | 44:02 | 35:39 | 44:48 | 35:01 | 44:02 | 35:01 | 44:02 |
| A5 | B* | 14:02 | 39:06:02 | 14:02 | 39:06 | 14:02 | 39:06 | 14:02 | 39:06 | 14:02 | 39:06 |
| A6 | B* | 08:01:01 | 35:08:01 | 08:07 | 35:83 | 08:01 | 35:08 | 08:01 | 35:08 | 08:27 | 35:08 |
| A7 | B* | 35:03 | 51:01:01 | 35:03 | 51:01 | 35:03 | 51:01 | 35:03 | 51:01 | 35:03 | 51:01 |
| A8 | B* | 40:02:01 | 57:01:01 | 40:02 | 57:01 | 40:02 | 57:01 | 40:02 | 57:01 | 40:02 | 57:01 |
| A9 | B* | 15:17 | 27:EKN | 15:17 | 27:05 | 15:17 | 27:05 | 15:17 | 27:05 | 15:17 | 27:05 |
| A10 | B* | 27:EKN | 35:BJTR | 27:05 | 35:01 | 27:05 | 35:01 | 27:05 | 35:01 | 27:05 | 35:01 |
| A11 | B* | 07:ANVB | 44:HTH | 07:02 | 44:02 | 07:02 | 44:02 | 07:02 | 44:02 | 07:02 | 44:02 |
| A12 | B* | 07:ANVB | 57:01:01 | 07:02 | 57:01 | 07:02 | 57:01 | 07:02 | 57:01 | 07:02 | 57:01 |

TABLE 9

HLA-B Calls: Oragene OG-510, ON-500 Raw vs. Matched Purified DNA

| | | Purified DNA LabCorp | | Raw Oragene OG-510 | | PI Raw Oragene OG-510 | | Purified DNA Oragene OG-510 | | Raw Oragene ON-500 | | PI Raw Oragene ON-500 | | Purified DNA Oragene ON-500 | |
|---|---|---|---|---|---|---|---|---|---|---|---|---|---|---|---|
| | | Buccal Swab | | | | | | | | | | | | | |
| ID | HLA | Allele 1 | Allele 2 | Allele 1 | Allele 2 | Allele 1 | Allele 2 | Allele 1 | Allele 2 | Allele 1 | Allele 2 | Allele 1 | Allele 2 | Allele 1 | Allele 2 |
| A1 | B* | 44:HTH | 57:01:01 | 44:02 | 57:01 | 44:02 | 57:01 | 44:02 | 57:01 | 44:02 | 57:01 | 44:02 | 57:01 | 44:02 | 57:01 |
| A2 | B* | 07:ANVB | 08:01:01 | 07:02 | 08:01 | 07:02 | 08:01 | 07:02 | 08:01 | 07:02 | 08:01 | 07:02 | 08:01 | 07:04 | 08:20 |
| A3 | B* | 40:01 | 51:01:01 | 40:01 | 51:01 | 40:01 | 51:01 | 40:01 | 51:01 | 40:01 | 51:01 | 40:01 | 51:01 | 40:01 | 51:01 |
| A4 | B* | 35:TDS | 44:HTH | 35:25 | 44:02 | 35:01 | 44:02 | 35:01 | 44:02 | 35:01 | 44:02 | 35:01 | 44:02 | 35:01 | 44:02 |
| A5 | B* | 14:02 | 39:06:02 | 14:02 | 39:06 | 14:02 | 39:06 | 14:02 | 39:06 | 14:02 | 39:06 | 14:02 | 39:06 | 14:02 | 39:06 |
| A6 | B* | 08:01:01 | 35:08:01 | 08:01 | 35:08 | 08:01 | 35:08 | 08:01 | 35:08 | 08:01 | 35:08 | 08:01 | 35:08 | 08:01 | 35:08 |
| A7 | B* | 35:03 | 51:01:01 | 35:03 | 51:01 | 35:03 | 51:01 | 35:03 | 51:01 | 35:03 | 51:01 | 35:03 | 51:01 | 35:03 | 51:01 |
| A8 | B* | 40:02:01 | 57:01:01 | 40:02 | 57:01 | 40:02 | 57:01 | 40:02 | 57:01 | 40:02 | 57:01 | 40:02 | 57:01 | 40:02 | 57:01 |
| A9 | B* | 15:17 | 27:EKN | 15:17 | 27:05 | 15:17 | 27:05 | 15:17 | 27:05 | 15:17 | 27:05 | 15:17 | 27:05 | 15:17 | 27:05 |
| A10 | B* | 27:EKN | 35:BJTR | 27:05 | 35:01 | 27:05 | 35:01 | 27:05 | 35:01 | 27:05 | 35:01 | 27:05 | 35:01 | 27:05 | 35:01 |
| A11 | B* | 07:ANVB | 44:HTH | 07:02 | 44:02 | 07:02 | 44:02 | 07:02 | 44:02 | 07:02 | 44:53 | 07:02 | 44:02 | 07:02 | 44:53 |
| A12 | B* | 07:ANVB | 57:01:01 | 07:02 | 57:13 | 07:02 | 57:01 | 07:02 | 57:01 | 07:02 | 57:01 | 07:02 | 57:01 | 07:02 | 57:01 |

TABLE 10

HLA-DRB1 Calls: Buccal Swabs, Scope Mouthwash vs. Matched Purified DNA

| | | Purified DNA LabCorp Buccal Swab | | Raw Buccal Swab | | Purified DNA Buccal Swab | | Raw Mouthwash | | Purified DNA Mouthwash | |
|---|---|---|---|---|---|---|---|---|---|---|---|
| ID | HLA | Allele 1 | Allele 2 | Allele 1 | Allele 2 | Allele 1 | Allele 2 | Allele 1 | Allele 2 | Allele 1 | Allele 2 |
| A1 | DRB1* | 04:01 | 07:01 | 04:01 | 07:01 | 04:01 | 07:01 | 04:01 | 07:01 | 04:01 | 07:01 |
| A2 | DRB1* | 03:01 | 15:01 | 03:01 | 15:01 | 03:07 | 15:01 | 03:01 | 15:01 | 03:01 | 15:01 |
| A3 | DRB1* | 08:32 | 15:01 | 08:32 | 15:01 | 08:32 | 15:01 | 08:32 | 15:01 | 08:32 | 15:01 |
| A4 | DRB1* | 04:03 | 09:01 | 04:03 | 09:01 | 04:58 | 09:01 | 04:03 | 09:01 | 04:03 | 09:01 |
| AS | DRB1* | 08:02 | 13:03 | 08:02 | 13:03 | 08:02 | 13:03 | 08:02 | 13:03 | 08:02 | 13:03 |
| A6 | DRB1* | 03:01 | 11:03 | 03:01 | 11:03 | 03:01 | 11:03 | 03:01 | 11:03 | 03:07 | 11:03 |
| A7 | DRB1* | 04:07 | 13:01 | 04:07 | 13:01 | 04:07 | 13:01 | 04:07 | 13:01 | 04:07 | 13:01 |
| A8 | DRB1* | 04:07 | 15:02 | 04:07 | 15:02 | 04:07 | 15:27 | 04:07 | 15:02 | 04:07 | 15:02 |
| A9 | DRB1* | 01:01 | 13:02 | 01:01 | 13:02 | 01:01 | 13:02 | 01:01 | 13:02 | 01:01 | 13:02 |
| A10 | DRB1* | 01:01 | 13:01 | 01:01 | 13:01 | 01:01 | 13:01 | 01:01 | 13:01 | 01:01 | 13:01 |
| A11 | DRB1* | 04:01 | 15:01 | 04:01 | 15:01 | 04:01 | 15:01 | 04:01 | 15:01 | 04:01 | 15:01 |
| A12 | DRB1* | 07:01 | 08:01 | 07:01 | 08:01 | 07:01 | 08:01 | 07:01 | 08:01 | 07:01 | 08:01 |

TABLE 11

HLA-DRB1 Calls: Oragene OG-510, ON-500 Raw vs. Matched Purified DNA

| | | Purified DNA LabCorp | | Raw Oragene OG-510 | | PI Raw Oragene OG-510 | | Purified DNA Oragene OG-510 | | Raw Oragene ON-500 | | PI Raw Oragene ON-500 | | Purified DNA Oragene ON-500 | |
|---|---|---|---|---|---|---|---|---|---|---|---|---|---|---|---|
| | | Buccal Swab | | | | | | | | | | | | | |
| ID | HLA | Allele 1 | Allele 2 | Allele 1 | Allele 2 | Allele 1 | Allele 2 | Allele 1 | Allele 2 | Allele 1 | Allele 2 | Allele 1 | Allele 2 | Allele 1 | Allele 2 |
| A1 | DRB1* | 04:01 | 07:01 | 04:01 | 07:01 | 04:01 | 07:01 | 04:01 | 07:01 | 04:01 | 07:01 | 04:01 | 07:01 | 04:01 | 07:01 |
| A2 | DRB1* | 03:01 | 15:01 | 03:01 | 15:01 | 03:07 | 15:01 | 03:01 | 15:01 | 03:01 | 15:01 | 03:01 | 15:01 | 03:07 | 15:01 |
| A3 | DRB1* | 08:32 | 15:01 | 08:32 | 15:01 | 08:32 | 15:01 | 08:32 | 15:01 | 08:32 | 15:07 | 08:32 | 15:01 | 08:32 | 15:01 |
| A4 | DRB1* | 04:03 | 09:01 | 04:03 | 09:01 | 04:03 | 09:01 | 04:03 | 09:01 | 04:03 | 09:01 | 04:03 | 09:01 | 04:03 | 09:01 |
| A5 | DRB1* | 08:02 | 13:03 | 08:02 | 13:03 | 08:02 | 13:03 | 08:02 | 13:03 | 08:02 | 13:03 | 08:02 | 13:03 | 08:02 | 13:03 |
| A6 | DRB1* | 03:01 | 11:03 | 03:01 | 11:03 | 03:07 | 11:03 | 03:01 | 11:03 | 03:01 | 11:03 | 03:01 | 11:03 | 03:01 | 11:03 |
| A7 | DRB1* | 04:07 | 13:01 | 04:07 | 13:01 | 04:07 | 13:01 | 04:07 | 13:01 | 04:39 | 13:02 | 04:07 | 13:01 | 04:07 | 13:01 |
| A8 | DRB1* | 04:07 | 15:02 | 04:07 | 15:02 | 04:07 | 15:02 | 04:07 | 15:27 | 04:07 | 15:02 | 04:07 | 15:02 | 04:07 | 15:27 |
| A9 | DRB1* | 01:01 | 13:02 | 01:01 | 13:02 | 01:01 | 13:02 | 01:01 | 13:02 | 01:01 | 13:02 | 01:01 | 13:02 | 01:01 | 13:02 |
| A10 | DRB1* | 01:01 | 13:01 | 01:01 | 13:01 | 01:01 | 13:01 | 01:01 | 13:01 | 01:01 | 13:01 | 01:01 | 13:01 | 01:01 | 13:01 |
| A11 | DRB1* | 04:01 | 15:01 | 04:01 | 15:01 | 04:01 | 15:01 | 04:01 | 15:01 | 04:01 | 15:01 | 04:01 | 15:01 | 04:01 | 15:01 |
| A12 | DRB1* | 07:01 | 08:01 | 07:01 | 08:01 | 07:01 | 08:01 | 07:01 | 08:01 | 07:01 | 08:01 | 07:01 | 08:01 | 07:01 | 08:01 |

TABLE 12

Agreement Between HLA-Chip and LabCorp: Raw Buccal
Swabs, Scope Mouthwash vs. Matched Purified DNA

| Gene | Percentage of Samples having: | Raw Buccal Swab | | Purified DNA Buccal Swab | | Raw Mouthwash | | Purified DNA Mouthwash | |
|---|---|---|---|---|---|---|---|---|---|
| | | Allele 1 | Allele 2 | Allele 1 | Allele 2 | Allele 1 | Allele 2 | Allele 1 | Allele 2 |
| HLA-A | High Resolution Match | 75 | 75 | 100 | 83.3 | 100 | 83.3 | 91.7 | 83.3 |
| | Low Resolution Match | 25 | 25 | 0 | 16.7 | 0 | 16.7 | 8.3 | 16.7 |
| HLA-B | High Resolution Match | 91.7 | 91.7 | 83.3 | 83.3 | 100 | 100 | 91.7 | 100 |
| | Low Resolution Match | 8.3 | 8.3 | 16.7 | 16.7 | 0 | 0 | 8.3 | 0 |
| HLA-DRB1 | High Resolution Match | 100 | 100 | 83.3 | 91.7 | 100 | 100 | 91.7 | 100 |
| | Low Resolution Match | 0 | 0 | 16.7 | 8.3 | 0 | 0 | 8.3 | 0 |

TABLE 13

Agreement Between HLA-Chip and LabCorp: Raw Oragene vs. Matched Purified DNA

| Gene | Percentage of Samples having: | Raw Oragene OG-510 | | PI Raw Oragene OG-510 | | Purified DNA Oragene OG-510 | | Raw Oragene ON-500 | | PI Raw Oragene ON-500 | | Purified DNA Oragene ON-500 | |
|---|---|---|---|---|---|---|---|---|---|---|---|---|---|
| | | Allele 1 | Allele 2 | Allele 1 | Allele 2 | Allele 1 | Allele 2 | Allele 1 | Allele 2 | Allele 1 | Allele 2 | Allele 1 | Allele 2 |
| HLA-A | High Resolution Match | 91.7 | 58.3 | 75 | 58.3 | 91.7 | 75 | 83.3 | 75 | 83.3 | 75 | 100 | 66.7 |
| | Low Resolution Match | 8.3 | 41.7 | 25 | 41.7 | 8.3 | 25 | 16.7 | 25 | 16.7 | 25 | 0 | 33.3 |
| HLA-B | High Resolution Match | 91.7 | 91.7 | 100 | 100 | 100 | 91.7 | 100 | 91.7 | 100 | 100 | 91.7 | 83.3 |
| | Low Resolution Match | 8.3 | 8.3 | 0 | 0 | 0 | 8.3 | 0 | 8.3 | 0 | 0 | 8.3 | 16.7 |
| HLA-DRB1 | High Resolution Match | 100 | 100 | 83.3 | 100 | 100 | 91.7 | 91.7 | 83.3 | 100 | 100 | 83.3 | 91.7 |
| | Low Resolution Match | 0 | 0 | 16.7 | 0 | 0 | 8.3 | 8.3 | 16.7 | 0 | 0 | 16.7 | 8.3 |

Also included in these Tables, for each sample type and HLA-Typing reaction is a parameter called "Microarray Signal Strength" which corresponds to the total fluorescence intensity, summed over all probe hybridization reactions within a microarray. Such total signal intensity is a function of the amount of Cy-3 labeled target applied to the microarrays, and serves as a test for the uniformity of sample yield of the secondary PCR reaction used to generate the hybridization target.

As was done in FIGS. 13A-13F, 14A-14F and 15A-15F, the data in Tables was obtained via linear regression analysis, for the entire set of 12 volunteers, all 10 sample types and for the 3 HLA microarray tests, for a total of 360 independent microarray determinations. Values have been color-coded based on the measured correlation (R2) between data obtained from raw samples and purified DNA. The slope assocated with the pairwise correlation (purified vs. raw) and the measured Microarray Signal Strength have also been listed for each purified/raw sample pair. As discussed above, the Microarray Signal Strength for each set of measurements is a parameter that is proportional to the amount of sample added to the array for hybridization analysis.

If the tandem PCR-based raw sample genotyping technology described here were to work perfectly, the microarray data for all 12 volunteers, 10 sample types and each of the 3 gene tests should be identical: i.e. Slope=1, R2=1, Microarray Signal Strength=Constant. To assess measured deviations from such ideal values, we have calculated the mean and standard deviation of those parameters, for each of the columns in Tables 4-5 presented as the bottom two rows. Mean Slopes are seen to be in the 0.97-1.15 range, mean R2 in the 0.86-0.91 range and mean microarray Signal Strength in the 91-110 range. Given the relatively small sample size, the observed agreement with ideal hybridization behavior and the relatively small variance about the mean (SD=10%-40%) for these microarray parameters suggests that the present tandem PCR approach to raw sample genotyping has done an adequate job of obviating the effect of sample impurity and uncontrolled variation in DNA concentration within this set of 12×10×3=360 measurements.

The generally-good similarity seen for raw vs. purified microarray hybridization data (FIGS. 13-15, Tables 4-5) suggests that HLA-Types obtained from these raw samples might be similar to HLA-Types obtained from the corresponding matched purified DNA. Such HLA-types have been determined from these microarray hybridization data using Ricimer software and have been displayed in Tables 6-11, which present a summary of such microarray-based A, B & DRB1 HLA-typing for all 12 volunteers and 10 sample types. For all twelve volunteers, HLA-Typing has also been determined from matched purified DNA at an ASHI-certified national reference laboratory (Lab Corp, Raleigh N.C.).

In Tables 6-11, perfect HLA-Typing matches at 4-digit accuracy relative to the LabCorp standard data are marked in green; matches at lower (2-digit, serological) accuracy are marked in blue. Overall, microarray HLA analysis of all raw and the corresponding matched purified DNA samples show generally-good agreement with standardized genotyping by sequencing performed independently on purified DNA from the same twelve volunteers (Lab Corp). The correlation is summarized in Tables 12-13.

EXAMPLE 5

PCR Reactions for HLA-typinq from Raw Blood in the Fluid State and from Raw Blood that was Allow to Dry on Guthrie Cards Raw anonymized raw blood was obtained from Memorial Blood Labs, Minneapolis Minn. and was stored frozen at −20° C. until needed. Thawed raw blood was used directly as the template for the primary, locus-specific HLA PCR reactions required for HLA-Chip analysis. The corresponding dried blood samples were prepared by pipetting fresh, never frozen, blood onto standard Whatman-GE Guthrie cards, followed by 72 hrs of drying at 25° C. in a laminar flow hood, then storage in a sealed pouch, at 25° C., thereafter. For dried blood on Guthrie cards, a 2 mm circular punch was excised from the blood card, to which was added 100 µl of 100 mM Boric acid and 1 mM EDTA at pH 7.5. The punch was then heated for 2 hrs 70° C. to rehydrate the blood spot, and to elute the contents of blood spot into solution. The resulting fluid phase was then mixed by pipetting. The rehydrated punches were then stored at −20° C. until analysis.

For both raw and rehydrated dried blood, 1 µl of sample was used without subsequent purification as the template for PCR. A first PCR amplification was performed via the Finnzymes PHUSION® Blood Direct kit. 1 µl of that primary, locus specific PCR product was then applied directly as template for the secondary, self limiting, exon-specific PCR reactions. One microliter of each of the resulting 2° PCR reaction product was then loaded onto a standard acrylamide gel. HLA-A exons 2 and 3 and HLA-DRB1 exon 2 (FIG. 5A) and HLA-B exons 2 and 3 (FIG. 5B-5C) were visualized by Amresco EZ-Vision DNA Dye. Positive controls on the gel refer to the product of the same tandem HLA PCR reactions, but instead using 10 ng of highly-purified Roche DNA as the original sample input. As seen, the amount of final 2° amplicon obtained from 1 µl of raw blood, is nearly independent of the sample used in the reaction, and similar in specificity & mass yield, to the amplified HLA product obtained from 10 ng of purified Roche DNA.

EXAMPLE 6

Detailed PCR Reaction Protocols

The tandem PCR reaction described above was performed on raw samples or purified DNA to yield A, B, and DRB1 amplicons. The 1° PCR reaction employed an input volume of 1 µl, throughout: undiluted purified DNA (@10 ng), undiluted raw buccal swab fluid, a 1:20 dilution of the resuspended Scope mouthwash pellet, or a 1:50 dilution of raw ORAGENE™-stabilized saliva (both kits). A 1:50 dilution was required to obtain an HLA-A genotype for sample A3. The total 1° PCR reaction volume was held at 25 µL: 1 µl of raw or purified sample plus 2.5 µl (1×) Roche 10×PCR Buffer, 1.5 µl (1.5 mM) 25 mM MgCl$_2$, 0.8 µl (0.16 mg/mL) 5 mg/mL BSA, 2 µl (0.4 µM) 5 µM primary primer set, 0.5 µl (200 µM) 10 mM dNTPs, 0.2 µl (1U) 5U/µl Roche FastStart Taq DNA Polymerase. 1° PCR cycling conditions were 94° C. for 4 minutes, followed by 35 cycles of [98° C. for 1 minute, 67° C. (HLA-A) 69° C. (HLA-B, -DRB1) for 1 minute and 72° C. for 1 minute] with a final 72° C. extension for 7 minutes.

Throughout, the 2° PCR reaction used 2.5 µl of the unprocessed 1° PCR reaction product as its sample input:diluted 1:100 for all samples, except for raw buccal swab eluate, which was diluted 1:10. The 2° PCR Master Mix was 50 µl of 5 µl (1×) Applied Biosytems GeneAmp 10×PCR Gold Buffer II, 6 µl (3.0 mM) 25 mM MgCl$_2$, 1.6 µl (0.16 mg/mL) 5 mg/mL BSA, 4 µl (0.4 µM) 5 µM secondary primer set, 1 µl (200 µM) 10 mM dNTPs, 0.8 µl (4U) 5U/µl AMPLITAQ GOLD® DNA Polymerase, and 2.5 µl of diluted primary PCR product. Secondary PCR was performed at 94° C. for 2 minutes, followed by 40 cycles at [98° C. for 30 seconds, 68° C. for 30 seconds and 72° C. for 30 seconds] with a final extension at 72° C. for 7 minutes.

EXAMPLE 7

PCR Reactions for HLA-Typing from Rehydrated Buccal Swabs

De-identified buccal swabs were procured from local donors. Four swabs were collected from each participant by vigorously swabbing up and down twenty times per each quadrant of the mouth and placed into 15 mL conical tubes. Whole mouth swabs were taken from 12 individuals: A1-A12. Samples were dried for 72 hours under laminar flow hood. Dried swabs were then rehydrated in 150 µl of rehydration buffer (100 mM Borate+1 mM EDTA) and solubilized at 70° C. for 2× hours. The resulting fluid phase was then mixed by pipetting. The rehydrated swabs were then stored at −20° C. until analysis. A nested (tandem) PCR reaction was then performed for each of the HLA loci of interest. 1 µl of raw swab eluate was used for a primary 25 µL PCR reaction employing Roche Taq polymerase'. The subsequent (secondary) PCR was then performed upon 2.5 µL of the primary amplicon product in a total PCR reaction volume of 25 µL, also employing Roche Taq polymerase. Upon completion, the residual sample (up to half the recovered volume) was extracted via QIAamp DNA Blood Mini Kit (Qiagen catalog #51104). The resulting purified DNA was run on the same microarray HLA-typing platform. Unpurified and purified buccal DNA were analyzed via microarray technology for HLA typing. The matched, de-identified DNA from buccal swabs was compared to HLA types obtained on the raw, unpurified samples via gel electrophoresis. One microliter of each of the resulting 2° PCR reaction product was then loaded onto a standard acrylamide gel.

Figure 6A:
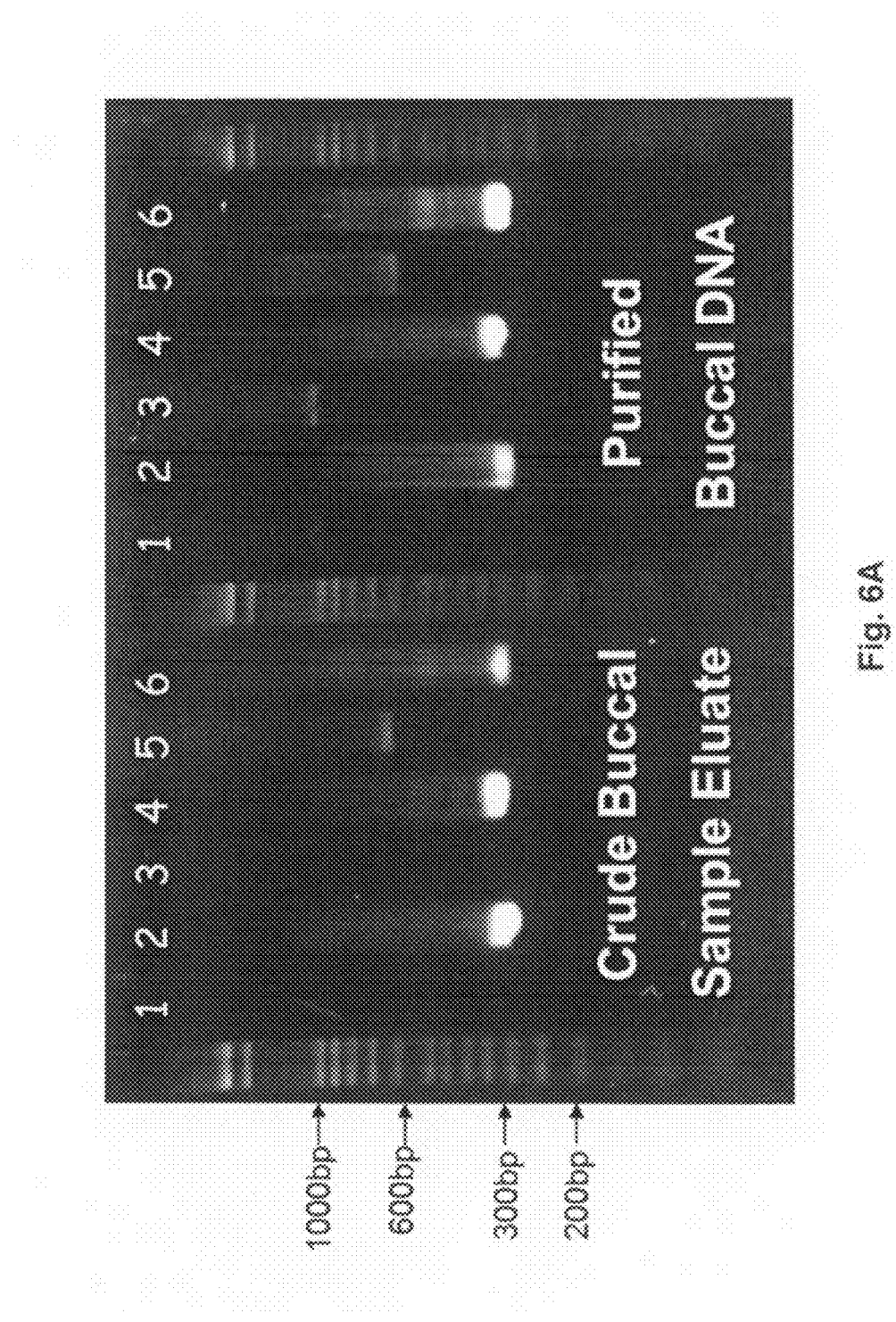
Figure 6C:
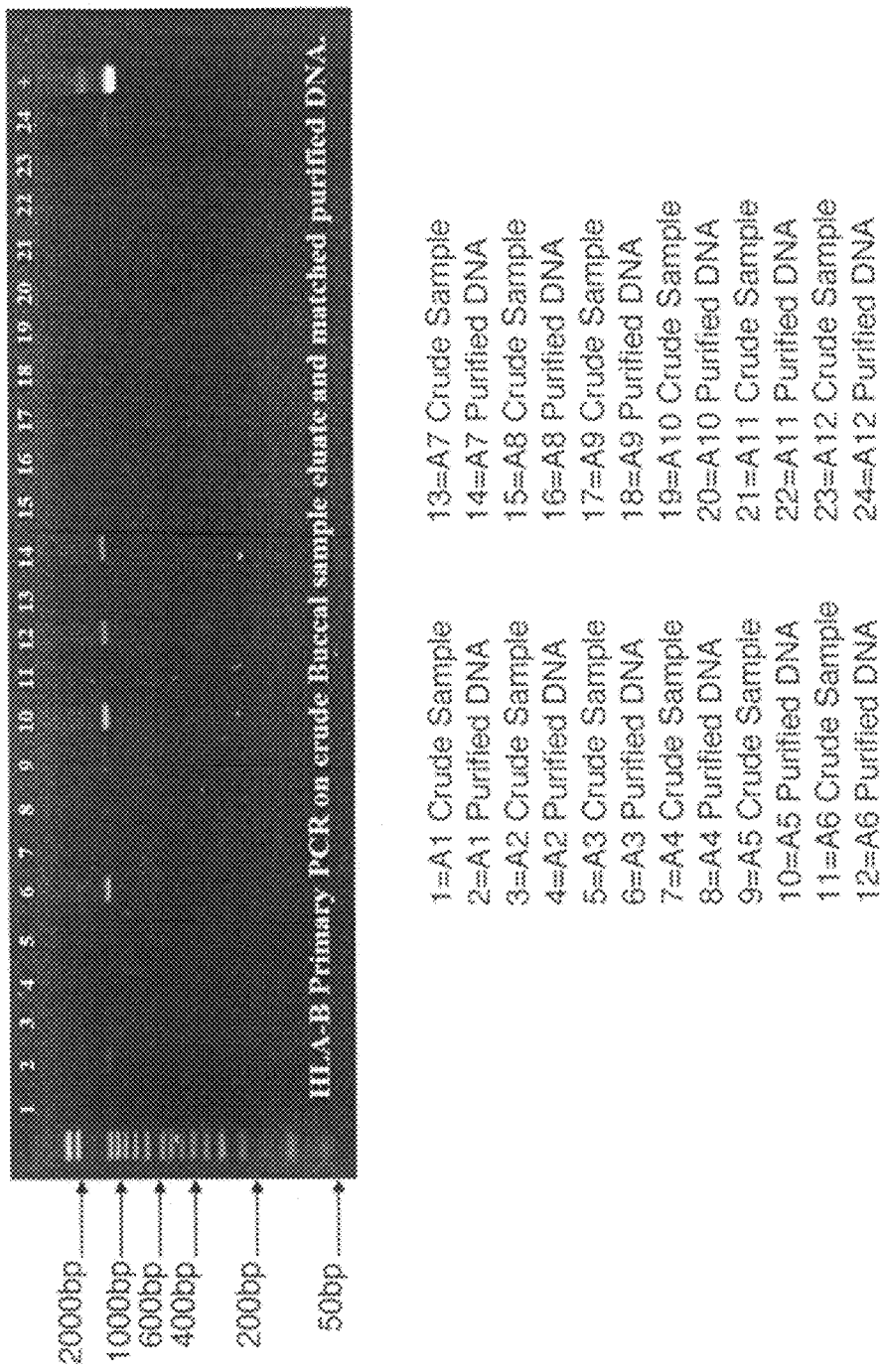
Figure 6D:
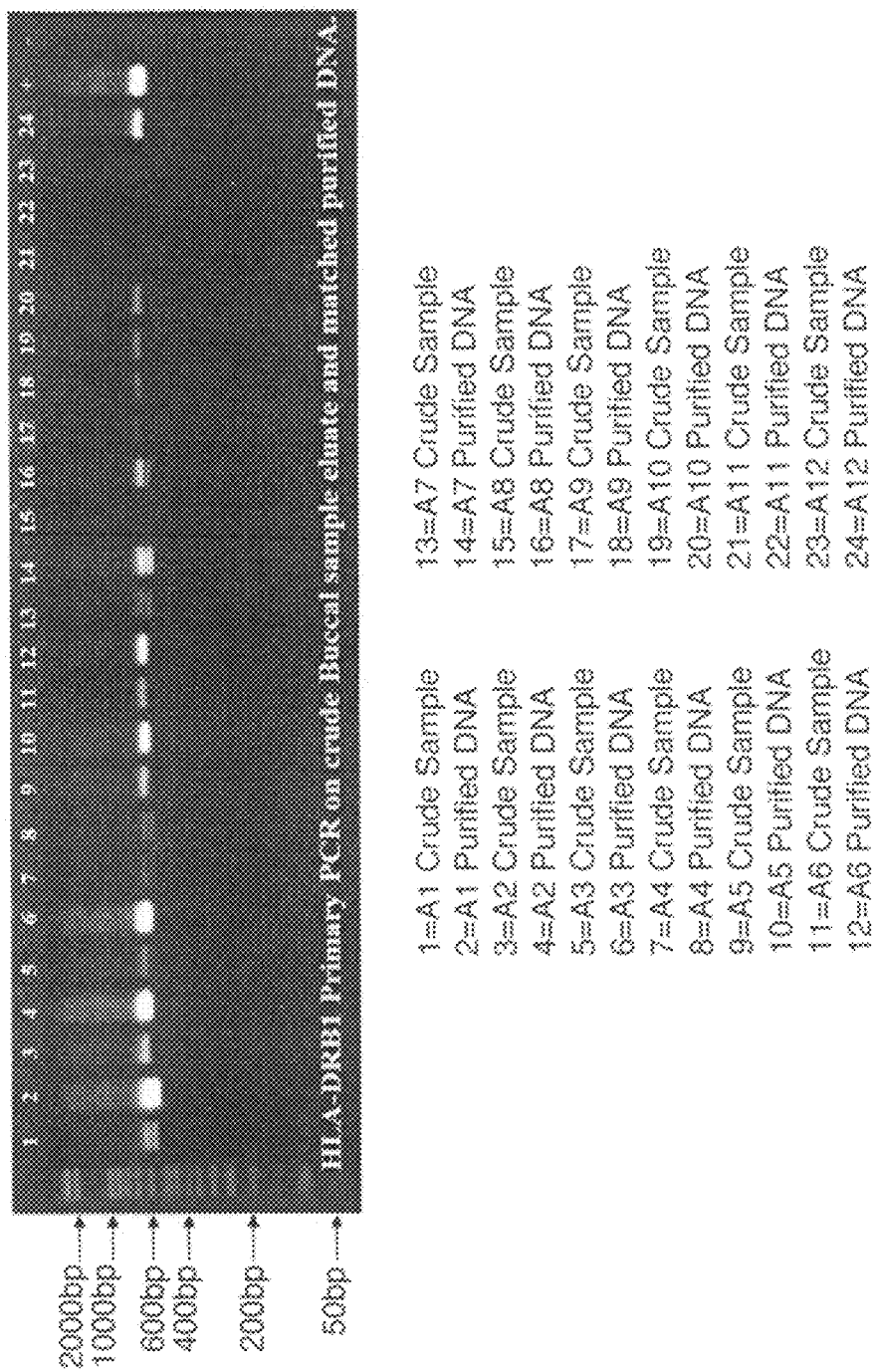
Figure 6E:
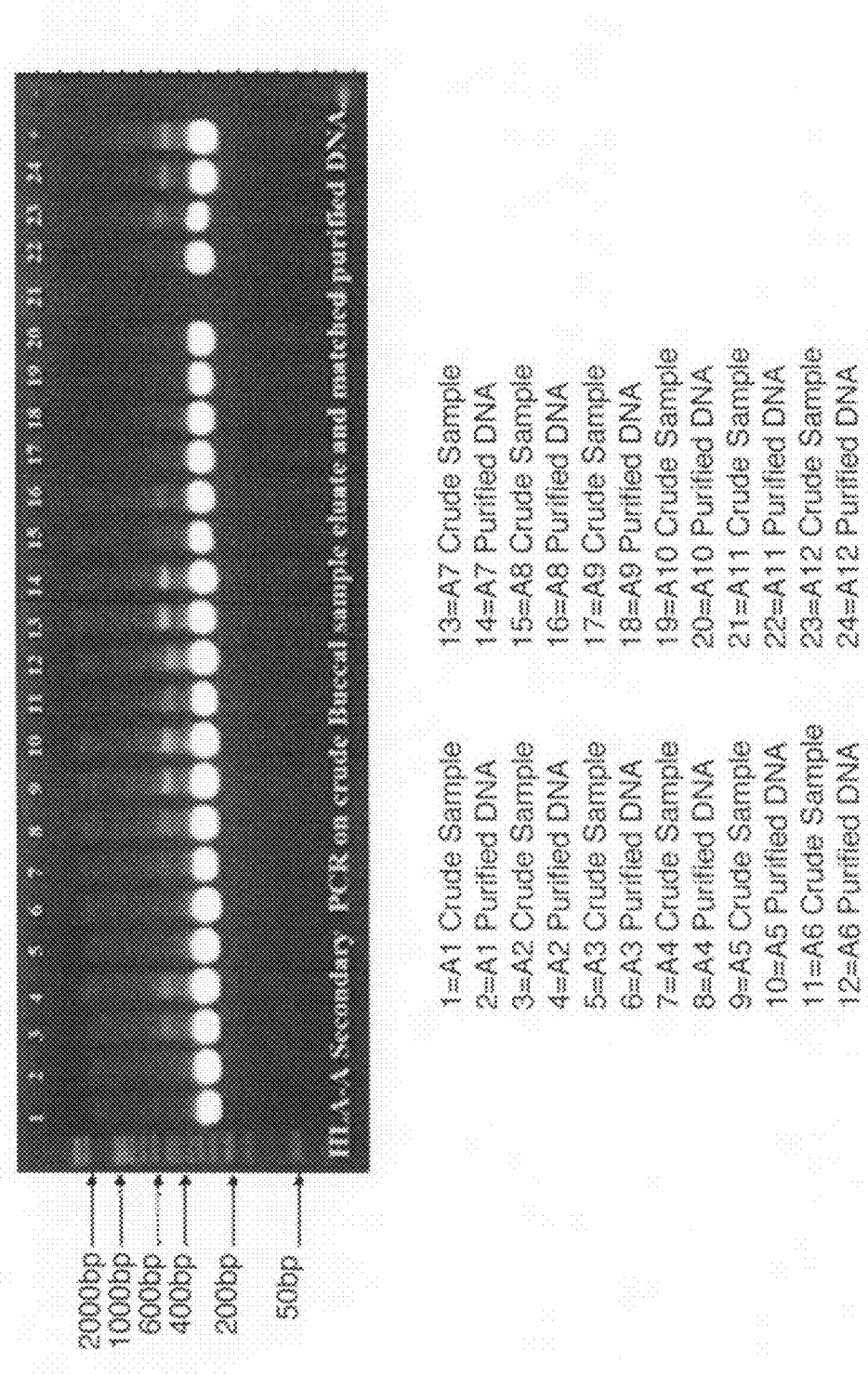
Figure 6F:
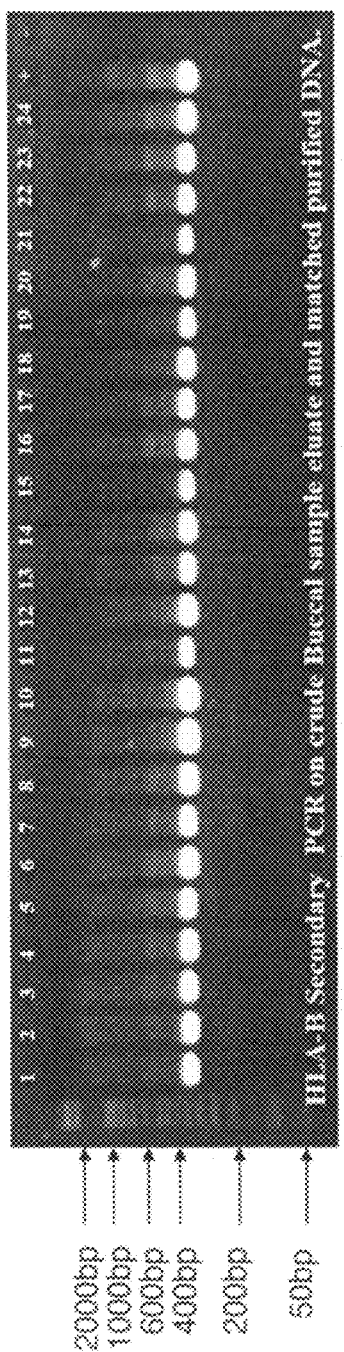

Primary locus specific PCR products as well as the products of the secondary exon specific reaction set (performed as a single multiplex reaction) were displayed in FIG. 6A (left) along with identical reaction products obtained from 10 ng of purified DNA obtained from the sample (right). Bands were visualized by Amresco EZ-Vision DNA Dye. As seen, the amount of final 2° amplicon obtained from 1 µL of raw swab eluate, is similar in specificity & mass yield, to the amplified HLA product obtained from 10 ng of purified DNA from the same sample. FIGS. 6B-6G display the product of the tandem PCR reactions performed on raw cheek swabs from a total of 12 donors. FIGS. 6B-6D display the primary PCR reactions specific for HLA-A, HLA-B & HLA-DRB1 for these 12 raw buccal swab samples, while FIGS. 6E-6G display the secondary PCR reactions specific for HLA-A, HLA-B & HLA-DRB1 for the sample 12 raw buccal swab samples. As can be seen, although the yield of primary PCR product is highly variable among the set of 12 raw, re-hydrated buccal swabs samples (FIGS. 6B-6D) the subsequent secondary PCR reaction has generated a series of amplified exons which are nearly identical in yield and specificity, among the set of 12 raw buccal swab specimens (FIGS. 6E-6G).

EXAMPLE 8

Multiplex PCR from Purified DNA, for Several Genes in Parallel

HLA locus-specific amplicons for HLA-A plus HLA-DRB1, and HLA-B and HLA-DRB1 are generated from 1 µl whole fluid blood (FIG. 7A-7B, 7G-7H) via the PCR reaction using FastStart Taq DNA Polymerase under the following conditions: 1×PCR Buffer (without Mg$^{++}$), 1.5 mM MgCl$_2$, 0.16 mg/ml BSA (fraction V), 0.05 µM each dNTP, 400 nM of each locus-specific primer for each of the genes being amplified in parallel, and 1 unit of Taq in a total reaction volume of 25 µl. These reactions are cycled using the following protocol: initial denaturing at 98° C. for 5 minutes followed by 35 cycles of i) denature at 98° C. for 5 sec, ii) anneal at 70° C. for 1 minute, and iii) extend at 72° C. for 30 sec, then a final 72° C. extension for 7 minutes.

Figure 7A:
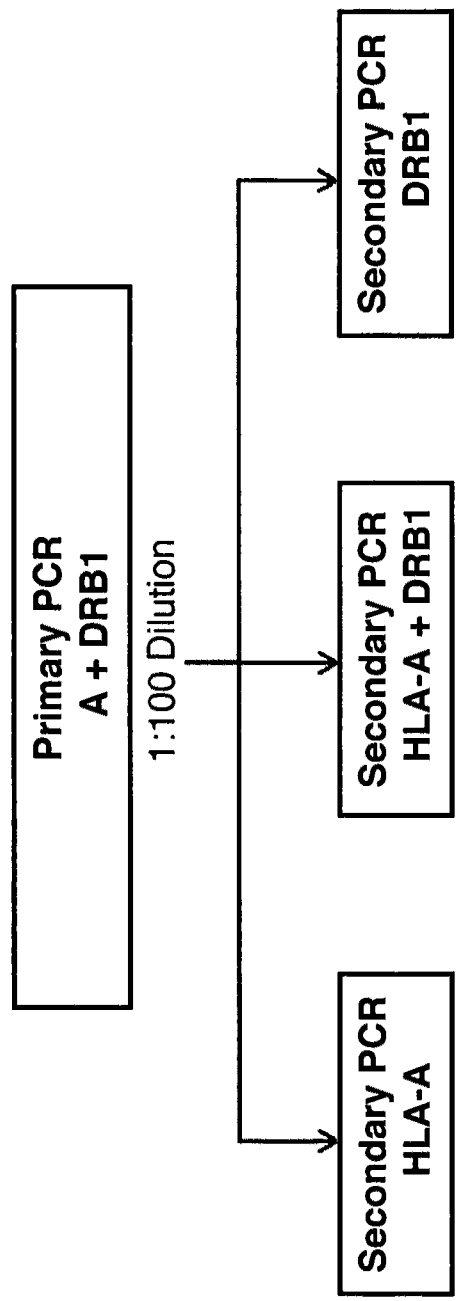
FIGS. 7A-7L show Tandem PCR amplification of multiple HLA genes in parallel: HLA-A & HLA-DRB1. Locus-specific multiplex and exon specific multiplex HLA-PCR reactions were performed on a set of 5 samples retrieved from the UCLA Immunogenetics reference panel for HLA Class I.
Figure 7B:
Figure 7C:
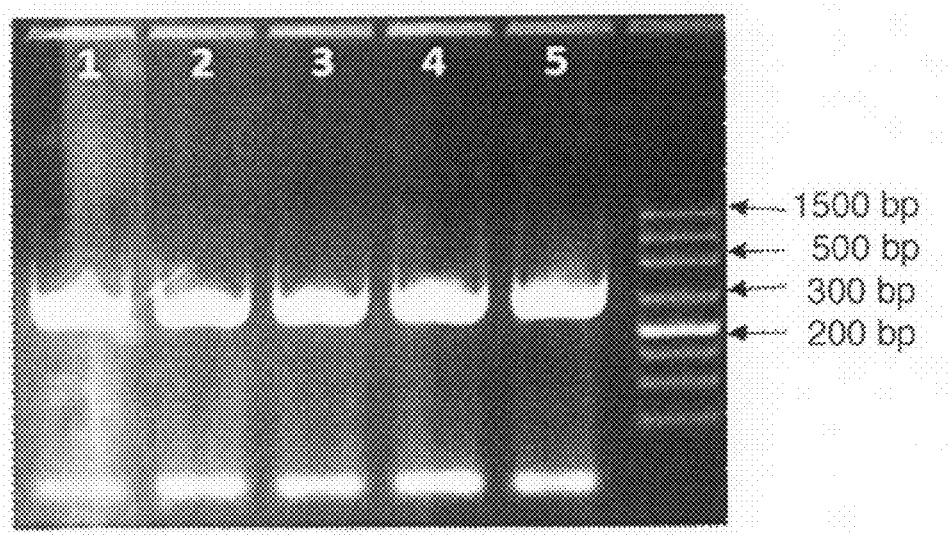
Figure 7D:
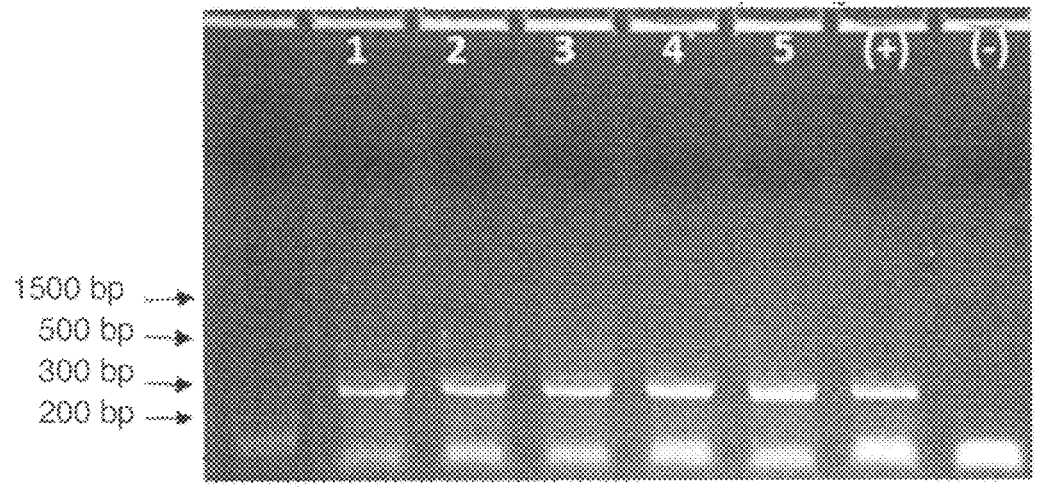
Figure 7E:
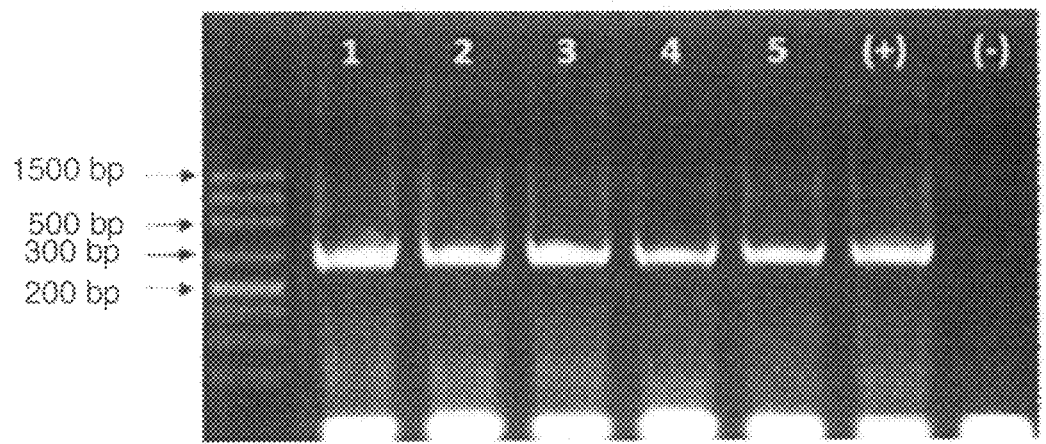
Figure 7F:
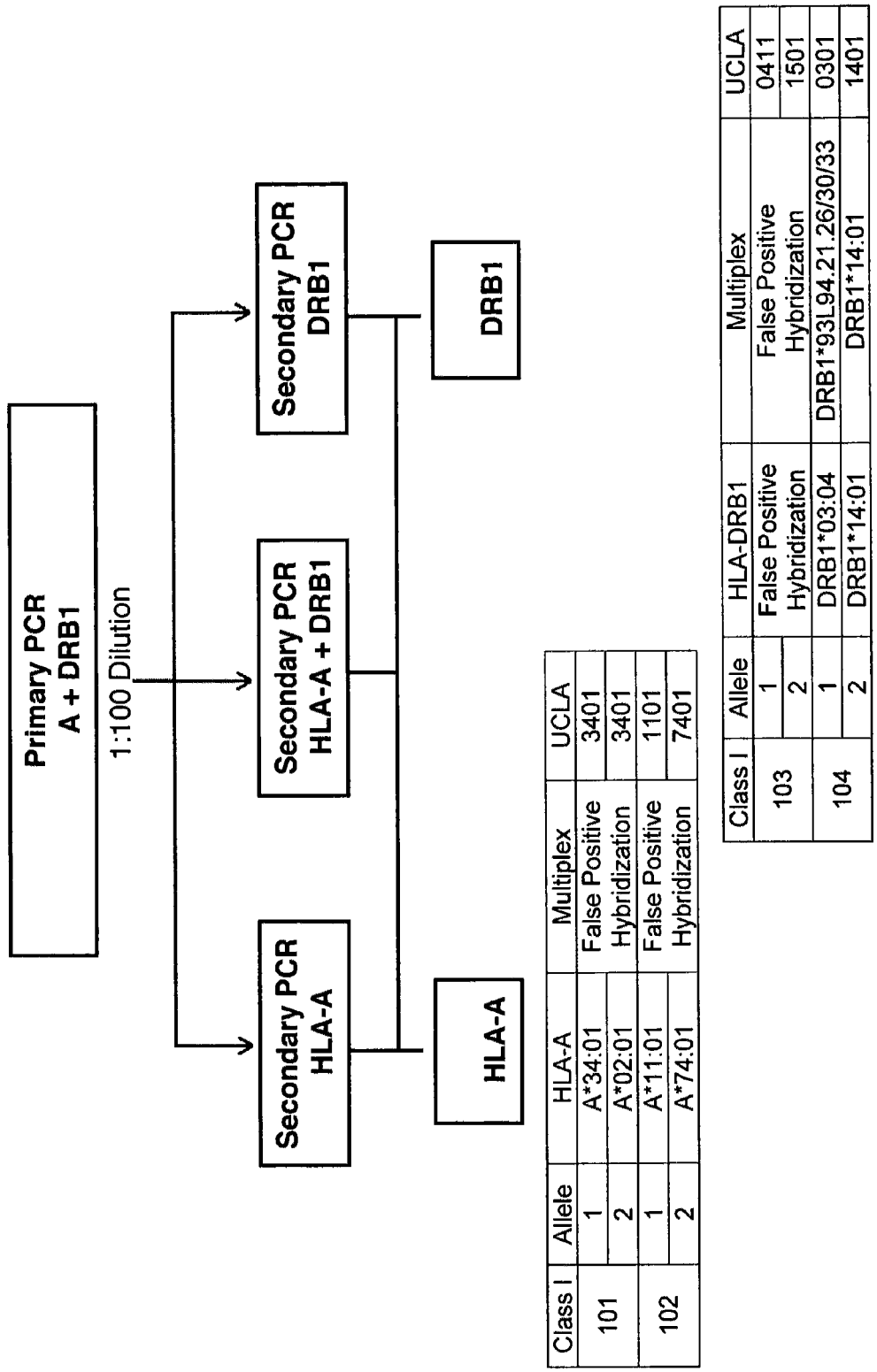
Figure 7G:
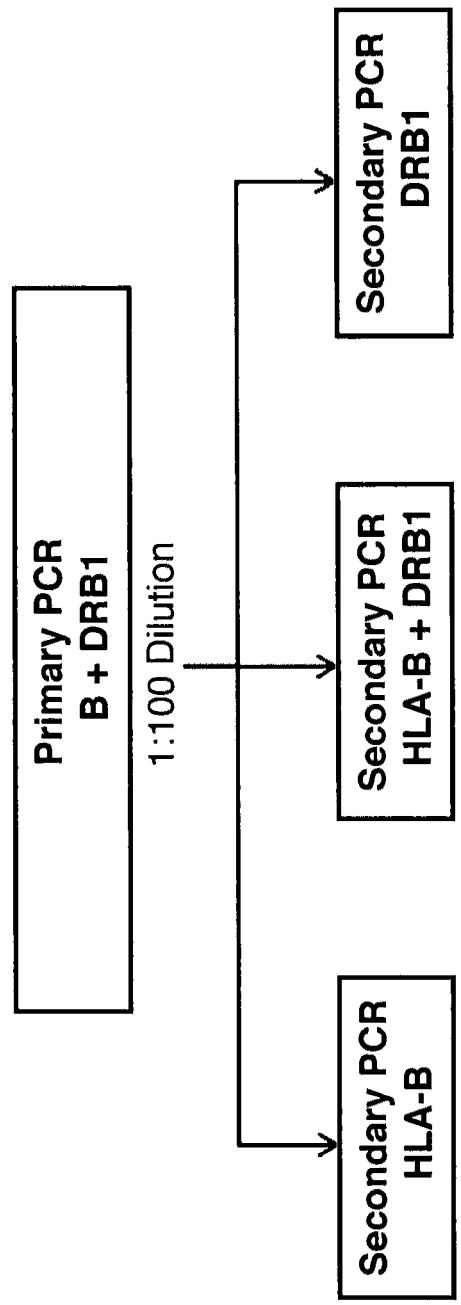
Figure 7H:
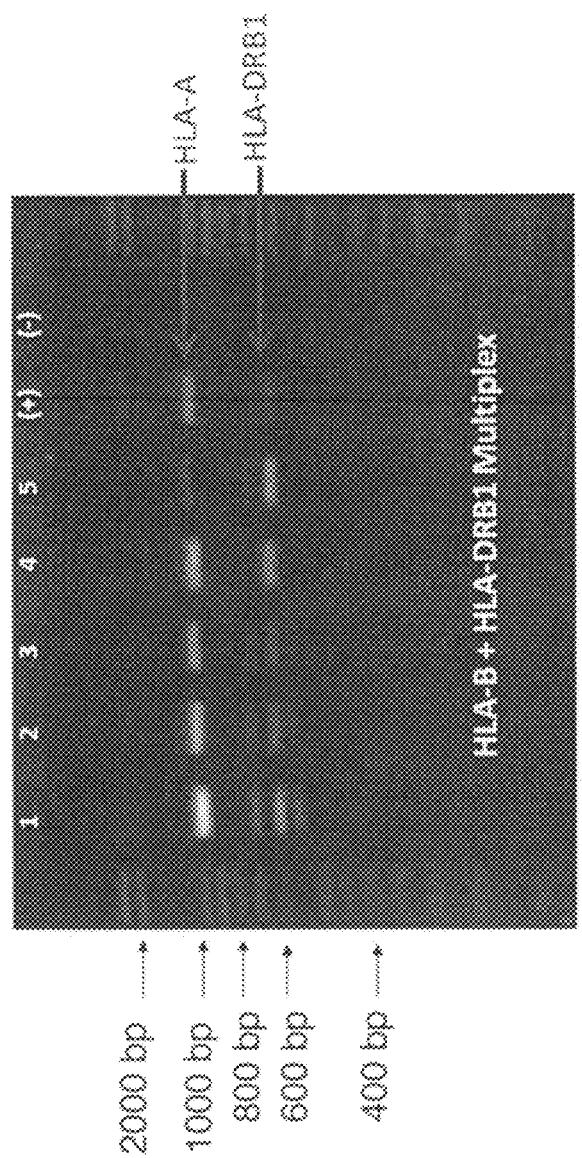
Figure 7I:
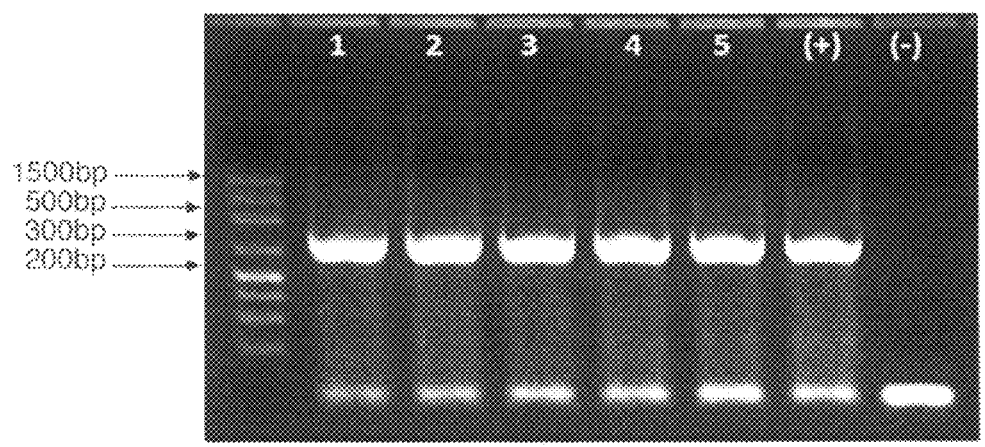
Figure 7J:
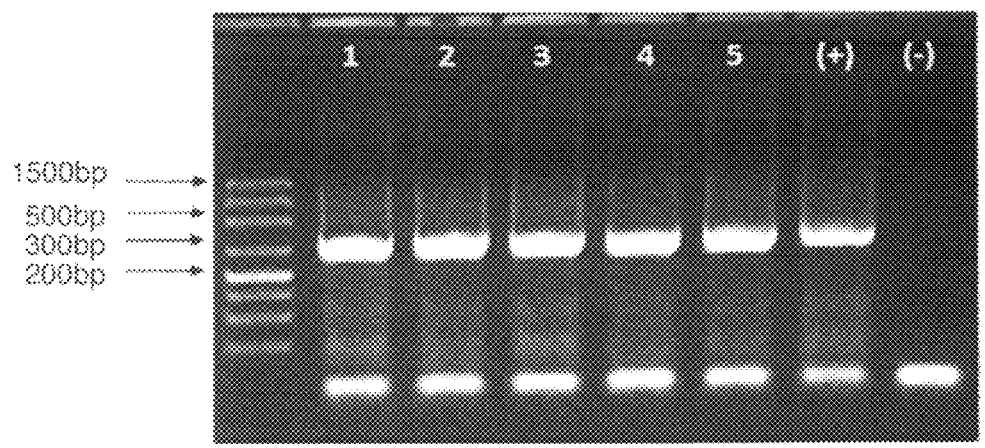
Figure 7K:
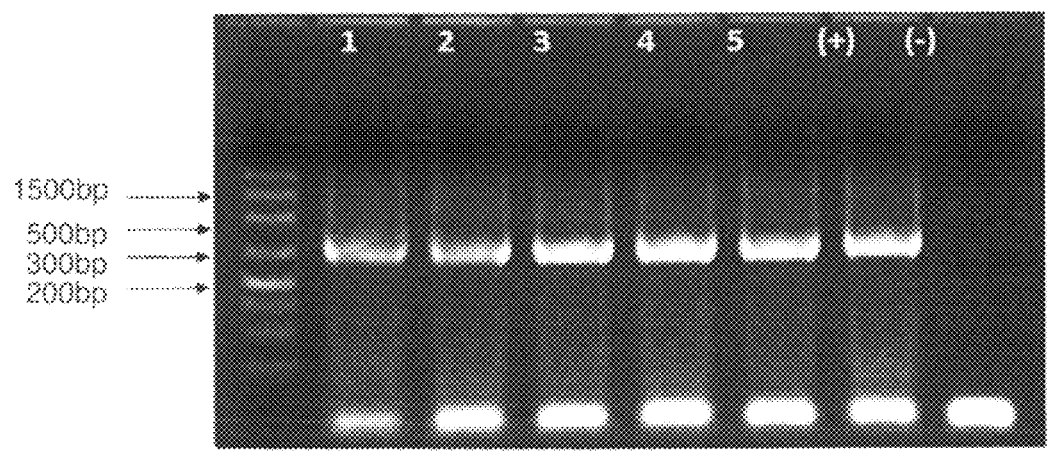
Figure 7L:
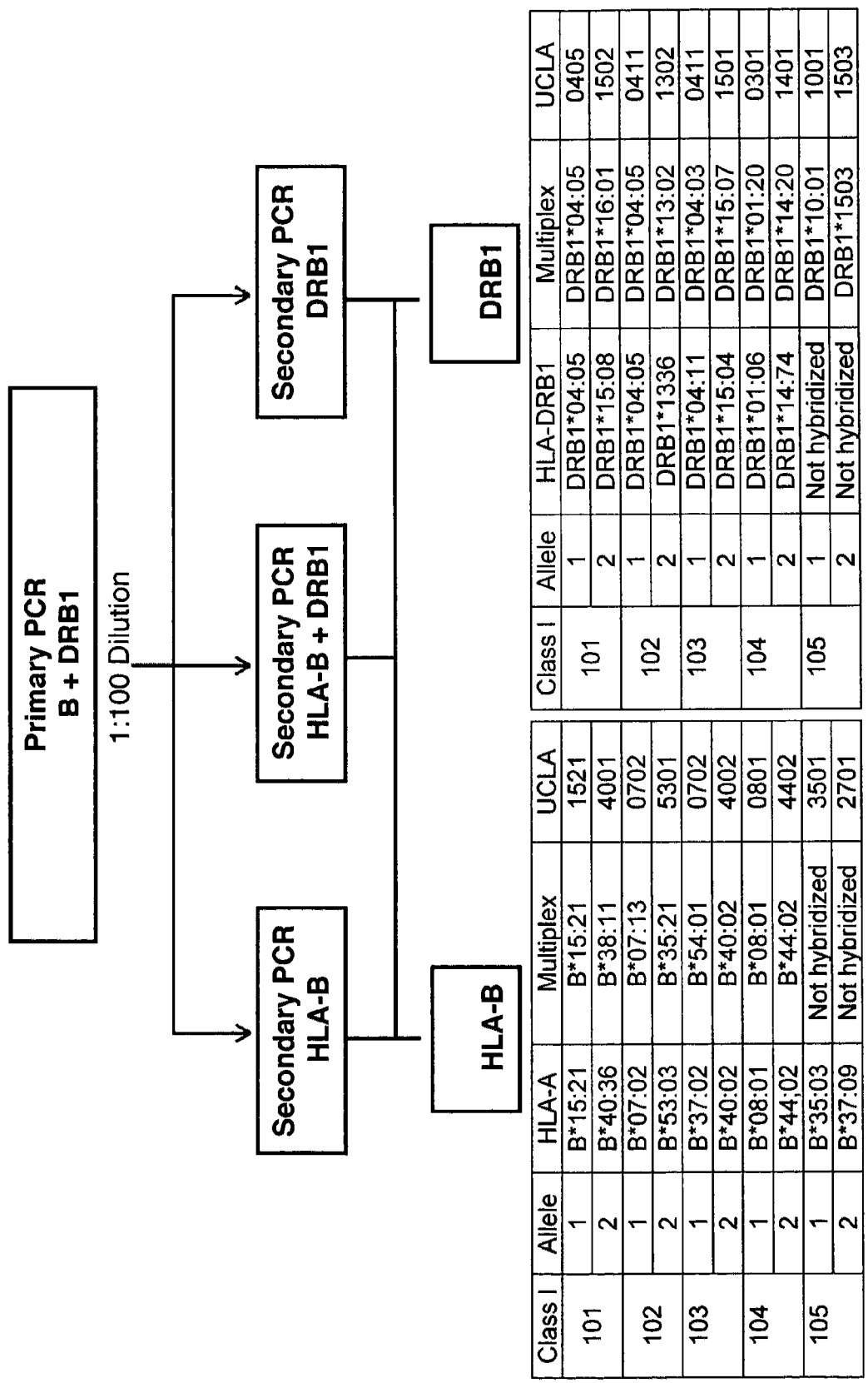
Figure 9:
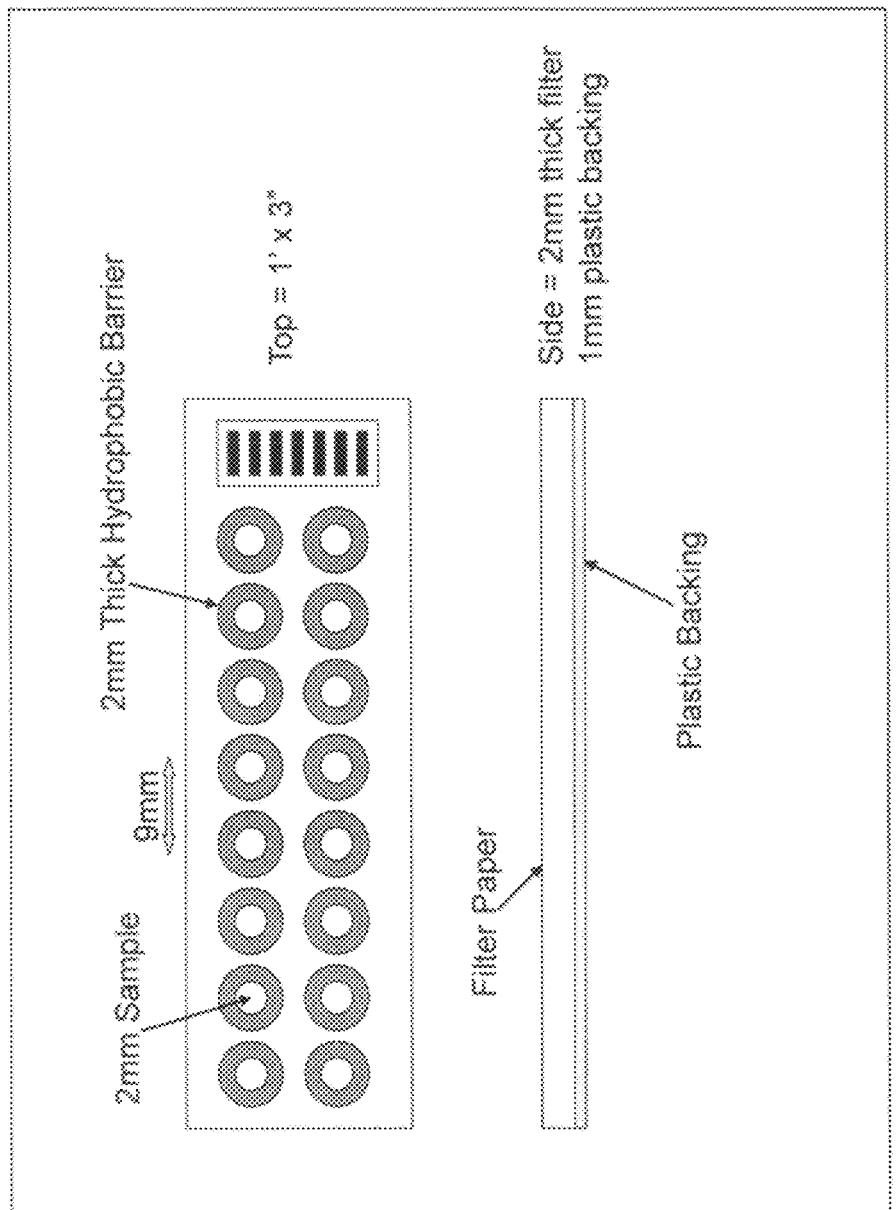
FIG. 9 shows use of a Guthrie card for sample recovery. Up to 16 umbilical cord blood specimens may be collected per 1"×3" paper Guthrie card. The 2 mm cylindrical sample elements are fluidically isolated in the Guthrie card by embossing 4 mm rings into the paper with a hydrophobic paint, and backing the card with plastic.

The product from the locus-specific reactions of HLA-A and DRB1 performed in parallel and HLA-B and HLA-DRB1 also performed in parallel (FIGS. 7B, 7H), diluted 1:100 in molecular biology grade water, are used as a template for subsequent exon-specific "nested" PCR reactions (FIGS. 7C-7E, 7I-7K). As shown on the diagrams of FIGS. 7A and 7G the dilution of the locus-specific PCR were used as template for an exon-specific PCR reaction where either only HLA-A, HLA-DRB1 or HLA-B exons were amplified. A second reaction can be performed were the exons 2 and 3 for HLA-A or HLA-B can be simultaneously amplified with exon 2 from HLA-DRB1. The above mentioned PCR reactions are performed using Applied Biosystems' (Foster City, Calif.) AMPLITAQ GOLD@ DNA Polymerase in a 100 µl reaction volume with the following components: 5 µl of 1:100 diluted locus specific PCR product, 1×PCR Buffer II, 1.5 mM $MgCL_2$, 0.16 mg/ml BSA (fraction V), 0.2 mM each dNTP, 400 nM each primer of interest, and 4 units of AMPLITAQ GOLD@ DNA Polymerase. Cycling conditions are: initial denaturation at 94° C. for 2 minutes followed by 40 cycles of (i) denaturing at 98° C. for 30 seconds, (ii) annealing at 68° C. for 30 seconds, and (iii) extension at 72° C. for 30 seconds, then a final extension step of 72° C. for 7 minutes. Exon-specific PCR primers are labeled with Cyannine 3 dye to facilitate detection of positive hybridization events by laser excitation/emission in a microarray scanner such as a ProScan Array HT (Perkin-Elmer, Waltham, Mass.). Hybridization of the genes amplified in parallel are performed where the products of the secondary amplification of exons 2 and 3 of HLA-A and HLA-B, and exon 2 of HLA-DRB1 can be hybridized to the corresponding HLA-Chips obtaining successful matching genotypes in preliminary data collection (FIG. 7F) In addition, the product of the secondary PCR of genes amplified in parallel such as HLA-A and HLA-DRB1 can be hybridized to either an HLA-A chip or an HLA-DRB1 chip, the same applies for the secondary PCR product of HLA-B and HLA-DRB1 multiplex (FIG. 7L).

EXAMPLE 9

Multiplex PCR of DNA from Raw Unpurified Fecal Matter for Several Genes in Parallel Analysis of the DNA complement of feces has become very important for the clinical and research analysis of microbial diversity in feces, and the relationship between that diversity and human or animal diseases. It is well known that, among prokaryotic microbes, individual microbes can be identified based on variation in the sequence of their 16S gene and the 16S rRNA expressed from it. It is also well known that 16S DNA can be amplified using "universal" PCR primer sets which, when used as a set, will amplify all members of the prokaryotic 16S RNA gene family, so that the amplified DNA can be analyzed by sequence analysis on microarrays or by chemical or biochemical sequencing methods. Although such 16S DNA sequence analysis can be performed by all such methods to yield an estimate of the type of prokaryotic microbe in a specimen, that kind of analysis in feces has proven difficult to implement in large clinical or field studies, due to the cost and health risks associated with DNA purification from fecal matter.

It is well known that the microbial content of ordinary human stool comprises $10^{+10}$ up to $10^{+11}$ microbes per CC, which is nearly 1% by mass. Based on that very high cell density, the density of 16S gene DNA in those same samples will therefore also exceed $10^{+10}$ up to $10^{+11}$ 16S gene segments per CC, or about $10^{+7}$ copies per µl. The tandem PCR reactions of the kind described in Examples 1-9 function well on about 10 ng human DNA (about 2,000 copies) per µl. Thus, at ordinary microbial density in feces, 16S DNA is presented at a copy number density that is at least 1,000 times greater than displayed in Examples 1-9 for raw blood or buccal swabs. Based on that very high copy number, it is therefore possible to use the technology described herein to perform 16S DNA based microbial diversity analysis upon unpurified fecal matter:

Step 1. Obtain about 10 µl (about 10 mm$^3$) of feces by contact transfer with a stick or tip.

Step 2. Dissolve the feces in about 100 µl of water.

Step 3. Take about 1 µl of diluted feces suspension and perform a primary 16S PCR reaction with a universal 16s PCR primer set.

Step 4. Take 1 µl of the primary PCR amplicon product set from PCR reaction #1, dilute it ten fold, then apply 1-2 µl of that diluted primary amplicon mix as template for a second PCR reaction which can be initiated with the same universal 16S DNA primer set used in the first PCR reaction, or a primer set which targets a subset of the 16S PCR gene amplified in the primary reaction.

Step 5. The secondary PCR reaction is diluted in hybridization buffer and analysed via hybridization to a microarray which contains probes which are specific to variations of the 16S gene sequence that are know to distinguish one prokaryotes in a mixture of prokaryotes: the result being 16S DNA based analysis of a set of prokaryotic organisms in a way that bypasses DNA purification prior to analysis.

EXAMPLE 10

Electrophoresis

Mouthwash, Dacron Cheek Swabs and saliva via two different ORAGENE™ collection products (ON-500, OG-510) from a cohort of twelve volunteers were collected. An independent reference HLA-Type was obtained for all volunteers via analysis of purified DNA at LabCorp (Raleigh N.C.) an ASHI-certified HLA-Typing laboratory and each was processed as described, subjected to the respective A, B or DRB1 specific tandem PCR reaction. 5 uL of the resulting secondary PCR product was then applied directly to gels for semi-quantitative analysis by gel electrophoresis.

Figure 12A:
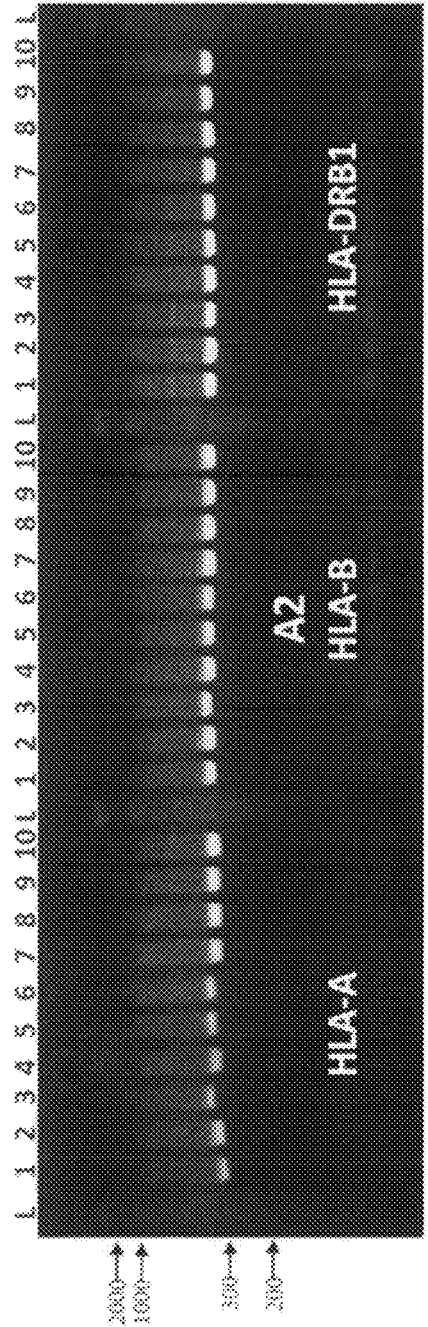
FIGS. 12A-12B are gels showing Secondary PCR Amplicons for Representative Samples A2 & A9. Samples A2 and A9 were diluted 1:10 for raw buccal swabs, 1:20 for raw mouthwash, and 1:50 for raw ORAGENE™ kits, saliva sample collection kits, for which 1 ul was used as input on primary (1°) PCR. Purified DNA was used undiluted at 1 ul. The primary PCR product was diluted 1:100 prior to addition of 2.5 uL to the secondary PCR reaction: for all samples except raw buccal swabs which were diluted 1:10 prior to the secondary (2°) PCR. The majority of samples amplified, as above, without protocol adjustment: except for raw buccal swab collection from A11 (which failed HLA-B amplification and required collection of a second swab, which then amplified correctly in the HLA-B reaction) and for raw mouthwash collection from A3: which required a 1:50 dilution of the re-suspended pellet to obtain HLA-A amplification. The following are the secondary PCR bands for each sample type for HLA-A, B, and DRB1. 1. Raw Buccal Swab Eluate; 2. Purified Buccal Swab Eluate; 3. Raw ORAGENE™ Eluate (ON-500); 4. Raw Post Incubation ORAGENE™ Eluate (ON-500); 5. Purified ORAGENE™ Eluate (ON-500); 6. Raw ORAGENE™ Eluate (OG-510); 7. Raw Post Incubation ORAGENE™ Eluate (OG-510); 8. Purified ORAGENE™ Eluate (OG-510); 9. Raw Mouthwash Collection Eluate; 10. Purified Mouthwash Eluate.
Figure 12B:
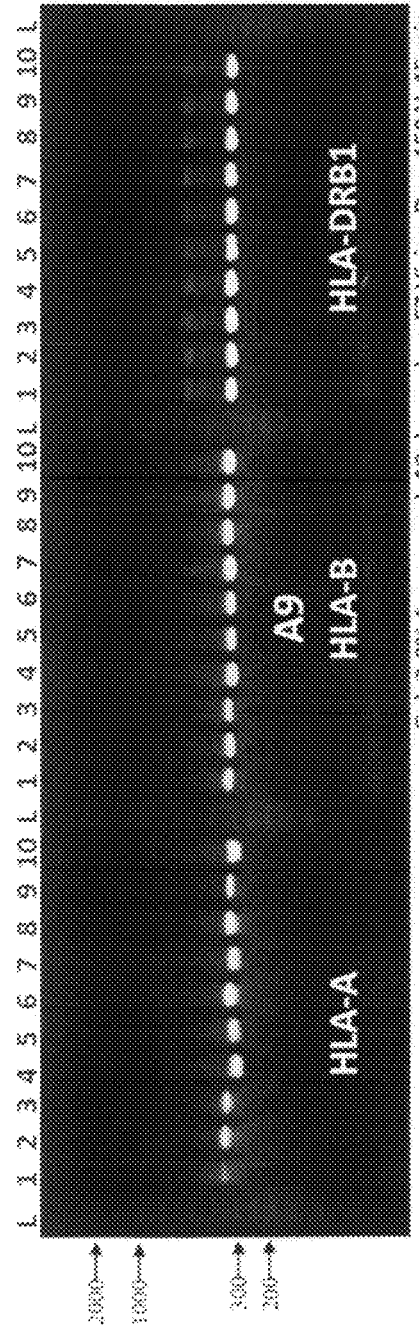
Figure 13A:
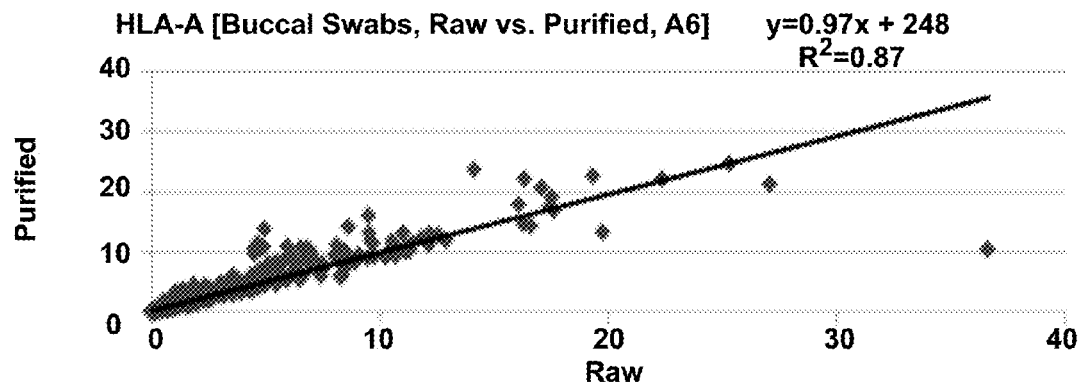
FIGS. 13A-13F show Correlation of Microarray Data: Raw vs. Purified DNA Samples: HLA-A. Microarray image data, obtained from microarrays have been analyzed to generate the integrated intensity for each of the microarray probe spots. Such microarrays are manufactured with probes printed in triplicate. For the data, the numerical average of those simple repeats has been used for analysis. The data are presented as scatter plots, where the Y-axis comprises microarray probe intensity data for each probe, obtained from hybridization to purified DNA samples that had been extracted from each of the several sample types. The X-axis comprises the microarray hybridization data obtained from the corresponding matched raw samples: i.e. each data point on such scatter plots corresponds to an ordered pair [x, y] obtained from a single microarray probe, for two matched sample types [raw, purified DNA]. These data have been fit to a simple linear regression [y=mx+b] to yield a slope (m) and intercept (b) and a squared linear correlation coefficient $R^2$. 6 sets of purified vs. raw samples have been analyzed: buccal swabs, mouthwash, ORAGENE™ OG-510, ORAGENE™ OG-510 without heat treatment, ORAGENE™ ON-500, ORAGENE™ ON-500 with heat treatment. Data have been displayed for only one of the 12 volunteers (A6).
Figure 13B:
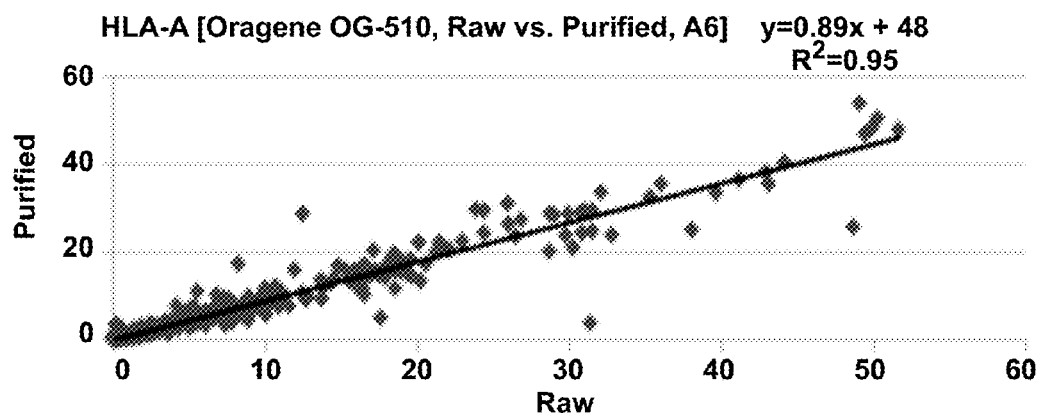
Figure 13C:
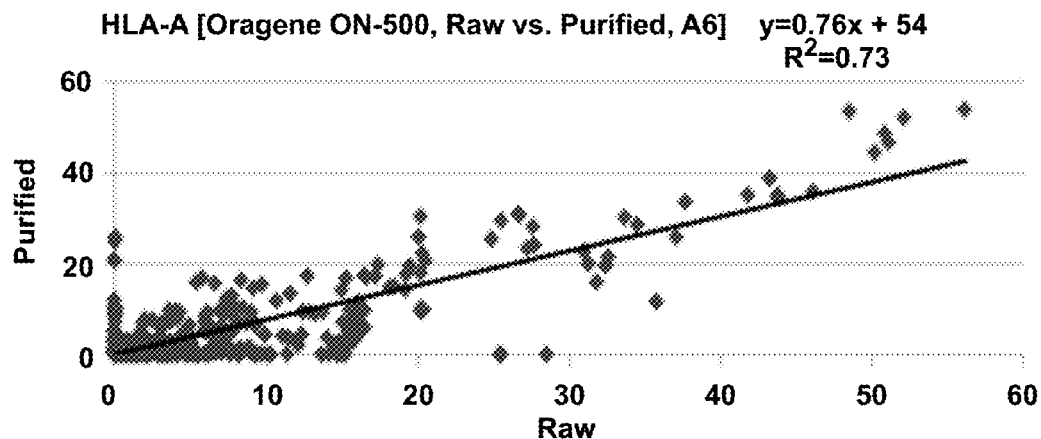
Figure 13D:
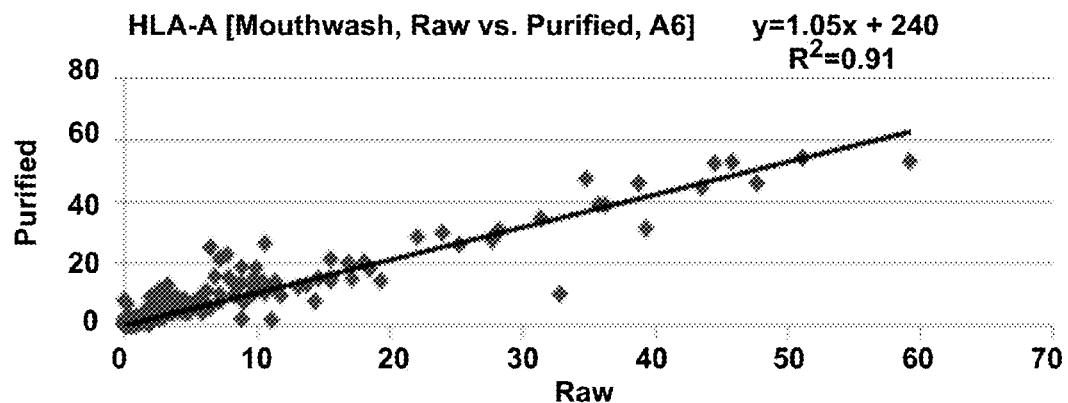
Figure 13E:
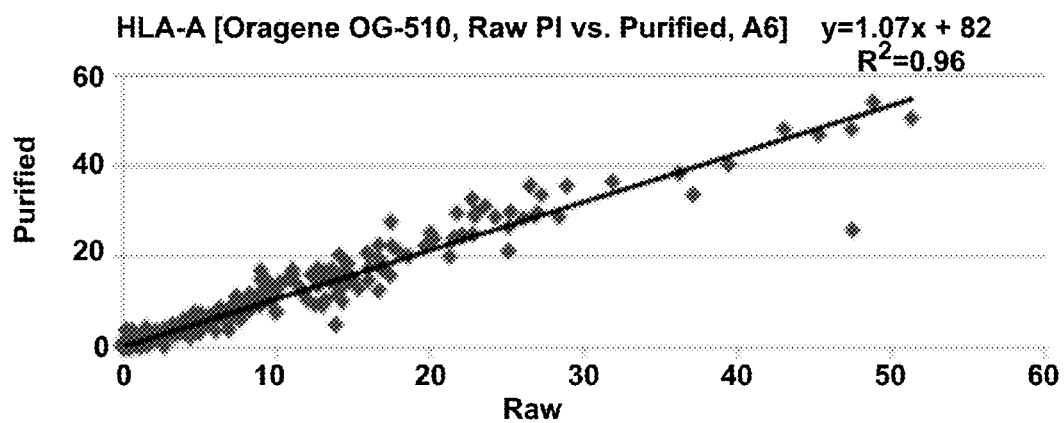
Figure 13F:
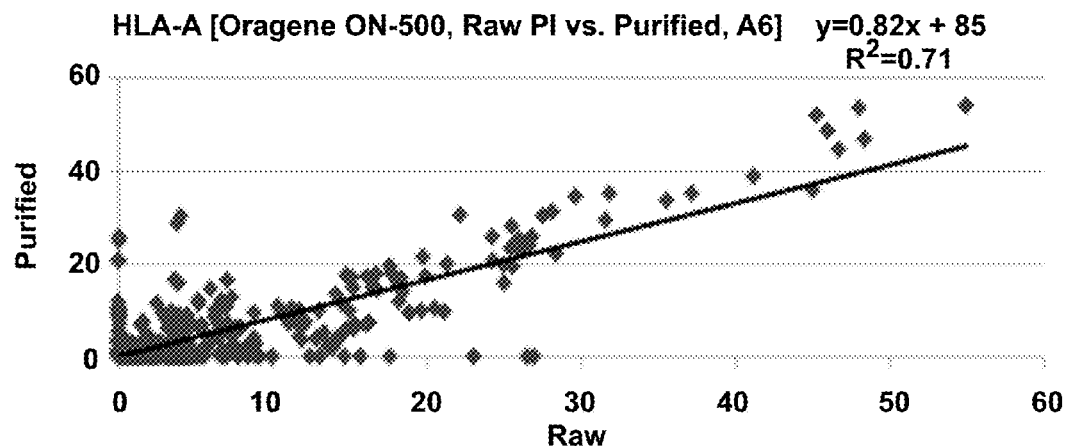
Figure 14A:
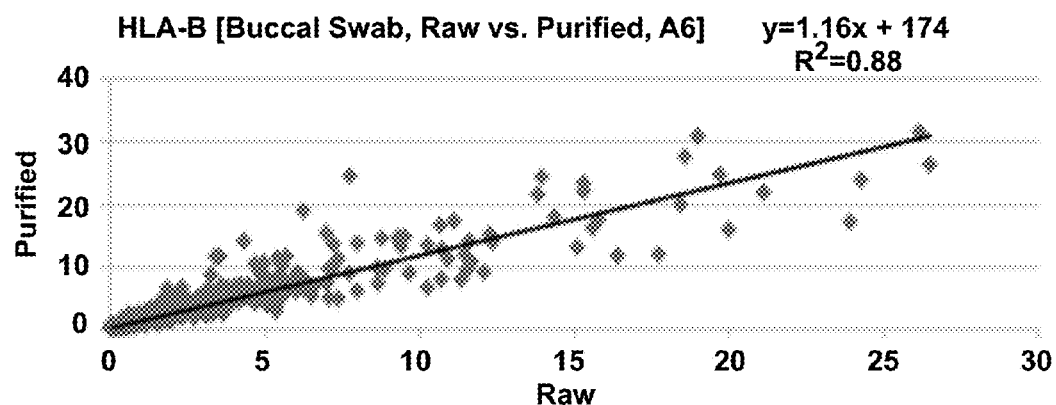
FIGS. 14A-14F show Correlation of Microarray Data: Raw vs. Purified DNA Samples: HLA-B. Microarray image data, obtained from arrays have been analyzed to generate the integrated intensity for each of the microarray probe spots. Such microarrays are manufactured with probes printed in triplicate. For the data, the numerical average of those simple repeats has been used for analysis. The data are presented as scatter plots, where the Y-axis comprises microarray probe intensity data obtained from purified DNA samples that had been extracted from each of the several sample types. The X-axis comprises the microarray hybridization data obtained from the corresponding matched raw samples: i.e. each data point on such scatter plots corresponds to an ordered pair [x,y] obtained from a single microarray probe for the two related sample types [raw, purified DNA]. These data have been fit to a simple linear regression [y=mx+b] to yield a slope (m) and intercept (b) and a squared linear correlation coefficient $R^2$. 6 sets of purified vs. raw samples have been analyzed: buccal swabs, mouthwash, ORAGENE™ OG-510, ORAGENE™ OG-510 without heat treatment, ORAGENE™ ON-500, ORAGENE™ ON-500 with heat treatment.
Figure 14B:
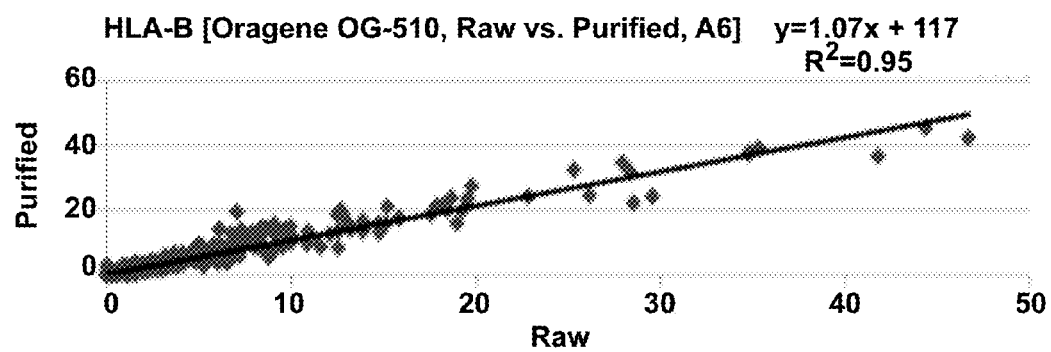
Figure 14C:
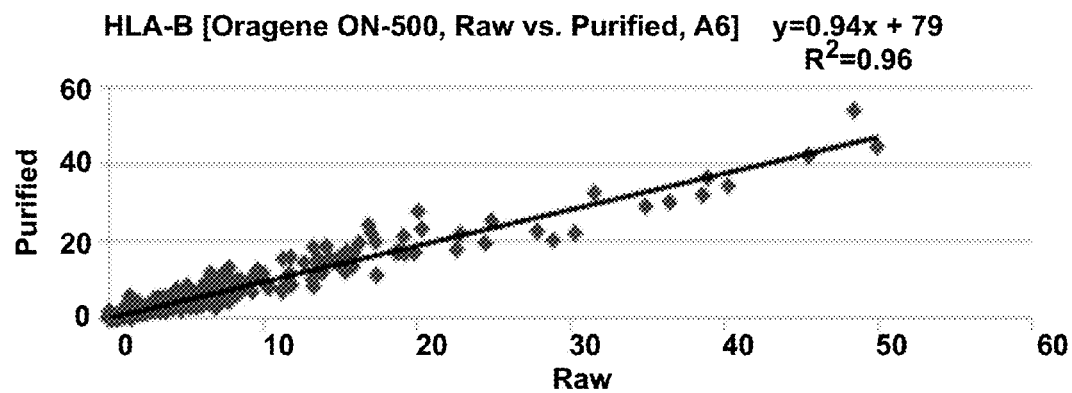
Figure 14D:
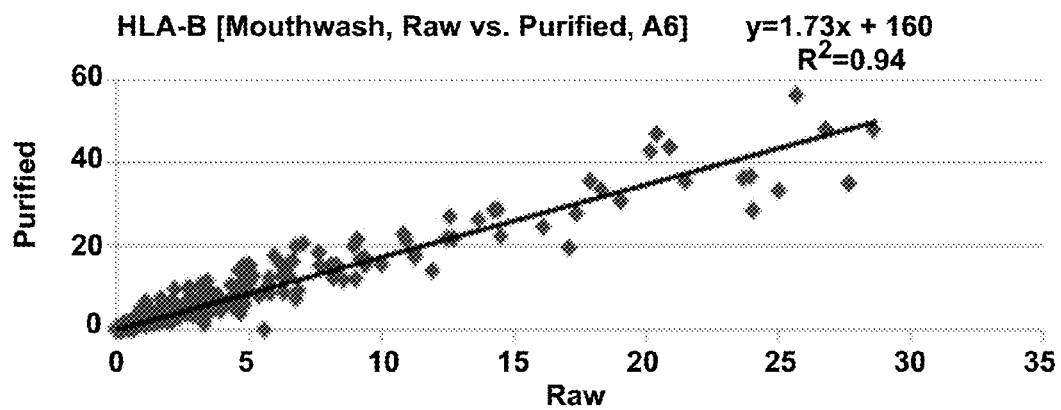
Figure 14E:
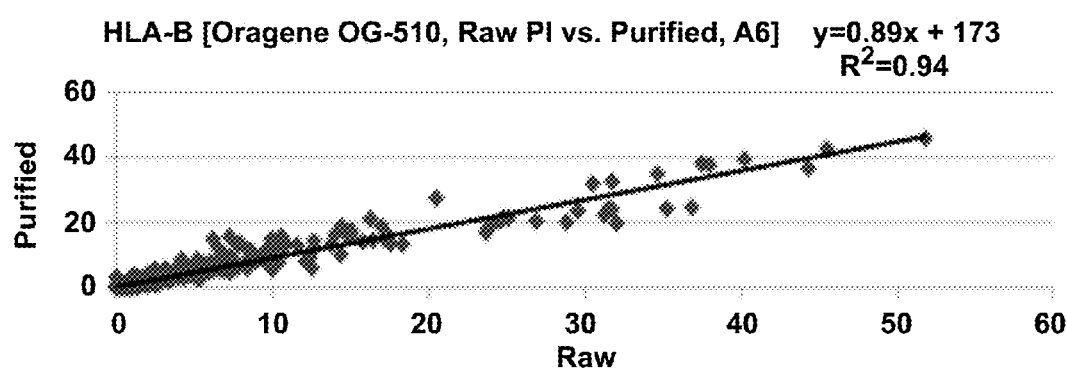
Figure 14F:
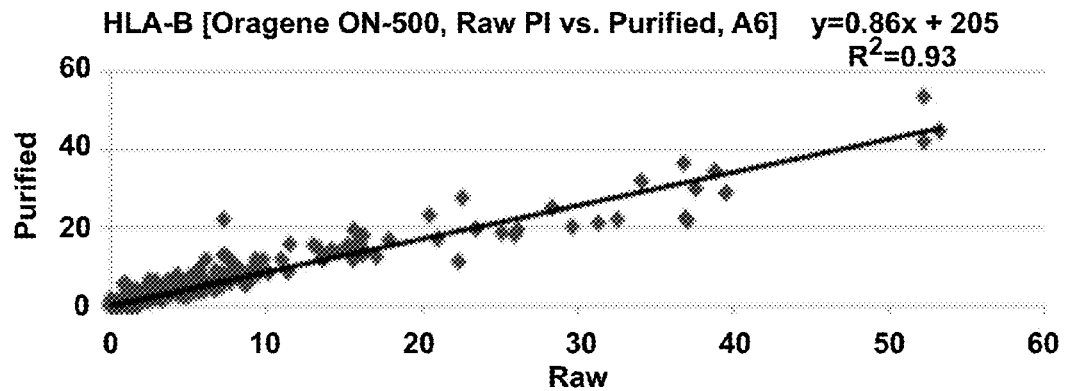
Figure 15A:
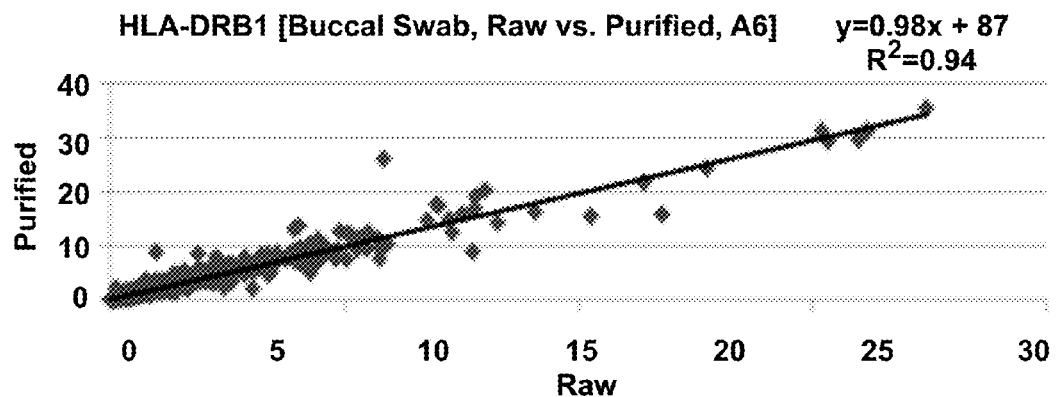
FIGS. 15A-15F show Correlation of Microarray Data: Raw vs. Purified DNA Samples: HLA-$DRB_1$. Microarray image data, obtained from arrays have been analyzed to generate the integrated intensity for each of the microarray probe spots. Such microarrays are manufactured with probes printed in triplicate. For the data, the numerical average of those simple repeats has been used for analysis. The data are presented as scatter plots, where the Y-axis comprises microarray probe intensity data obtained from purified DNA samples that had been extracted from each of the several sample types. The X-axis comprises the microarray hybridization data obtained from the corresponding matched raw samples: i.e. each data point on such scatter plots corresponds to an ordered pair [x,y] obtained from a single microarray probe for the two related sample types [raw, purified DNA]. These data have been fit to a simple linear regression [y=mx+b] to yield a slope (m) and intercept (b) and a squared linear correlation coefficient $R^2$. 6 sets of purified vs. raw samples have been analyzed: buccal swabs, mouthwash, ORAGENE™ OG-510, ORAGENE™ OG-510 without heat treatment, ORAGENE™ ON-500, ORAGENE™ ON-500 with heat treatment.
Figure 15B:
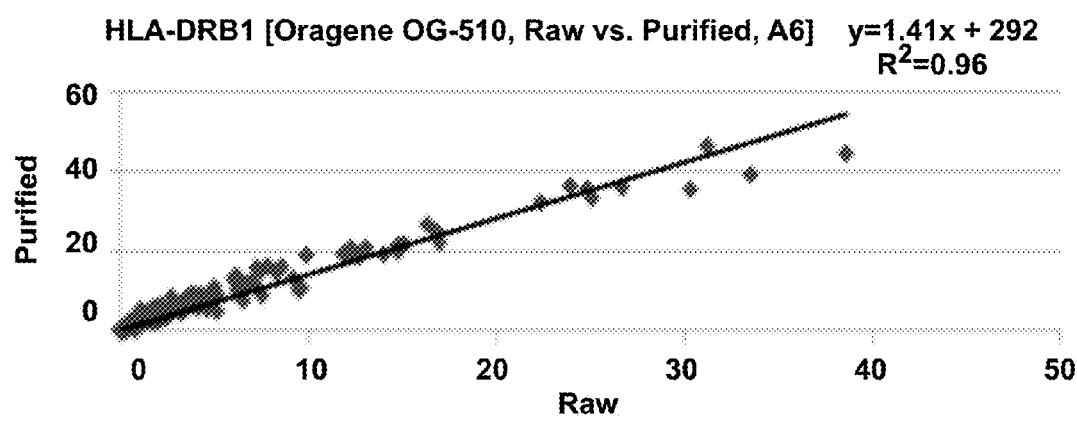
Figure 15C:
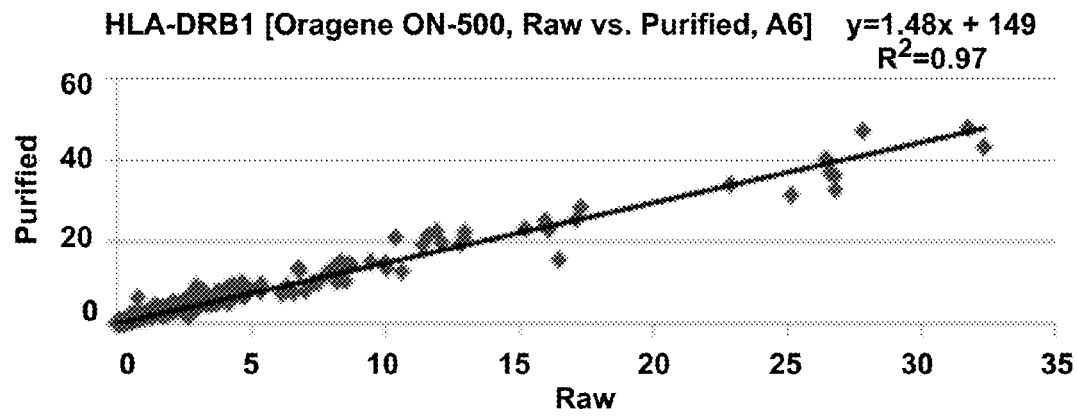
Figure 15D:
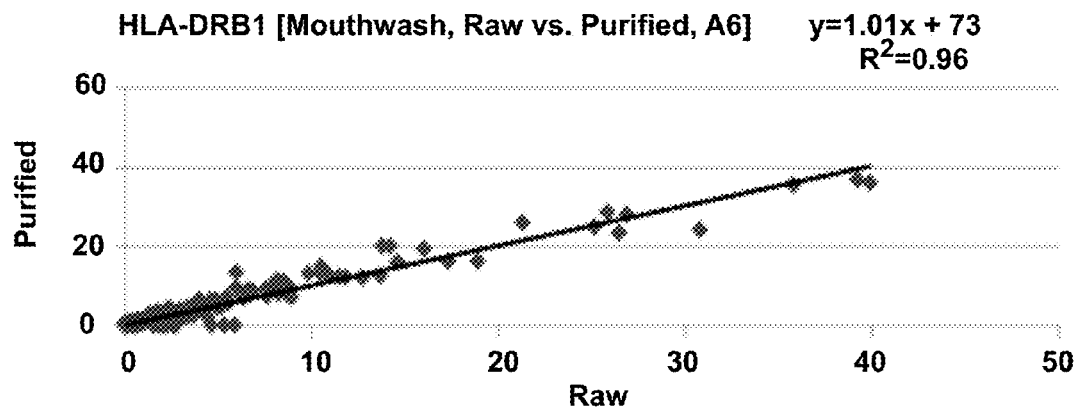
Figure 15E:
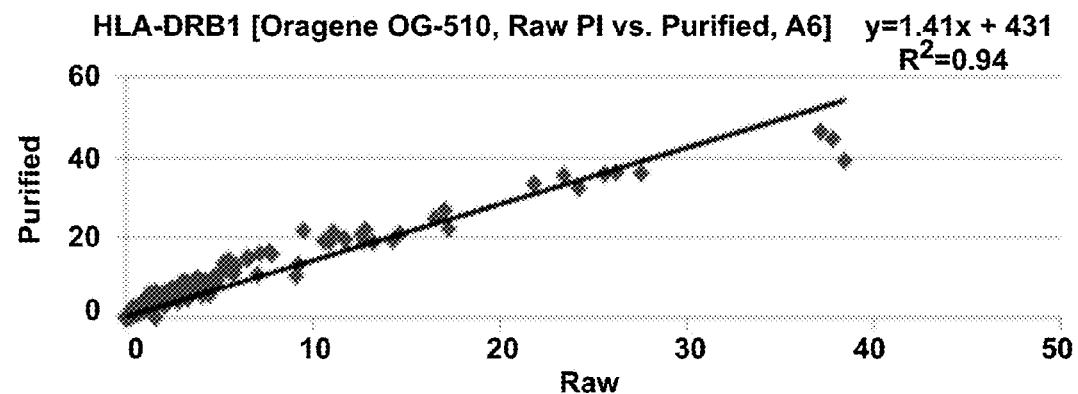
Figure 15F:
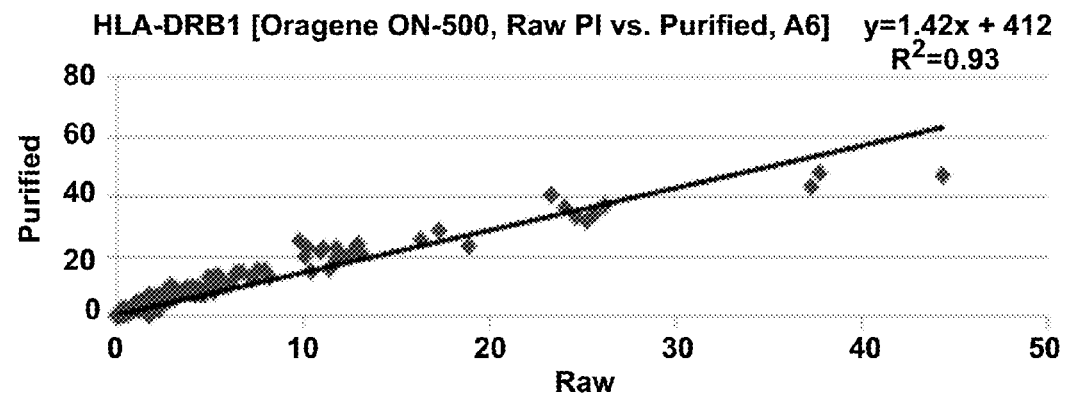

Representative electrophoresis data of that kind are displayed in FIG. 12, for samples A2 & A9. As seen in FIG. 12, the un-adjusted secondary PCR reaction product for all three HLA genes [A,B & DRB1] and for all 10 sample types [raw and purified] converge to a relatively constant mass yield of amplicon, as would be expected for the primer limited 2° PCR reaction.

EXAMPLE 11

Sample Collection & Processing

Buccal swabs, mouthwash, and ORAGENE™ ON-500 and OG-510 collections were taken from twelve individuals who refrained from eating or drinking two hours prior to collection. Participants swabbed the inside of their cheeks vigorously up and down twenty times with a Dacron swab. Swabs were placed into 15 mL conical tubes without treatment and loosely capped for drying under a laminar flow hood for 72 hours. Swabs were rehydrated in 150 μl of 100 mM Borate+1 mM EDTA and heated at 70° C. for 2.5 hours.

Raw buccal swab eluate was recovered by pipetting directly into the swab and used without additional treatment for PCR and microarray analysis. When used for comparison, DNA was purified from such swabs via Qiagen's QIAamp DNA Blood Mini Kit (Catalog Number 51104) following manufacturer's protocol. A second swab was collected from each individual and shipped to LabCorp (Raleigh N.C.) where DNA was extracted and used for high resolution HLA genotyping via SSOP and supplementary SSP and SBT. LabCorp required that a second set of swabs be collected for six of the twelve samples, due to errors obtained in the first set of HLA-calls obtained via Lab Corp SSOP—SSP-SBT suite of tests.

Mouthwash was collected when participants vigorously swished 10 mL of Scope mouthwash (Original Mint, 15% alcohol) for 45 seconds and expectorated into 50 mL conical tubes. Collections were centrifuged at 6000×g for 5 minutes. The pellet was retained and washed in 10 mL of 20% ethanol. Centrifugation was repeated and the retained pellet was reconstituted in 300 μl of 100 mM Borate+1 mM EDTA and heated at 70° C. for 2.5 hours. A second 10 mL mouthwash collection was performed and purified via a Qiagen kit as described above. These collections were centrifuged at 6000×g for 5 minutes. Two 10 mL washes were performed with 1×PBS before resuspension of the pellet as directed by the Qiagen protocol.

Saliva was collected using ORAGENE™ kits ON-500 and OG-510, as directed by the manufacturer (DNA Genotek). After collection, each ORAGENE™ collection tube was divided into three aliquots: two used in the raw form and one processed to obtain purified DNA. The first raw aliquot was used as-is. The second raw aliquot was allowed to incubate for 3 hours at 50° C. to yield "raw post incubation (PI) eluate". The third aliquot was processed to yield DNA as per manufacturer's instructions.

EXAMPLE 12

Sample Quality Control

Purified DNA was quantified via Quant-iT PicoGreen dsDNA Kit (Invitrogen), as per manufacturer instruction. Gel electrophoresis was used to confirm amplification for the primary and secondary PCR reactions for raw and purified specimens. The 1° PCR product was visualized by combining with EZ vision loading dye (Amresco) on a 2.0% Agarose gel on a standard UV transilluminator. The 2° PCR product was analyzed via the FlashGel DNA System (Lonza) on a 1.2% pre-cast gel.

The following references were cited herein:
1. Charron D. Vox Sang 2011, 100(1):163-166. doi: 10.1111/j.1423-0410.2010.01438.x.
2. Eng H. S., Leffell M. S. J Immunol Methods 2011, 369(1-2):1-21.
3. Fry T. J. Pediatr Blood Cancer 2010, 55(6):1043-1044.
4. Kostenko L. et. al Tissue Antigens 2011 Apr. 19 e-pub
5. Agundez A. J. et. al. Expert Opin Drug Metab Toxicol. 2011 Apr. 8. e-pub
6. International MHC and Autoimunnity Genetics Network. Proc. Nat. Acad. Sci. USA 2009 106(44):18680-18685. Epub 2009 Oct. 21.
7. Catassi C., Fasano A. Am. J. Med. 2011, 123:691-693.
8. Van Belle T. L. et al. Physiol. Rev. 2011, 1: 79-118
9. Poland G. A. OMICs 2011, Jul. 6. e-pub
10. Sheldon S., Poulton K. Methods Mol Biol, 2006, 333: 157-174.
11. Dunbar S. A. Clin Chim Acta 2006, 363(1-2): 71-82. Epub 2005 Aug. 15.
12. Horton R. et al. Immunogenetics. 2008, 60(1): 1-18. Epub 2008 Jan. 10.
13. Bentley G. et al. Tissue Antigens 2009, 74(5): 393-403.
14. Hogan M. E. et al. U.S. Pat. No. 7,354,710. Issued Apr. 28, 2008.
15. Hogan M. E. et al. U.S. Pat. No. 7,667,026. Issued Feb. 23, 2010.
16. Shi L. et. al. Nature Biotechnology 2006, 24, 1151-1161.
17. www.ncbi.nlm.nih.gov/projects/gv/mhc/ihwg.cgi.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The present examples, along with the methods, procedures and systems described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for amplifying a DNA of interest, comprising:
contacting fluidically isolated rings on a Guthrie card with samples of raw umbilical cord blood;
rehydrating the raw umbilical cord blood in each ring prior to a first PCR performed on each rehydrated raw sample;
performing the first PCR on said rehydrated raw samples without purifying DNA contained therein to produce first amplicons;
diluting the first amplicons; and
performing a second PCR thereon until all primers used in the second PCR reaction are consumed to produce second amplicons, thereby amplifying the DNA from the raw umbilical cord blood samples to final amplified DNA product concentrations that are limited by the primer concentration in the second PCR reactions, said second PCR reactions independent of the amount or purity of the DNA comprising the original raw umbilical cord blood, wherein the primers for the second PCR reaction are a set of multiple exon-specific primers with sequences shown SEQ ID NOS: 15-27 and target DNA sequences contained within the amplified product of the first PCR reaction.

2. The method of claim 1, wherein said rehydrated raw umbilical cord samples comprise a set of gene targets, said method comprising:
performing the first PCR in parallel to produce a first set of amplicons;
diluting the first set of amplicons; and
performing a second PCR thereon, using the entire set of primary amplicon products as a set of templates for the second PCR reaction until all secondary PCR primers are consumed to produce a second amplicon set, thereby amplifying the DNA.

3. The method of claim 2, wherein less than 5 gene targets, less than 10 gene targets or less than 20 gene targets are amplified in parallel.

4. The method of claim 2, wherein the gene targets are HLA-DRB 1, DQ-A1 and DQB1, are DQ-A1 and DQ-B1 or are HLA-B and KIR.

5. The method of claim 2, wherein the gene targets are two hypervariable regions near the mitochondrial origin of replication and one or more additional mitochondrial genes.

6. The method of claim 2, wherein the gene targets are segments of microbe-specific microbial 16S DNA genes, said method detecting microbes in the raw samples.

7. The method of claim 1, further comprising labeling the second PCR primers with one or more fluorophores.

8. The method of claim 7, wherein the fluorophor is a cyanine dye.

9. The method of claim 8, wherein the DNA comprises one or more genes of interest, further comprising:
hybridizing the second amplicon to probes having sequences of allele variations associated with the gene of interest;
detecting a fluorescence pattern from the hybridized amplicon; and
assigning an allelotype based on the fluorescence pattern.

10. The method of claim 9, wherein the gene(s) of interest are an HLA-A gene, an HLA-B gene, an HLA-DRB1 gene, an HLA-DQA1 gene, or an HLA-DQB 1 gene.

11. The method of claim 9, wherein hybridizing is performed on HLA-Chips containing microarrays.

12. The method of claim 1, wherein primers for the first PCR are locus-specific primers.

13. The method of claim 12, wherein the primers have sequences shown in SEQ ID NOS: 1-14.

14. The method of claim 1, wherein the sample comprises DNA from a bacterium or a virus.

15. The method of claim 1, further comprising:
sequencing the second amplicon for an analysis thereof; and
analyzing the sequencing data using the Ricimer allele calling algorithm.

16. The method of claim 15, wherein analysis determines the type of viral or bacterial contamination.

17. The method of claim 15, wherein analysis determines one or more of identity, paternity of an individual, forensic information, tissue matching, risk factors for the development of disease, or response to medication.

18. The method of claim 1, wherein said rings are outlined with hydrophobic paint.

19. The method of claim 1, wherein the DNA is mitochondrial DNA.

* * * * *

SEQUENCE LISTING

```
<160> NUMBER OF SEQ ID NOS: 27

<210> SEQ ID NO 1
<211> LENGTH: 20
<212> TYPE: DNA
<213> ORGANISM: Artificial sequence
<220> FEATURE:
<223> OTHER INFORMATION: forward HLA-A locus primary primer 1

<400> SEQUENCE: 1
gcctctgygg ggagaagcaa                                              20

<210> SEQ ID NO 2
<211> LENGTH: 22
<212> TYPE: DNA
<213> ORGANISM: Artificial sequence
```

```
<220> FEATURE:
<223> OTHER INFORMATION: reverse HLA-A locus primary primer 1

<400> SEQUENCE: 2
gtcccaattg tctcccctcc tt                                              22

<210> SEQ ID NO 3
<211> LENGTH: 22
<212> TYPE: DNA
<213> ORGANISM: Artificial sequence
<220> FEATURE:
<223> OTHER INFORMATION: forward HLA-B locus primary primer 2a

<400> SEQUENCE: 3
gggaggagcg aggggaccgc ag                                              22

<210> SEQ ID NO 4
<211> LENGTH: 22
<212> TYPE: DNA
<213> ORGANISM: Artificial sequence
<220> FEATURE:
<223> OTHER INFORMATION: forward HLA-B locus primary primer 2b

<400> SEQUENCE: 4
gggaggagag aggggaccgc ag                                              22

<210> SEQ ID NO 5
<211> LENGTH: 22
<212> TYPE: DNA
<213> ORGANISM: Artificial sequence
<220> FEATURE:
<223> OTHER INFORMATION: forward HLA-B locus primary primer 2c

<400> SEQUENCE: 5
gggaggagca aggggaccgc ag                                              22

<210> SEQ ID NO 6
<211> LENGTH: 23
<212> TYPE: DNA
<213> ORGANISM: Artificial sequence
<220> FEATURE:
<223> OTHER INFORMATION: reverse HLA-B locus primary primer 1

<400> SEQUENCE: 6
ggaggccatc ccgggcgatc tat                                             23

<210> SEQ ID NO 7
<211> LENGTH: 23
<212> TYPE: DNA
<213> ORGANISM: Artificial sequence
<220> FEATURE:
<223> OTHER INFORMATION: reverse HLA-B locus primary primer 3

<400> SEQUENCE: 7
ggaggccatc cccggcgacc tat                                             23

<210> SEQ ID NO 8
<211> LENGTH: 24
<212> TYPE: DNA
<213> ORGANISM: Artificial sequence
<220> FEATURE:
<223> OTHER INFORMATION: reverse HLA-B locus primary primer 3a

<400> SEQUENCE: 8
ttctccattc aacggagggc gaca                                            24
```

<210> SEQ ID NO 9
<211> LENGTH: 24
<212> TYPE: DNA
<213> ORGANISM: Artificial sequence
<220> FEATURE:
<223> OTHER INFORMATION: reverse HLA-A locus primary primer 3c

<400> SEQUENCE: 9
ttctccattc aagggagggc gaca                                              24

<210> SEQ ID NO 10
<211> LENGTH: 21
<212> TYPE: DNA
<213> ORGANISM: Artificial sequence
<220> FEATURE:
<223> OTHER INFORMATION: forward HLA-DRB1 locus primary primer 1a

<400> SEQUENCE: 10
cttggaggtc tccagaacag g                                                 21

<210> SEQ ID NO 11
<211> LENGTH: 21
<212> TYPE: DNA
<213> ORGANISM: Artificial sequence
<220> FEATURE:
<223> OTHER INFORMATION: forward HLA-DRB1 locus primary primer 1b

<400> SEQUENCE: 11
cttagaggtc tccagaaccg g                                                 21

<210> SEQ ID NO 12
<211> LENGTH: 25
<212> TYPE: DNA
<213> ORGANISM: Artificial sequence
<220> FEATURE:
<223> OTHER INFORMATION: reverse HLA-DRB1 locus primary primer 4-xx

<400> SEQUENCE: 12
cacacacaca cacacactca gattc                                             25

<210> SEQ ID NO 13
<211> LENGTH: 25
<212> TYPE: DNA
<213> ORGANISM: Artificial sequence
<220> FEATURE:
<223> OTHER INFORMATION: reverse HLA-DRB1 locus primary primer 4-07

<400> SEQUENCE: 13
cacacacaca accacactca gattc                                             25

<210> SEQ ID NO 14
<211> LENGTH: 25
<212> TYPE: DNA
<213> ORGANISM: Artificial sequence
<220> FEATURE:
<223> OTHER INFORMATION: reverse HLA-DRB1 locus primary primer 4-10

<400> SEQUENCE: 14
cacacacaca cacagagtca gattc                                             25

<210> SEQ ID NO 15
<211> LENGTH: 29
<212> TYPE: DNA
<213> ORGANISM: Artificial sequence
<220> FEATURE:
<223> OTHER INFORMATION: forward HLA-A exon 2 secondary primer 2b-24

-continued

```
<400> SEQUENCE: 15
agcctggttc actsctcgyc cccaggctc                                            29

<210> SEQ ID NO 16
<211> LENGTH: 33
<212> TYPE: DNA
<213> ORGANISM: Artificial sequence
<220> FEATURE:
<223> OTHER INFORMATION: reverse HLA-A exon 2 secondary primer 2a-28

<400> SEQUENCE: 16
tactacaacc ttgcccgctc tggttgtagt agc                                       33

<210> SEQ ID NO 17
<211> LENGTH: 30
<212> TYPE: DNA
<213> ORGANISM: Artificial sequence
<220> FEATURE:
<223> OTHER INFORMATION: forward HLA-A exon 3 secondary primer 2b-24

<400> SEQUENCE: 17
gtgagaacta gtcsgggcca ggttctcaca                                           30

<210> SEQ ID NO 18
<211> LENGTH: 28
<212> TYPE: DNA
<213> ORGANISM: Artificial sequence
<220> FEATURE:
<223> OTHER INFORMATION: reverse HLA-A exon 3 secondary primer 2b-26

<400> SEQUENCE: 18
gtaccaggtt cccgtggccc cyggtacc                                             28

<210> SEQ ID NO 19
<211> LENGTH: 30
<212> TYPE: DNA
<213> ORGANISM: Artificial sequence
<220> FEATURE:
<223> OTHER INFORMATION: forward HLA-B exon 2 secondary primer 2c-20

<400> SEQUENCE: 19
accctcttga gccgcgccgg kaggagggtc                                           30

<210> SEQ ID NO 20
<211> LENGTH: 34
<212> TYPE: DNA
<213> ORGANISM: Artificial sequence
<220> FEATURE:
<223> OTHER INFORMATION: reverse HLA-B exon 2 secondary primer 2a-28

<400> SEQUENCE: 20
tactacaacc ttgcctcgct ctggttgtag tagc                                      34

<210> SEQ ID NO 21
<211> LENGTH: 29
<212> TYPE: DNA
<213> ORGANISM: Artificial sequence
<220> FEATURE:
<223> OTHER INFORMATION: forward HLA-B exon 3 secondary primer 2a-22

<400> SEQUENCE: 21
gtgagactta ccggggccag ggtctcaca                                            29

<210> SEQ ID NO 22
```

```
<211> LENGTH: 28
<212> TYPE: DNA
<213> ORGANISM: Artificial sequence
<220> FEATURE:
<223> OTHER INFORMATION: reverse HLA-B exon 3 secondary primer 2a-26

<400> SEQUENCE: 22
gtaccaggtt cccactgccc ctggtacc                                           28

<210> SEQ ID NO 23
<211> LENGTH: 33
<212> TYPE: DNA
<213> ORGANISM: Artificial sequence
<220> FEATURE:
<223> OTHER INFORMATION: forward DRB-1 exon 2 secondary primer 3-xx-24

<400> SEQUENCE: 23
aacgtgcttt ttcgtgtccc cacagcacgt ttc                                     33

<210> SEQ ID NO 24
<211> LENGTH: 33
<212> TYPE: DNA
<213> ORGANISM: Artificial sequence
<220> FEATURE:
<223> OTHER INFORMATION: forward DRB-1 exon 2 secondary primer 3-04-24

<400> SEQUENCE: 24
aacgtgcttt ttcttgtccc cccagcacgt ttc                                     33

<210> SEQ ID NO 25
<211> LENGTH: 33
<212> TYPE: DNA
<213> ORGANISM: Artificial sequence
<220> FEATURE:
<223> OTHER INFORMATION: forward DRB-1 exon 2 secondary primer 3-07-24

<400> SEQUENCE: 25
aacgtgcttt tttgtgcccc cacagcacgt ttc                                     33

<210> SEQ ID NO 26
<211> LENGTH: 28
<212> TYPE: DNA
<213> ORGANISM: Artificial sequence
<220> FEATURE:
<223> OTHER INFORMATION: reverse DRB-1 exon 2 secondary primer 3-xx-20

<400> SEQUENCE: 26
tgcagctttg ctcacctcgc cgctgcac                                           28

<210> SEQ ID NO 27
<211> LENGTH: 28
<212> TYPE: DNA
<213> ORGANISM: Artificial sequence
<220> FEATURE:
<223> OTHER INFORMATION: reverse DRB-1 exon 2 secondary primer 3-09-22

<400> SEQUENCE: 27
tgcagagttg cttacctcgc ctctgcac                                           28
```